United States Patent
Mao et al.

(10) Patent No.: US 8,318,723 B2
(45) Date of Patent: Nov. 27, 2012

(54) PYRAZINE COMPOUNDS, THEIR USE AND METHODS OF PREPARATION

(75) Inventors: Wang Mao, Milford, CT (US); Tina Marie Morwick, New Milford, CT (US); Anthony S. Prokopowicz, III, Stormville, NY (US)

(73) Assignee: Boehringer Ingelheim International GmbH, Ingelheim (DE)

( * ) Notice: Subject to any disclaimer, the term of this patent is extended or adjusted under 35 U.S.C. 154(b) by 603 days.

(21) Appl. No.: 12/377,283

(22) PCT Filed: Aug. 15, 2007

(86) PCT No.: PCT/US2007/075946
§ 371 (c)(1),
(2), (4) Date: Feb. 12, 2009

(87) PCT Pub. No.: WO2008/022164
PCT Pub. Date: Feb. 21, 2008

(65) Prior Publication Data
US 2010/0210627 A1    Aug. 19, 2010

Related U.S. Application Data

(60) Provisional application No. 60/822,546, filed on Aug. 16, 2006.

(51) Int. Cl.
*A61K 31/55* (2006.01)
*A61K 31/4965* (2006.01)
(52) U.S. Cl. .............................. 514/217.05; 514/255.06
(58) Field of Classification Search ............. 514/255.06, 514/217.05
See application file for complete search history.

(56) References Cited

FOREIGN PATENT DOCUMENTS
WO           02060492 A1    8/2002
WO        2005058876 A1    6/2005

OTHER PUBLICATIONS

International Search Report dated Feb. 26, 2008.
Morwick, Tina "Pim kinase inhibitors: a survey of the patent literature" Expert Opin. Ther. Patents (2010) 20 (2) pgs. 193-212.

*Primary Examiner* — San-Ming Hui
(74) *Attorney, Agent, or Firm* — Michael P. Morris; David A. Dow; Usha R. Patel

(57) ABSTRACT

The invention provides compounds according to formula (I)

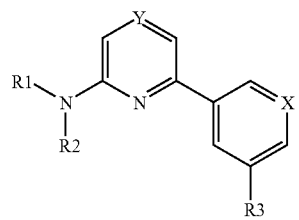

their use and methods for preparation wherein A, X, Y, R1, R2 and R3 are defined herein. The compounds of the invention inhibit specific serine/threonine kinases involved in inflammatory processes and aberrant cell proliferation, and are thus useful for treating associated diseases and pathological conditions such as Pim kinase-mediated diseases and pathological conditions involving inflammation, including Chron's disease, inflammatory bowel disease, rheumatoid arthritis, and chronic inflammatory disease, or aberrant cell proliferation including various cancers.

10 Claims, No Drawings

PYRAZINE COMPOUNDS, THEIR USE AND METHODS OF PREPARATION

APPLICATION DATA

This application is a 371 National Stage filing of PCT/US2007/075946 filed on Aug. 15, 2007. This application also claims benefit to U.S. provisional application Ser. No. 60/822,546 filed on Aug. 16, 2006.

FIELD OF THE INVENTION

The invention relates to compounds of formula I,

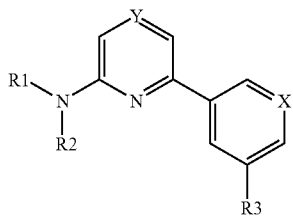

The compounds of the invention inhibit specific serine/threonine kinases involved in inflammatory processes and aberrant cell proliferation, and are thus useful for treating associated diseases and pathological conditions such as Pim kinase-mediated diseases and pathological conditions involving inflammation, including but not limited to Chron's disease, inflammatory bowel disease, rheumatoid arthritis, and chronic inflammatory disease, or aberrant cell proliferation including various cancers.

BACKGROUND OF THE INVENTION

The Pim kinases form a distinct family of serine/threonine kinases and have been implicated as having a functional role in cell survival (Amaravadi et al., J. Clin. Invest. 115: 2618 (2005)). Pim-2 is a highly conserved serine/threonine kinase involved in cell proliferation, meiosis and the prevention of apoptosis (Baytel et al., Biochim. Biophys. Acta Gene Struct. Expr. 1442: 274 (1998)). Murine Pim-2, also known at Tic-1, has been reported to be about 53% identical in sequence at the amino acid level to the proto-oncogene Pim-1, and to be expressed at low levels in a variety of tissues, with the highest expression in the brain and thymus (van der Lugt et al., EMBO J. 14(11): 2536 (1995)). Both the Pim-1 and the Pim-2 loci are common sites of provirus integration and studies have suggested that these kinases act in a functionally redundant fashion in tumorigenesis (Haupt et al., Cell 65: 753 (1991); Bruer et al., EMBO J. 8: 743 (1989); Cuypers et al., Cell. 37: 141 (1984); van der Lugt et al., EMBO J. 14(11): 2536 (1995)). The Pim-1 proto-oncogene is believed to be one of the most potent collaborators of myc proto-oncogenes in inducing lymphomagenesis in mice (van der Lugt et al., EMBO J. 14(11): 2536 (1995)). Allen et al. (Oncogene 15: 1133 (1997)) suggest, based on proviral tagging experiments, that Pim-2 is similar in oncogenic behavior to Pim-1. They note that while Pim-1 and Pim-2 differ with respect to basal expression in tissues, both genes are highly expressed in response to the same cytokines, and they describe a Pim-2 transgene in lymphoid cells which was seen to predispose mice to T-cell lymphomas like those promoted by pim-1 transgenes. Additionally, several reports have linked abnormal expression of Pim kinases to various human cancers including prostate (Valdman et al., Prostate 60: 367 (2004)), chronic lymphocytic leukemia and non-Hodgkin's lymphoma (Cohen et al., Leuk. Lymphoma 45: 951 (2004)), and multiple myeloma (Claudio et al., Blood 100: 2175 (2002)).

As iterated above, both Pim-1 and Pim-2 genes, encode labile, cytoplasmic serine/threonine kinases. Phosphorylation of protein substrates by serine/threonine kinases is often involved in the transduction of signals from the cell surface receptors to intracellular effectors. It is believed that Pim-2, like Pim-1, is a target for gp130-mediated signal transducer and transcriptional activator 3 ("STAT3") signaling. As is known to those of ordinary skill in the art, the activation of STAT3 by the cytokine receptor gp130 is required for both G1 to S cell cycle transition, as well as, anti-apoptosis (Shirogane et al., Immunity 11: 709 (1999)).

Baytel et al. (Biochim. Biophys. Acta Gene Struct. Expr. 1442: 274 (1998)) report cloning of the h-Pim-2 gene. In comparison to mouse Pim-2, h-Pim-2 is reported by Baytel et al. to encode a protein that shares 90% identity and 93% similarity at the primary structure level. At the RNA level, two Pim-2 transcripts have been identified in humans, a 2.2 kb transcript that is highly expressed in hematopoietic tissues and in leukemic and lymphoma cell lines, and a 5.0 kb transcript that is detectable in spleen, thymus, small intestine and colon apoptosis (Baytel et al., Biochim. Biophys. Acta Gene Struct. Expr. 1442: 274 (1998)). The Pim-2 gene in humans is believed to be X-linked (van der Lugt et al., EMBO J. 14(11): 2536 (1995)).

It has recently been disclosed (Li et al., J. Biol. Chem. 276: 18579 (2001) that Pim-2 is induced by lipopolysaccharide (LPS) in a variety of cell lines. Studies suggest that up-regulation of Pim-2 in 70Z3 cells by LPS is controlled by the IKK/NF-κB pathway. Gold et al. (J. of Immunol. 168: 744 (2002)) have recently reported that Pim-1 is a target of CD-40 signaling in B cells, and the increase in Pim-1 expression observed as a consequence of CD40 signaling was regulated via the NF-κB pathway.

Aberrant protein serine/threonine activity has been implicated, or is suspected in a number of pathologies including septic shock, bone loss, psoriasis, rheumatoid arthritis, many cancers and other proliferative diseases (See, U.S. Pat. No. 6,165,716 to Creasy et al. (Issue Date: Dec. 20, 2000)). Researchers have expended considerable time to identify serine/threonine protein kinases that may be involved mechanistically in various pathological conditions. Inhibition of such kinases may thereby be useful in the prevention and/or amelioration of various dysfunctions or diseases. For example, U.S. Pat. No. 5,972,606 to Creasy et al. discloses a human protein serine/threonine kinase, designated HOACF72, of the hYAK1 family of polypeptides, antibodies against which are said to be useful in the treatment of bone loss, inflammatory diseases such as rheumatoid arthritis, osteoarthritis, adult respiratory disease syndrome (ARDS), inflammatory bowel disease (IBD), psoriasis, dermatitis, asthma, allergies, infections, septic shock, pain, cancers, anorexia, bulimia, and a host of other conditions. U.S. Pat. Nos. 5,965,420 and 6,165,766, also to Creasy et al. (Issue Dates: Oct. 12, 1999 and Dec. 26, 2000, respectively), assert human YAK3 polypeptides and polynucleotides, antibodies against which are said to be useful for treating bone loss, inflammatory diseases, infections, immunodeficiency disorders, septic shock, pain, cancers and a host of other pathological conditions. Therefore, there is a need for identification and characterization of further members of the serine/threonine protein kinase family to identify kinases which may be involved in pathological processes. There is also a need to identify potential relationships between these kinases and disease states themselves.

The work cited above supports the principle that inhibition of Pim kinases will be beneficial in the treatment of diseases. Therefore, a need exists for small molecule inhibitors for treating these diseases with optimized efficacy, pharmacokinetic and safety profiles.

Pyrazine compounds and derivatives thereof have been disclosed in the art. WO2005058876A1 (Axxima Pharmaceuticals AG) discloses pyrazine derivatives for use in treatment of infectious diseases. WO2002060492 (Cytopia) is directed to methods of inhibiting kinases. U.S. Pat. No. 6,340,759 (Eisai) is directed to fused pyridine derivatives for use as a medicament having a serotonin antagonism.

SUMMARY OF THE INVENTION

It is therefore an object of the invention to provide compounds of formula (I)

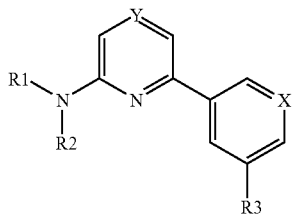

wherein X, Y, R1, R2 and R3 are defined below.

DETAILED DESCRIPTION OF THE PREFERRED EMBODIMENTS

In a broad generic aspect of the invention there is provided a compound of the formula (I)

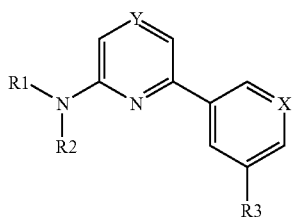

A compound of Formula I wherein:
X is C or N
Y is C or N
R1 is Hydrogen, C1-C3 alkyl,
R2 is Hydrogen, C1-C5 alkyl, C3-C8 cycloalkyl, C3-C8 heterocycloalkyl, each optionally independently substituted with 1-3 R4, wherein R4 is selected from C1-C5 alkyl, C1-C5 alkoxy, carboxamido, acyl, benzyl, C3-C8 cycloalkyl, C3-C8 heterocycloalkyl, hydroxyl and amino optionally mono or disubstituted with C1-C4 alkyl;
wherein each R4 is optionally independently substituted with 1-3 substituents selected from C1-C5 alkyl, C1-C5 alkoxy, acyl, benzyl, C3-C8 cycloalkyl, C3-C8 heterocycloalkyl, hydroxyl and amino optionally mono or disubstituted with C1-C4 alkyl or;
wherein R1 and R2 together with the nitrogen atom to which they are attached form a C3-C8 ring containing 1-3 heteroatoms and which is optionally substituted by 1-3 R5, wherein R5 is selected from C1-C5 alkyl, C1-C5 alkoxy, carboxamido, acyl, benzyl, C3-C8 cycloalkyl, C3-C8 heterocycloalkyl, hydroxyl, and amino optionally mono or disubstituted with C1-C4 alkyl; wherein each R5 is optionally independently substituted by with substituents selected from hydroxyl, C1-C5 alkoxy, or amino optionally mono or disubstituted with C1-C4 alkyl;
R3 is

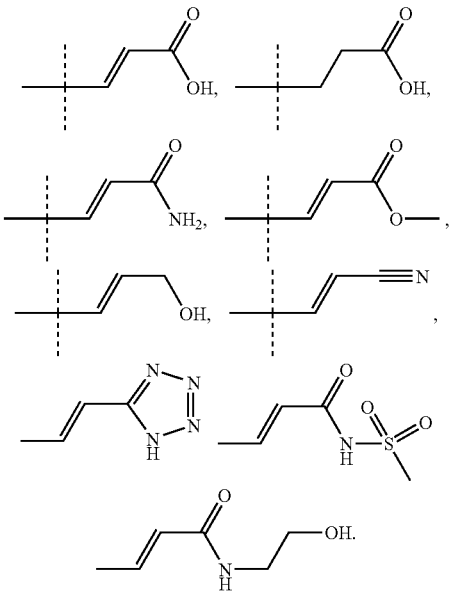

In another embodiment there is provided a compound wherein:
X is C or N
Y is C or N
R1 is Hydrogen, C1-C3 alkyl R2 is C1-C5 alkyl, C3-C8 cycloalkyl, C3-C8 heterocycloalkyl, each optionally independently substituted with 1-3 R4, wherein R4 is selected from C1-C5 alkyl, C1-C5 alkoxy, carboxamido, benzyl, C3-C8 cycloalkyl, C3-C8 heterocycloalkyl, hydroxyl and amino optionally mono or disubstituted with C1-C4 alkyl;
wherein each R4 is optionally independently substituted with 1-3 substituents selected from C1-C5 alkyl, C1-C5 alkoxy, acyl, benzyl, hydroxyl and amino optionally mono or disubstituted with C1-C4 alkyl
or;
wherein R1 and R2 together with the nitrogen atom to which they are attached form a C3-C8 ring containing 1-3 heteroatoms and which is optionally substituted by 1-3 R5, wherein R5 is selected from C1-C5 alkyl, C1-C5 alkoxy, carboxamido, acyl, benzyl, hydroxyl and amino optionally mono or disubstituted with C1-C4 alkyl; wherein each R5 is optionally independently substituted with substituents selected from hydroxyl, C1-C5 alkoxy, or amino optionally mono or disubstituted with C1-C4 alkyl
R3 is

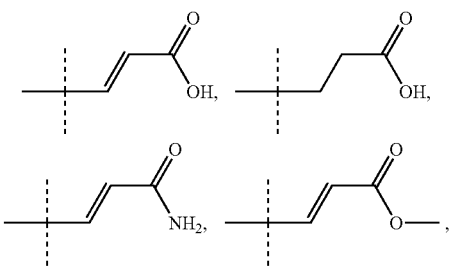

-continued

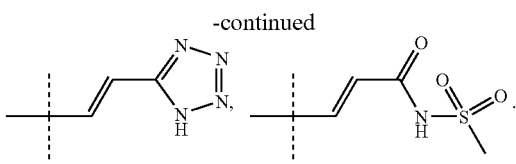

In yet another embodiment there is provided a compound wherein:
X is C
Y is C or N
R1 is Hydrogen, C1-C3 alkyl R2 is C1-C5 alkyl, C3-C8 cycloalkyl, C3-C8 heterocycloalkyl, each optionally independently substituted with 1-3 R4, wherein R4 is selected from C1-C5 alkyl, C1-C5 alkoxy, carboxamido, benzyl, C3-C8 cycloalkyl, C3-C8 heterocycloalkyl, hydroxyl and amino optionally mono or disubstituted with C1-C4 alkyl; wherein each R4 is optionally independently substituted with 1-3 substituents selected from C1-C5 alkyl, C1-C5 alkoxy, benzyl, hydroxyl and amino optionally mono or disubstituted with C1-C4 alkyl
or;
wherein R1 and R2 together with the nitrogen atom to which they are attached form a C3-C8 ring containing 1-3 heteroatoms and which is optionally substituted by 1-3 R5, wherein R5 is selected from C1-C5 alkyl, C1-C5 alkoxy, carboxamido, benzyl, hydroxyl and amino optionally mono or disubstituted with C1-C4 alkyl; wherein each R5 is optionally independently substituted with substituents selected from hydroxyl, C1-C5 alkoxy, or amino optionally mono or disubstituted with C1-C4 alkyl
R3 is

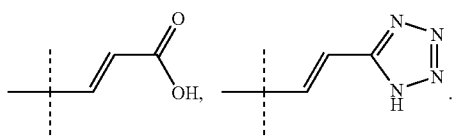

or the pharmaceutically acceptable salts and/or isomers thereof.

In another embodiment there is provided a compound of the invention as described immediately above and wherein:
X is C
Y is C or N
R1 is Hydrogen, C1-C3 alkyl
R2 is C1-C5 alkyl, C3-C8 cycloalkyl, each optionally independently substituted with 1-3 R4, wherein R4 is selected from carboxamido, C3-C8 heterocycloalkyl, hydroxyl and amino optionally mono or disubstituted with C1-C4 alkyl;
or;
wherein R1 and R2 together with the nitrogen atom to which they are attached form a C3-C8 ring containing 1-3 heteroatoms and which is optionally substituted by 1-3 R5,
wherein R5 is selected from C1-C3 alkyl, benzyl and amino optionally mono or disubstituted with C1-C4 alkyl; wherein each R5 is optionally independently substituted with amino optionally mono or disubstituted with C1-C4 alkyl
R3 is

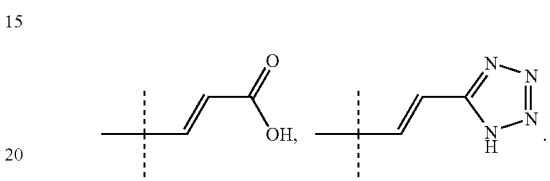

It is a further object of the invention to provide methods for treating PIM mediated diseases and pathological conditions involving inflammation such as osteoarthritis, Guillain-Barre syndrome, restenosis following percutaneous transluminal coronary angioplasty, Alzheimer disease, acute and chronic pain, atherosclerosis, reperfusion injury, bone resorption diseases, congestive heart failure, myocardial infarction, thermal injury, multiple organ injury secondary to trauma, acute purulent meningitis, necrotizing enterocolitis, and syndromes associated with hemodialysis, leukopheresis, and granulocyte transfusion, and cancers such as prostate, chronic lymphocytic leukemia and non-Hodgkin's lymphoma and multiple myeloma.

It is yet a further object of the invention to provide pharmaceutical compositions and processes of preparation of the above-mentioned novel compounds.

Another embodiment of the invention provides a method for treating inflammatory disease said method comprised of the step of administering to a patient in need thereof a therapeutically effective amount of a compound according to formula I or a pharmaceutically acceptable salt thereof.

Another embodiment of the invention provides a process for preparing PIM inhibitor compounds as disclosed herein.

The following are representative compounds of the invention:

TABLE I

| Cpd # | Structure | name |
|---|---|---|
| 1 | <img> | (E)-3-{3-[6-(4-Amino-cyclohexylamino)-pyrazin-2-yl]-phenyl}-acrylic acid |

TABLE I-continued

| Cpd # | Structure | name |
|---|---|---|
| 2 | 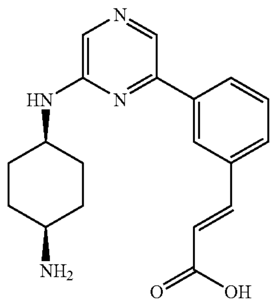 | (E)-3-{3-[6-(4-Amino-cyclohexylamino)-pyrazin-2-yl]-phenyl}-acrylic acid |
| 3 | 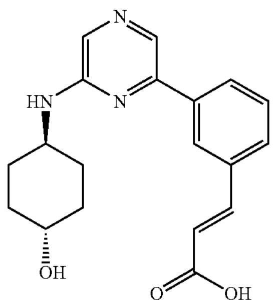 | (E)-3-{3-[6-(4-Hydroxy-cyclohexylamino)-pyrazin-2-yl]-phenyl}-acrylic acid |
| 4 | 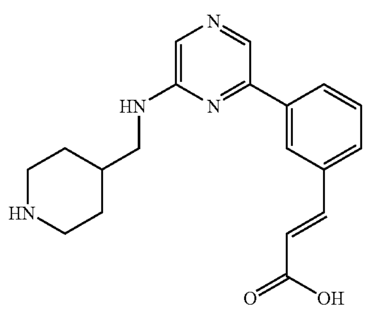 | (E)-3-(3-{6-[(Piperidin-4-ylmethyl)-amino]-pyrazin-2-yl}-phenyl)-acrylic acid |
| 5 | 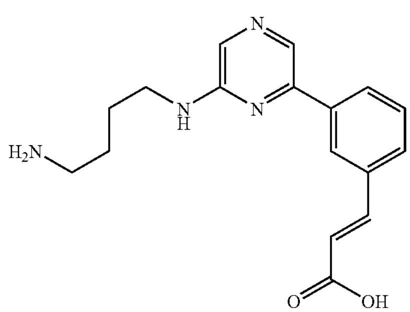 | (E)-3-{3-[6-(4-Amino-butylamino)-pyrazin-2-yl]-phenyl}-acrylic acid |
| 6 | 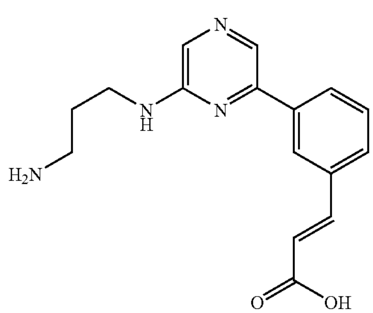 | (E)-3-{3-[6-(3-Amino-propylamino)-pyrazin-2-yl]-phenyl}-acrylic acid |

TABLE I-continued

| Cpd # | Structure | name |
|---|---|---|
| 7 | 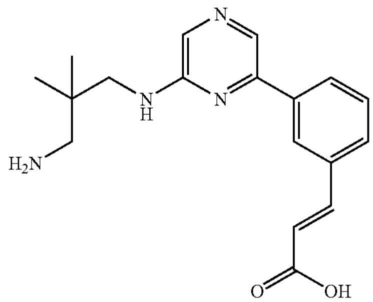 | (E)-3-{3-[6-(3-Amino-2,2-dimethyl-propylamino)-pyrazin-2-yl]-phenyl}-acrylic acid |
| 8 | 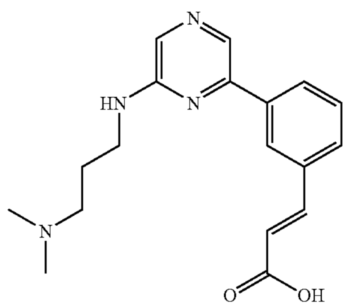 | (E)-3-{3-[6-(3-Dimethylamino-propylamino)-pyrazin-2-yl]-phenyl}-acrylic acid |
| 9 | 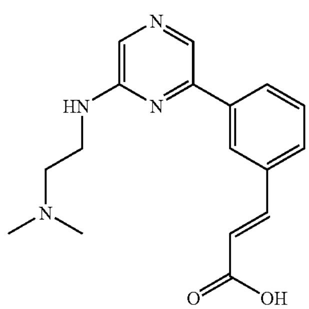 | (E)-3-{3-[6-(2-Dimethylamino-ethylamino)-pyrazin-2-yl]-phenyl}-acrylic acid |
| 10 | 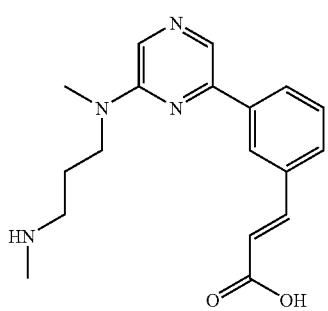 | (E)-3-(3-{6-[Methyl-(3-methylamino-propyl)-amino]-pyrazin-2-yl}-phenyl)-acrylic acid |
| 11 | 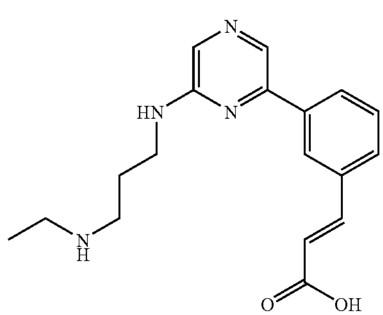 | (E)-3-{3-[6-(3-Ethylamino-propylamino)-pyrazin-2-yl]-phenyl}-acrylic acid |

TABLE I-continued

| Cpd # | Structure | name |
|---|---|---|
| 12 | 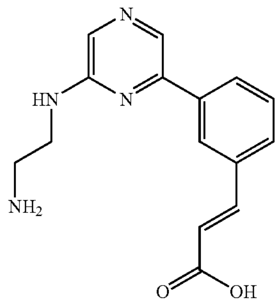 | (E)-3-{3-[6-(2-Amino-ethylamino)-pyrazin-2-yl]-phenyl}-acrylic acid |
| 13 | 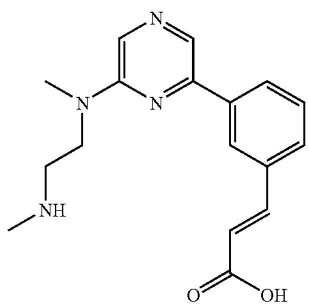 | (E)-3-(3-{6-[Methyl-(2-methylamino-ethyl)-amino]-pyrazin-2-yl}-phenyl)-acrylic acid |
| 14 | 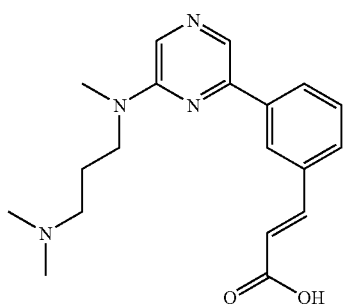 | (E)-3-(3-{6-[(3-Dimethylamino-propyl)-methyl-amino]-pyrazin-2-yl}-phenyl)-acrylic acid |
| 15 | 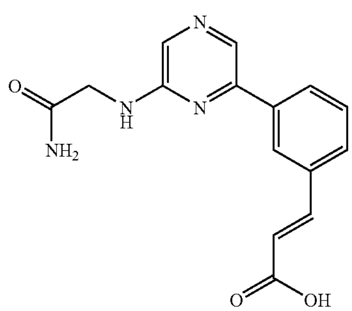 | (E)-3-{3-[6-(Carbamoylmethyl-amino)-pyrazin-2-yl]-phenyl}-acrylic acid |
| 16 | 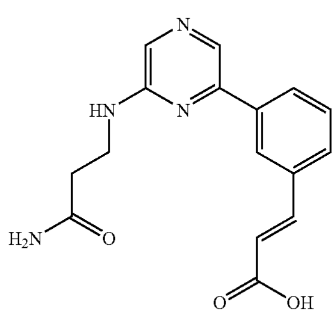 | (E)-3-{3-[6-(2-Carbamoyl-ethylamino)-pyrazin-2-yl]-phenyl}-acrylic acid; MS, electrospray |

TABLE I-continued

| Cpd # | Structure | name |
|---|---|---|
| 17 | 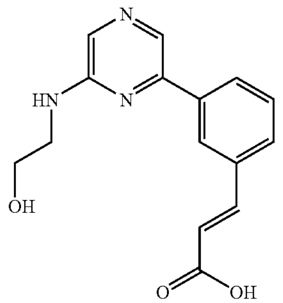 | (E)-3-{3-[6-(2-Hydroxy-ethylamino)-pyrazin-2-yl]-phenyl}-acrylic acid |
| 18 | 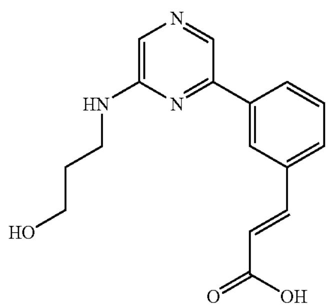 | E)-3-{3-[6-(3-Hydroxy-propylamino)-pyrazin-2-yl]-phenyl}-acrylic acid |
| 19 | 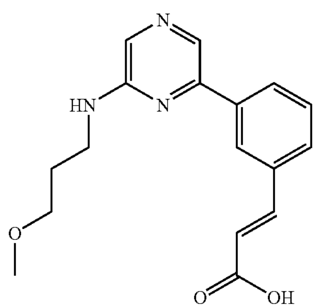 | (E)-3-{3-[6-(3-Methoxy-propylamino)-pyrazin-2-yl]-phenyl}-acrylic acid |
| 20 | 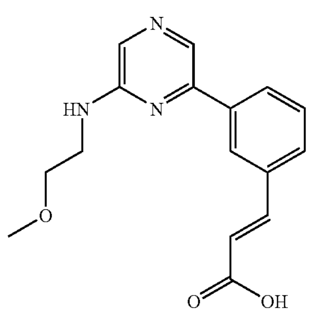 | (E)-3-{3-[6-(2-Methoxy-ethylamino)-pyrazin-2-yl]-phenyl}-acrylic acid |
| 21 | 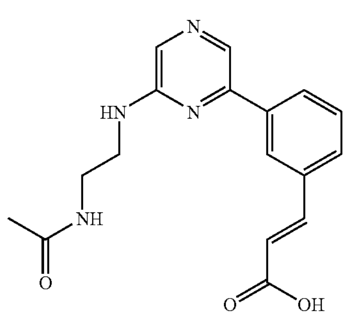 | (E)-3-{3-[6-(2-Acetylamino-ethylamino)-pyrazin-2-yl]-phenyl}-acrylic acid |

TABLE I-continued

| Cpd # | Structure | name |
|---|---|---|
| 22 | 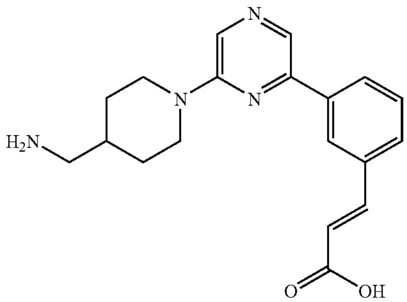 | (E)-3-{3-[6-(4-Aminomethyl-piperidin-1-yl)-pyrazin-2-yl]-phenyl}-acrylic acid |
| 23 | 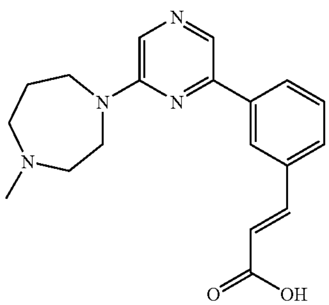 | (E)-3-{3-[6-(4-Methyl-[1,4]diazepan-1-yl)-pyrazin-2-yl]-phenyl}-acrylic acid |
| 24 | 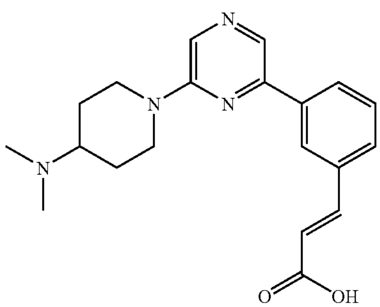 | (E)-3-{3-[6-(4-Dimethylamino-piperidin-1-yl)-pyrazin-2-yl]-phenyl}-acrylic acid |
| 25 | 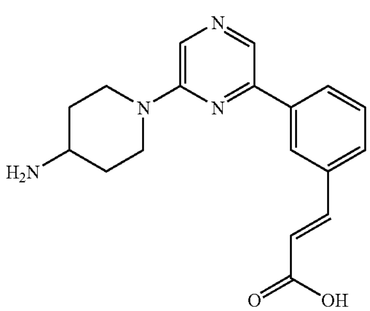 | Preparation of 14 (E)-3-{3-[6-(4-Amino-piperidin-1-yl)-pyrazin-2-yl]-phenyl}-acrylic acid |
| 26 | 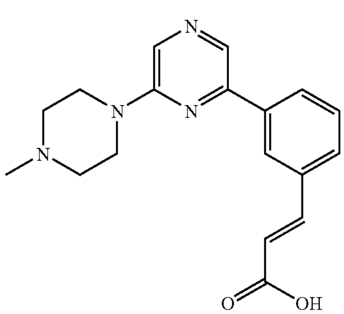 | (E)-3-[3-(4-Methyl-3,4,5,6-tetrahydro-2H-[1,2']bipyrazinyl-6'-yl)-phenyl]-acrylic acid |

TABLE I-continued

| Cpd # | Structure | name |
|---|---|---|
| 27 | 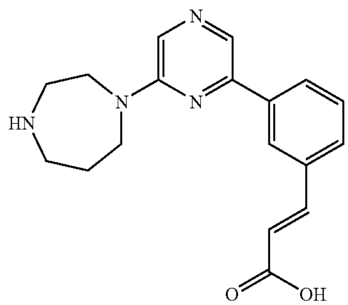 | (E)-3-[3-(6-[1,4]Diazepan-1-yl-pyrazin-2-yl)-phenyl]-acrylic acid |
| 28 | 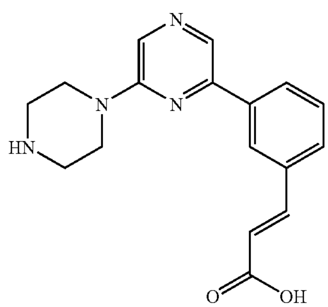 | (E)-3-[3-(3,4,5,6-Tetrahydro-2H-[1,2']bipyrazinyl-6'-yl)-phenyl]-acrylic acid |
| 29 | 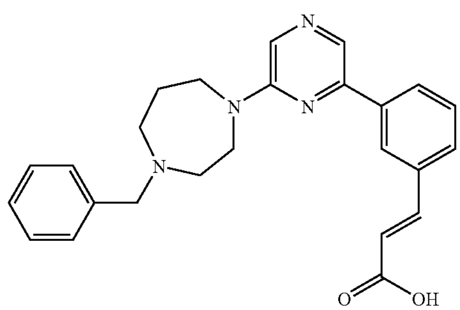 | (E)-3-{3-[6-(4-Benzyl-[1,4]diazepan-1-yl)-pyrazin-2-yl]-phenyl}-acrylic acid |
| 30 | 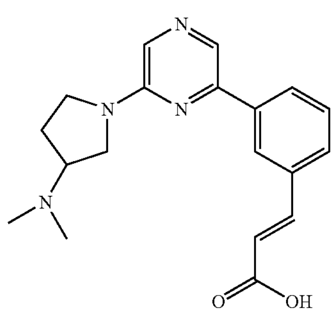 | (E)-3-{3-[6-(3-Dimethylamino-pyrrolidin-1-yl)-pyrazin-2-yl]-phenyl}-acrylic acid |
| 31 | 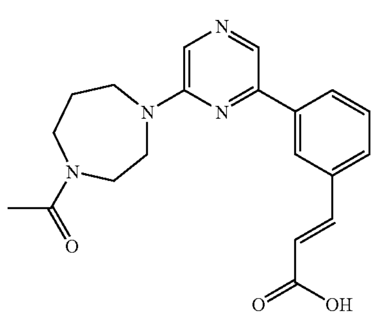 | (E)-3-{3-[6-(4-Acetyl-[1,4]diazepan-1-yl)-pyrazin-2-yl]-phenyl}-acrylic acid |

TABLE I-continued
| Cpd # | Structure | name |
|---|---|---|
| 32 | 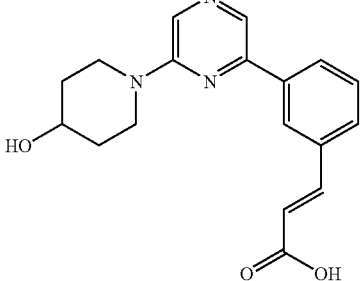 | (E)-3-{3-[6-(4-Hydroxy-piperidin-1-yl)-pyrazin-2-yl]-phenyl}-acrylic acid |
| 33 | 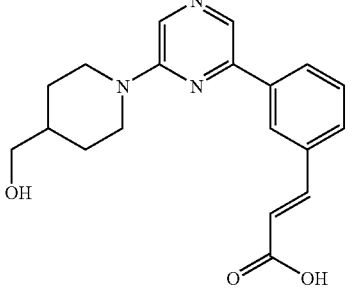 | (E)-3-{3-[6-(4-Hydroxymethyl-piperidin-1-yl)-pyrazin-2-yl]-phenyl}-acrylic acid |
| 34 | 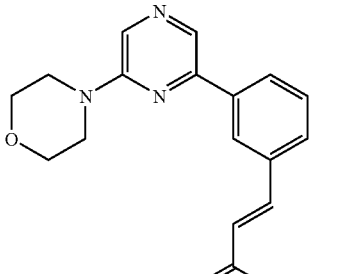 | (E)-3-[3-(6-Morpholin-4-yl-pyrazin-2-yl)-phenyl]-acrylic acid |
| 35 | 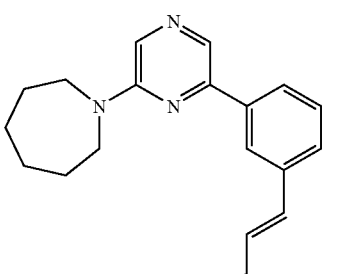 | (E)-3-[3-(6-Azepan-1-yl-pyrazin-2-yl)-phenyl]-acrylic acid |
| 36 | 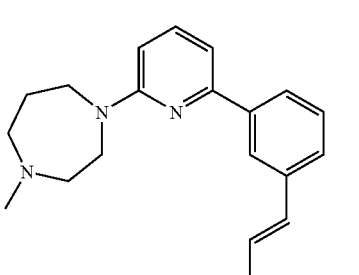 | (E)-3-{3-[6-(4-Methyl-[1,4]diazepan-1-yl)-pyridin-2-yl]-phenyl}-acrylic acid |

TABLE I-continued

| Cpd # | Structure | name |
|---|---|---|
| 37 | 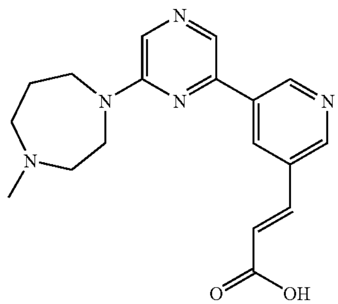 | (E)-3-{5-[6-(4-Methyl-[1,4]diazepan-1-yl)-pyrazin-2-yl]-pyridin-3-yl}-acrylic acid |
| 38 | 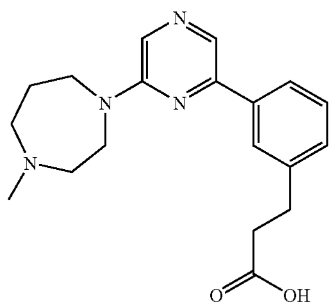 | 3-{3-[6-(4-Methyl-[1,4]diazepam-1-yl)-pyrazin-2-yl]-phenyl}-propionic acid |
| 39 | 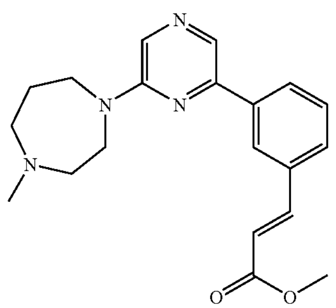 | (E)-3-{3-[6-(4-Methyl-[1,4]diazepan-1-yl)-pyrazin-2-yl]-phenyl}-acrylic acid methyl ester |
| 40 | 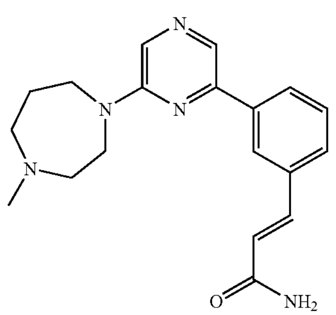 | (E)-3-{3-[6-(4-Methyl-[1,4]diazepan-1-yl)-pyrazin-2-yl]-phenyl}-acrylamide |
| 41 | 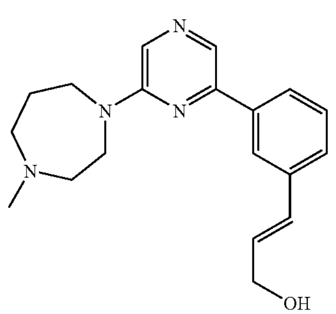 | (E)-3-{3-[6-(4-Methyl-[1,4]diazepan-1-yl)-pyrazin-2-yl]-phenyl}-prop-2-en-1-ol |

TABLE I-continued

| Cpd # | Structure | name |
|---|---|---|
| 42 | 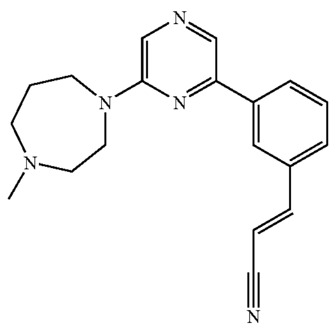 | (E)-3-{3-[6-(4-Methyl-[1,4]diazepan-1-yl)-pyrazin-2-yl]-phenyl}-acrylonitrile |
| 43 | 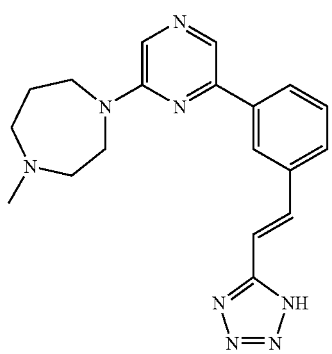 | 1-Methyl-4-(6-{3-[(E)-2-(1H-tetrazol-5-yl)-vinyl]-phenyl}-pyrazin-2-yl)-[1,4]diazepane |
| 44 | 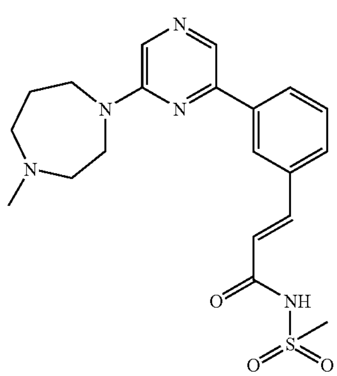 | N-((E)-3-{3-[6-(4-Methyl-perhydro-1,4-diazepin-1-yl)-pyrazin-2-yl]-phenyl}-acryloyl)-methanesulfonamide |
| 45 | 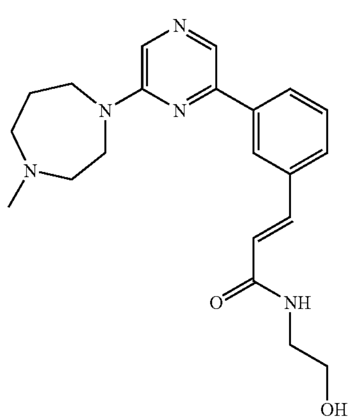 | (E)-N-(2-Hydroxy-ethyl)-3-{3-[6-(4-methyl-perhydro-1,4-diazepin-1-yl)-pyrazin-2-yl]-phenyl}-acrylamide |

TABLE I-continued

| Cpd # | Structure | name |
|---|---|---|
| 46 | 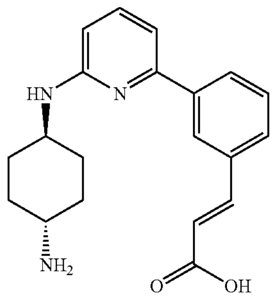 | (E)-3-{3-[6-(4-Amino-cyclohexylamino)-pyridin-2-yl]-phenyl}-acrylic acid |
| 47 | 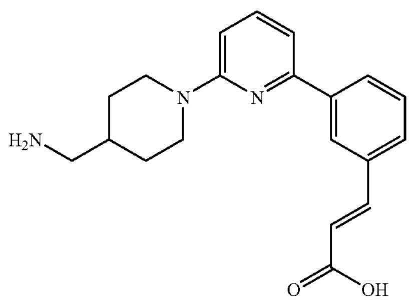 | (E)-3-[3-(4-Aminomethyl-3,4,5,6-tetrahydro-2H-[1,2']bipyridinyl-6'-yl)-phenyl]-acrylic acid |
| 48 | 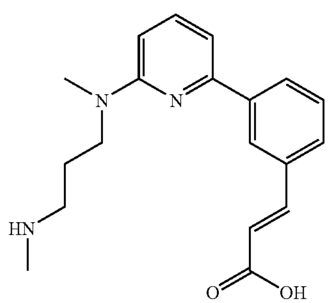 | (E)-3-(3-{6-[Methyl-(3-methylamino-propyl)-amino]-pyridin-2-yl}-phenyl)-acrylic acid |
| 49 | 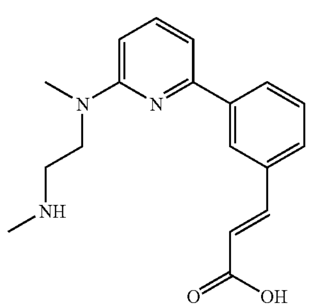 | (E)-3-(3-{6-[Methyl-(2-methylamino-ethyl)-amino]-pyridin-2-yl}-phenyl)-acrylic acid |
| 50 | 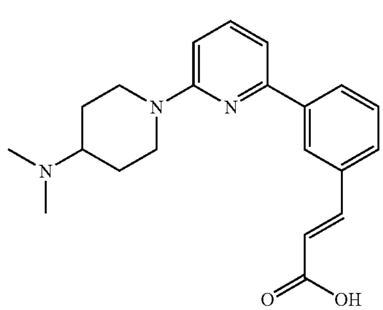 | (E)-3-[3-(4-Dimethylamino-3,4,5,6-tetrahydro-2H-[1,2']bipyridinyl-6'-yl)-phenyl]-acrylic acid |

TABLE I-continued

| Cpd # | Structure | name |
|---|---|---|
| 51 | 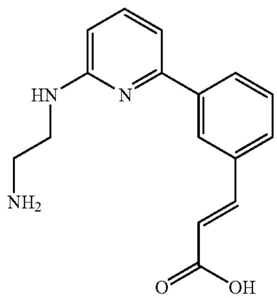 | (E)-3-{3-[6-(2-Amino-ethylamino)-pyridin-2-yl]-phenyl}-acrylic acid |
| 52 | 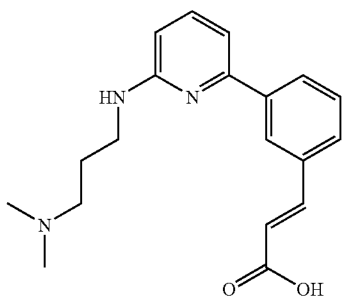 | (E)-3-{3-[6-(3-Dimethylamino-propylamino)-pyridin-2-yl]-phenyl}-acrylic acid |
| 53 | 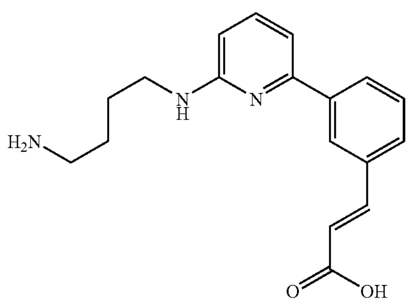 | (E)-3-{3-[6-(4-Amino-butylamino)-pyridin-2-yl]-phenyl}-acrylic acid |
| 54 | 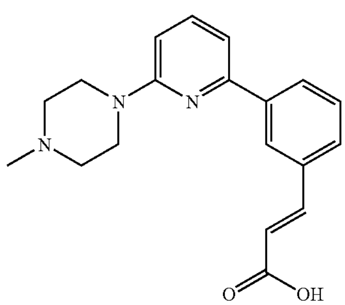 | (E)-3-{3-[6-(4-Methyl-piperazin-1-yl)-pyridin-2-yl]-phenyl}-acrylic acid |
| 55 | 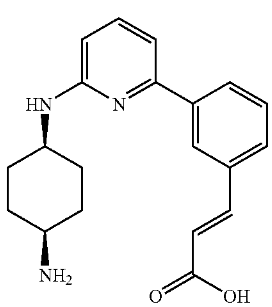 | (E)-3-{3-[6-(4-Amino-cyclohexylamino)-pyridin-2-yl]-phenyl}-acrylic acid |

TABLE I-continued
| Cpd # | Structure | name |
|---|---|---|
| 56 | 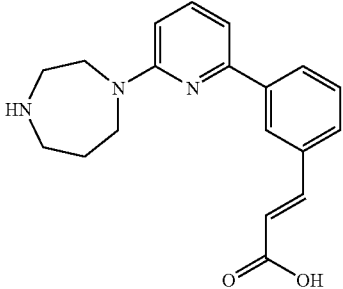 | (E)-3-[3-(6-[1,4]Diazepan-1-yl-pyridin-2-yl)-phenyl]-acrylic acid |
| 57 | 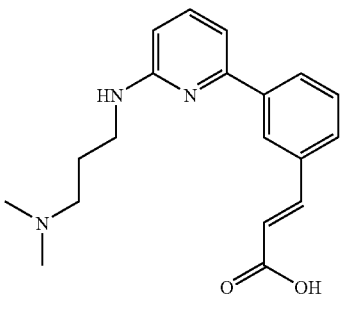 | (E)-3-{3-[6-(3-Dimethylamino-propylamino)-pyridin-2-yl]-phenyl}-acrylic acid |
| 58 | 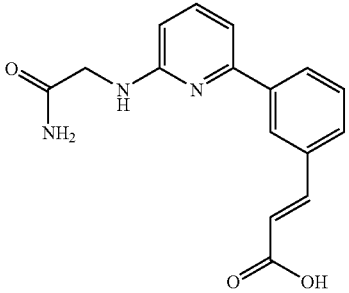 | (E)-3-{3-[6-(Carbamoylmethyl-amino)-pyridin-2-yl]-phenyl}-acrylic acid |
| 59 | 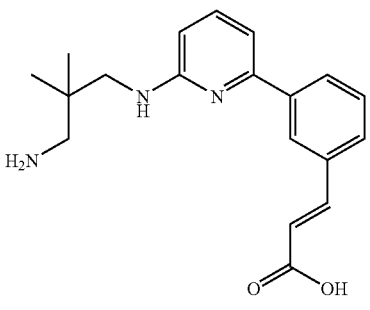 | (E)-3-{3-[6-(3-Amino-2,2-dimethyl-propylamino)-pyridin-2-yl]-phenyl}-acrylic acid |
| 60 | 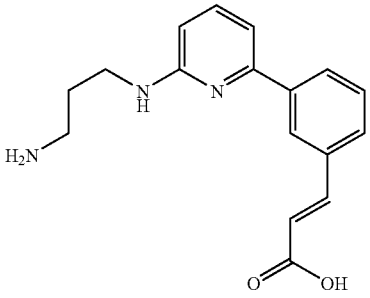 | (E)-3-{3-[6-(3-Amino-propylamino)-pyridin-2-yl]-phenyl}-acrylic acid |

TABLE I-continued

| Cpd # | Structure | name |
|---|---|---|
| 61 | 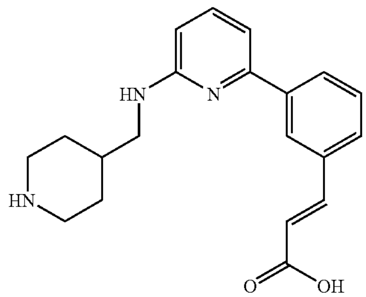 | (E)-3-(3-{6-[(Piperidin-4-ylmethyl)-amino]-pyridin-2-yl}-phenyl)-acrylic acid |
| 62 | 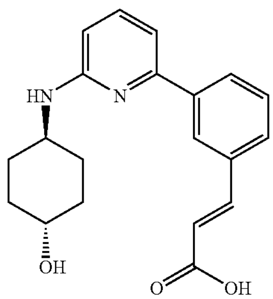 | (E)-3-{3-[6-(4-Hydroxy-cyclohexylamino)-pyridin-2-yl]-phenyl}-acrylic acid |
| 63 | 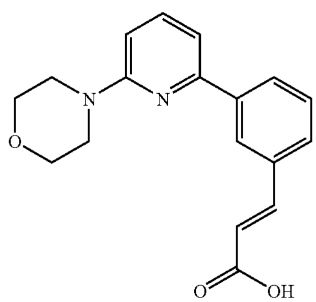 | (E)-3-[3-(6-Morpholin-4-yl-pyridin-2-yl)-phenyl]-acrylic acid |
| 64 | 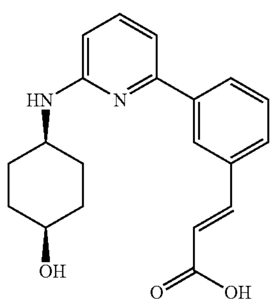 | (E)-3-{3-[6-(4-Hydroxy-cyclohexylamino)-pyridin-2-yl]-phenyl}-acrylic acid |
| 65 | 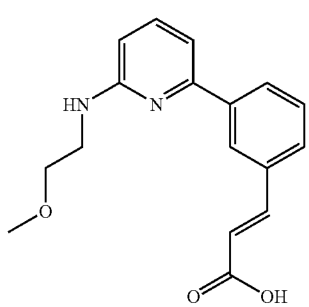 | (E)-3-{3-[6-(2-Methoxy-ethylamino)-pyridin-2-yl]-phenyl}-acrylic acid |

TABLE I-continued

| Cpd # | Structure | name |
|---|---|---|
| 66 | 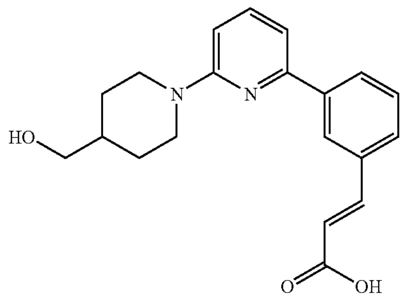 | (E)-3-[3-(4-Hydroxymethyl-3,4,5,6-tetrahydro-2H-[1,2']bipyridinyl-6'-yl)-phenyl]-acrylic acid |
| 67 | 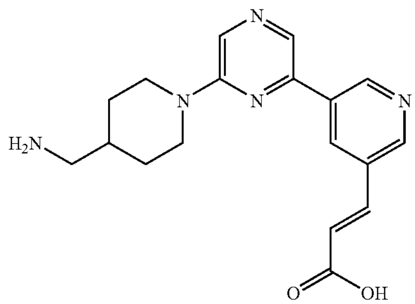 | (E)-3-{5-[6-(4-Aminomethyl-piperidin-1-yl)-pyrazin-2-yl]-pyridin-3-yl}-acrylic acid |
| 68 | 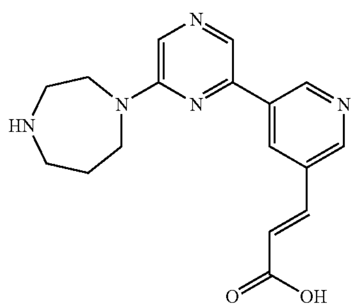 | (E)-3-[5-(6-[1,4]Diazepan-1-yl)-pyrazin-2-yl)-pyridin-3-yl]-acrylic acid |
| 69 | 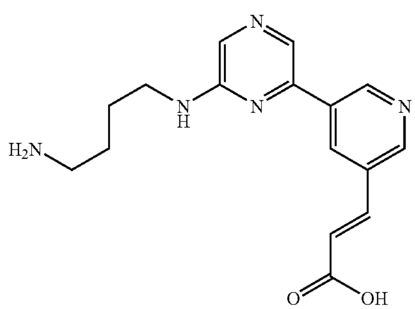 | (E)-3-{5-[6-(4-Amino-butylamino)-pyrazin-2-yl]-pyridin-3-yl}-acrylic acid |
| 70 | 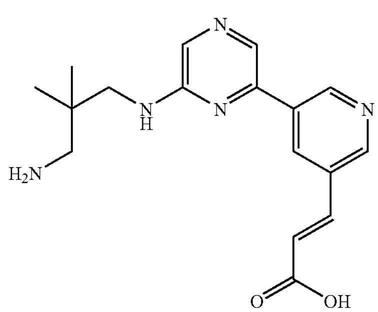 | (E)-3-{5-[6-(3-Amino-2,2-dimethyl-propylamino)-pyrazin-2-yl]-pyridin-3-yl}-acrylic acid |

TABLE I-continued

| Cpd # | Structure | name |
|---|---|---|
| 71 | 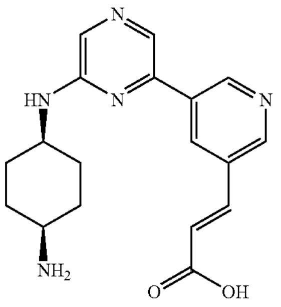 | (E)-3-{5-[6-(4-Amino-cyclohexylamino)-pyrazin-2-yl]-pyridin-3-yl}-acrylic acid |
| 72 | 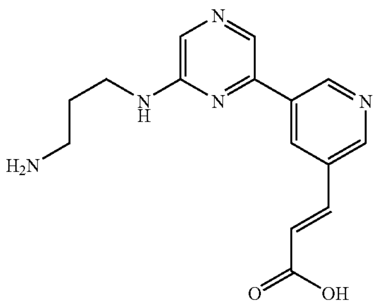 | (E)-3-{5-[6-(3-Amino-propylamino)-pyrazin-2-yl]-pyridin-3-yl}-acrylic acid |
| 73 | 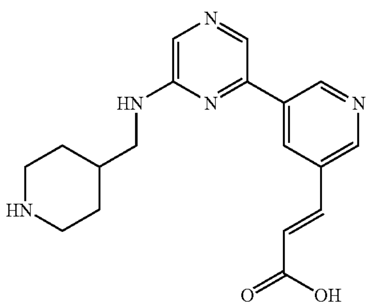 | (E)-3-(5-{6-[(Piperidin-4-ylmethyl)-amino]-pyrazin-2-yl}-pyridin-3-yl)-acrylic acid |
| 74 | 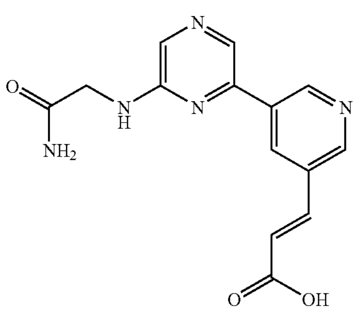 | (E)-3-{5-[6-(Carbamoylmethyl-amino)-pyrazin-2-yl]-pyridin-3-yl}-acrylic acid |
| 75 | 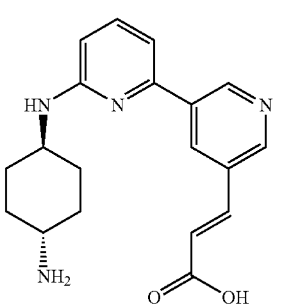 | (E)-3-[6-(4-Amino-cyclohexylamino)-[2,3']bipyridinyl-5'-yl]-acrylic acid |

TABLE I-continued

| Cpd # | Structure | name |
|---|---|---|
| 76 | 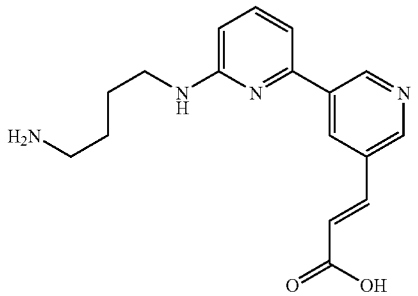 | (E)-3-[6-(4-Amino-butylamino)-[2,3']bipyridinyl-5'-yl]-acrylic acid |
| 77 | 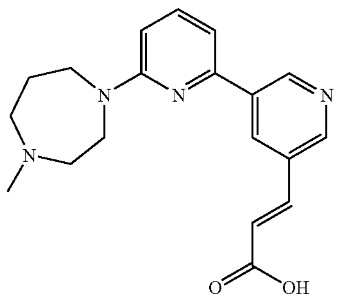 | (E)-3-[6-(4-Methyl-[1,4]diazepan-1-yl)-[2,3']bipyridinyl-5'-yl]-acrylic acid |
| 78 | 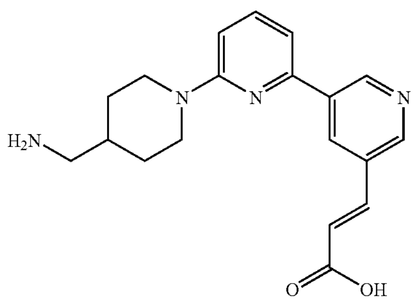 | (E)-3-(4-Aminomethyl-3,4,5,6-tetrahydro-2H-[1,2';6',3'']terpyridin-5''-yl)-acrylic acid |
| 79 | 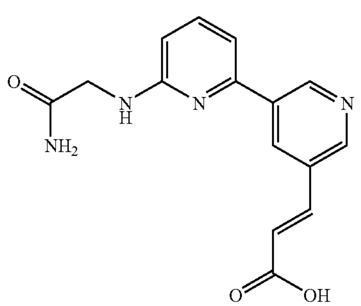 | (E)-3-[6-(Carbamoylmethyl-amino)-[2,3']bipyridinyl-5'-yl]-acrylic acid |
| 80 | 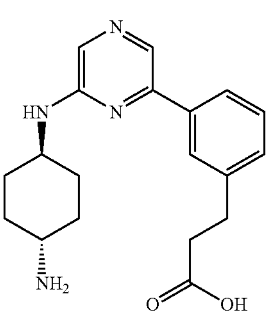 | 3-{3-[6-(4-Amino-cyclohexylamino)-pyrazin-2-yl]-phenyl}-propionic acid |

TABLE I-continued

| Cpd # | Structure | name |
|---|---|---|
| 81 | 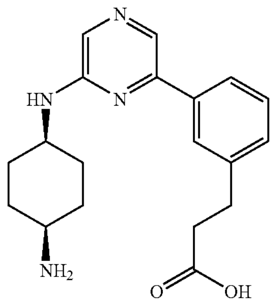 | 3-{3-[6-(4-Amino-cyclohexylamino)-pyrazin-2-yl]-phenyl}-propionic acid |
| 82 | 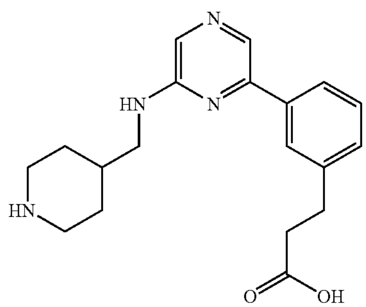 | 3-(3-{6-[(Piperidin-4-ylmethyl)-amino]-pyrazin-2-yl}-phenyl)-propionic acid |
| 83 | 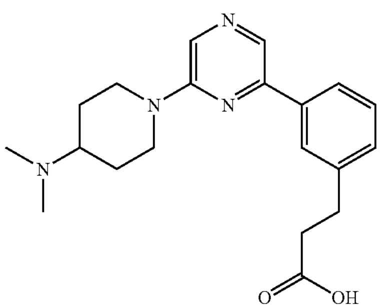 | 3-{3-[6-(4-Dimethylamino-piperidin-1-yl)-pyrazin-2-yl]-phenyl}-propionic acid |
| 84 | 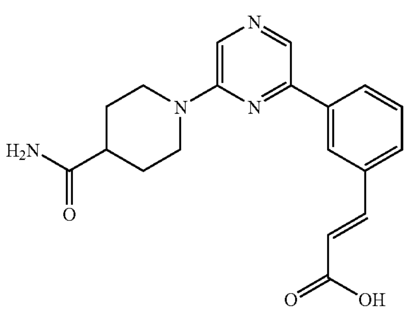 | (E)-3-{3-[6-(4-Carbamoyl-piperidin-1-yl)-pyrazin-2-yl]-phenyl}-acrylic acid |
| 85 | 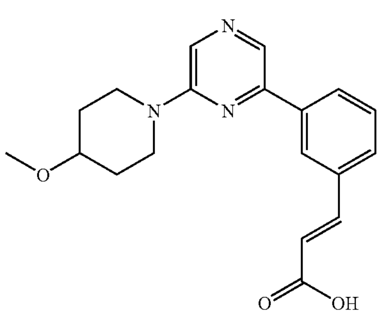 | (E)-3-{3-[6-(4-Methoxy-piperidin-1-yl)-pyrazin-2-yl]-phenyl}-acrylic acid |

TABLE I-continued

| Cpd # | Structure | name |
|---|---|---|
| 86 | 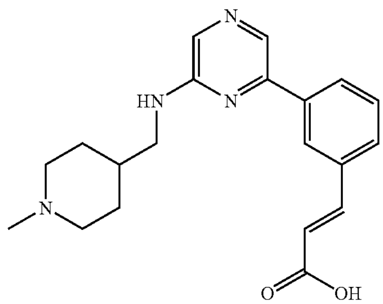 | (E)-3-(3-{6-[(1-Methyl-piperidin-4-ylmethyl)-amino]-pyrazin-2-yl}-phenyl)-acrylic acid |
| 87 | 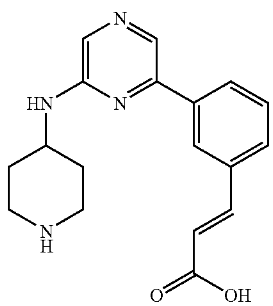 | (E)-3-{3-[6-(Piperidin-4-ylamino)-pyrazin-2-yl]-phenyl}-acrylic acid |
| 88 | 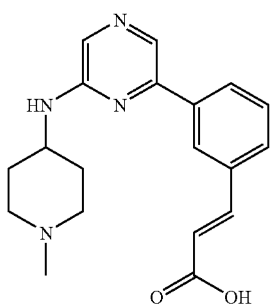 | (E)-3-{3-[6-(1-Methyl-piperidin-4-ylamino)-pyrazin-2-yl]-phenyl}-acrylic acid |
| 89 | 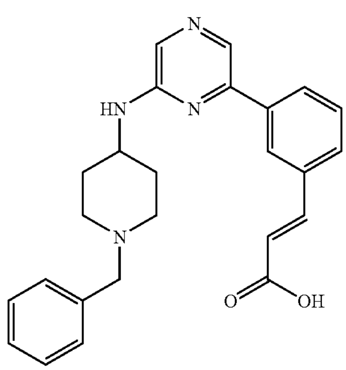 | (E)-3-{3-[6-(1-Benzyl-piperidin-4-ylamino)-pyrazin-2-yl]-phenyl}-acrylic acid |
| 90 | 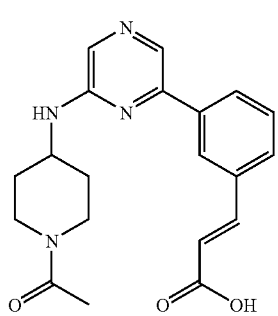 | (E)-3-{3-[6-(1-Acetyl-piperidin-4-ylamino)-pyrazin-2-yl]-phenyl}-acrylic acid |

TABLE I-continued

| Cpd # | Structure | name |
|---|---|---|
| 91 | 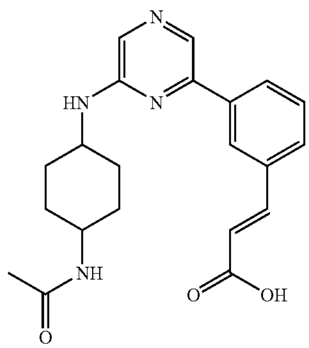 | (E)-3-{3-[6-(4-Acetylamino-cyclohexylamino)-pyrazin-2-yl]-phenyl}-acrylic acid |
| 92 | 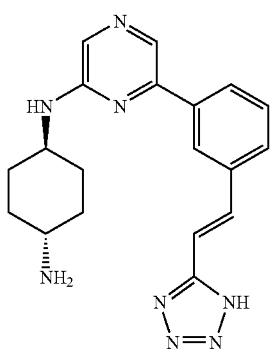 | N-(6-{3-[(E)-2-(1H-Tetrazol-5-yl)-vinyl]-phenyl}-pyrazin-2-yl)-cyclohexane-1,4-diamine |
| 93 | 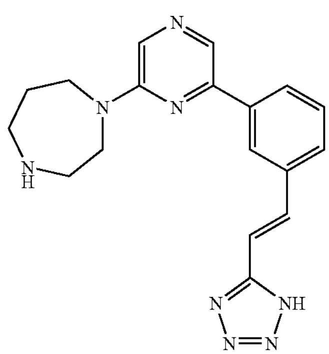 | 4-(6-{3-[(E)-2-(1H-tetrazol-5-yl)-vinyl]-phenyl}-pyrazin-2-yl)-[1,4]diazepane |
| 94 | 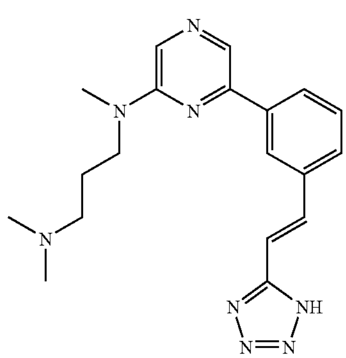 | N,N,N'-Trimethyl-N'-(6-{3-[(E)-2-(1H-tetrazol-5-yl)-vinyl]-phenyl}-pyrazin-2-yl)-propane-1,3-diamine |

TABLE I-continued

| Cpd # | Structure | name |
|---|---|---|
| 95 | 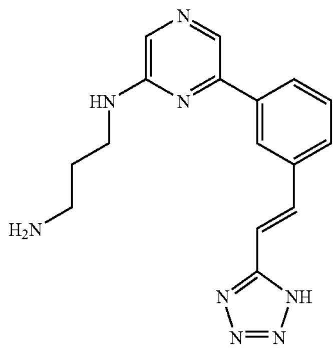 | N¹-(6-{3-[(E)-2-(1H-Tetrazol-5-yl)-vinyl]-phenyl}-pyrazin-2-yl)-propane-1,3-diamine |
| 96 | 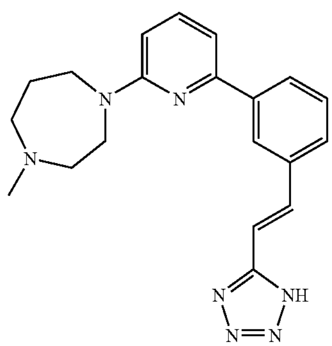 | 1-Methyl-4-(6-{3-[(E)-2-(1H-tetrazol-5-yl)-vinyl]-phenyl}-pyridin-2-yl)-perhydro-1,4-diazepine |
| 97 | 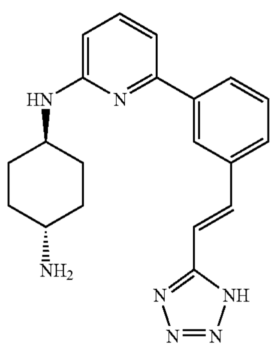 | N-(6-{3-[(E)-2-(1H-Tetrazol-5-yl)-vinyl]-phenyl}-pyridin-2-yl)-cyclohexane-1,4-diamine |
| 98 | | Piperidin-4-ylmethyl-(6-{3-[(E)-2-(1H-tetrazol-5-yl)-vinyl]-phenyl}-pyridin-2-yl)-amine | or the pharmaceutically acceptable salts and/or isomers thereof.

The following are compounds with $IC_{50}$ values

TABLE II
| Cpd # | Structure | name | IC$_{50}$ (nM) |
|---|---|---|---|
| 1 | 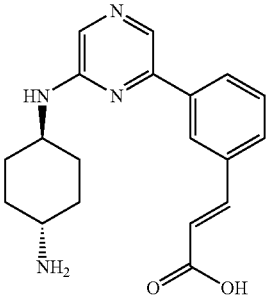 | (E)-3-{3-[6-(4-Amino-cyclohexylamino)-pyrazin-2-yl]-phenyl}-acrylic acid | 12 |
| 2 | 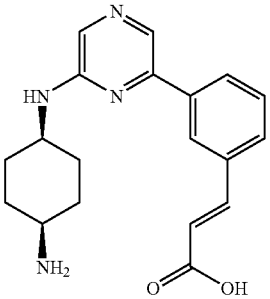 | (E)-3-{3-[6-(4-Amino-cyclohexylamino)-pyrazin-2-yl]-phenyl}-acrylic acid | 19 |
| 3 | 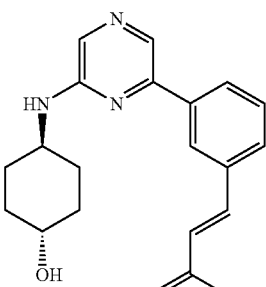 | (E)-3-{3-[6-(4-Hydroxy-cyclohexylamino)-pyrazin-2-yl]-phenyl}-acrylic acid | 265 |
| 4 | 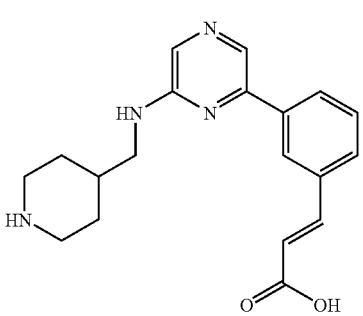 | (E)-3-(3-{6-[(Piperidin-4-ylmethyl)-amino]-pyrazin-2-yl}-phenyl)-acrylic acid | 57 |
| 5 | 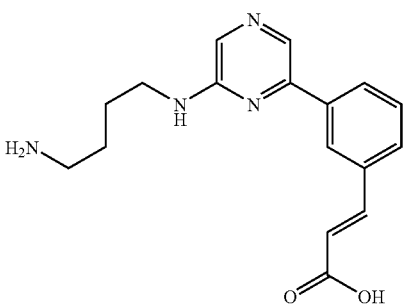 | (E)-3-{3-[6-(4-Amino-butylamino)-pyrazin-2-yl]-phenyl}-acrylic acid | 22 |

TABLE II-continued

| Cpd # | Structure | name | IC$_{50}$ (nM) |
|---|---|---|---|
| 6 | 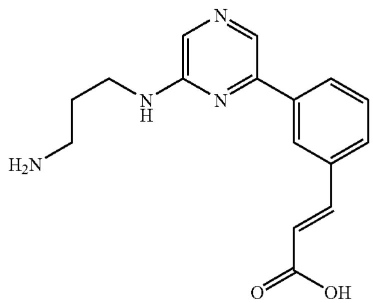 | (E)-3-{3-[6-(3-Amino-propylamino)-pyrazin-2-yl]-phenyl}-acrylic acid | 27 |
| 7 | 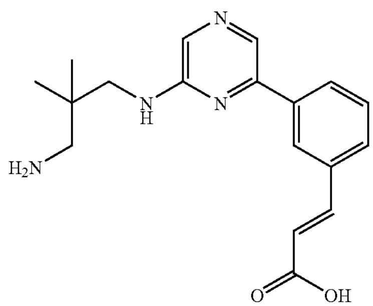 | (E)-3-{3-[6-(3-Amino-2,2-dimethyl-propylamino)-pyrazin-2-yl]-phenyl}-acrylic acid | 27 |
| 8 | 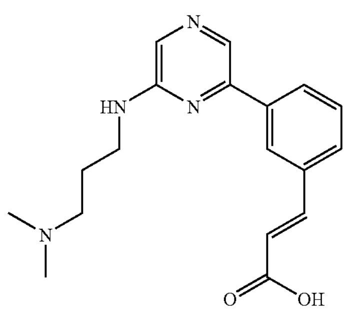 | (E)-3-{3-[6-(3-Dimethylamino-propylamino)-pyrazin-2-yl]-phenyl}-acrylic acid | 94 |
| 9 | 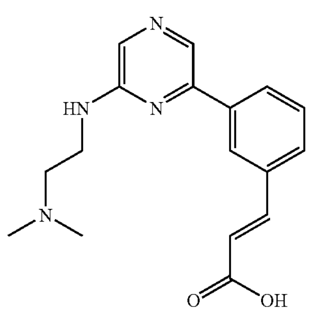 | (E)-3-{3-[6-(2-Dimethylamino-ethylamino)-pyrazin-2-yl]-phenyl}-acrylic acid | 99 |
| 10 | 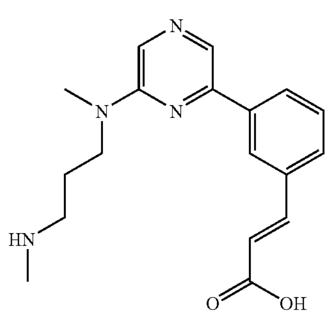 | (E)-3-(3-{6-[Methyl-(3-methylamino-propyl)-amino]-pyrazin-2-yl}-phenyl)-acrylic acid | 110 |

TABLE II-continued

| Cpd # | Structure | name | IC$_{50}$ (nM) |
|---|---|---|---|
| 11 | 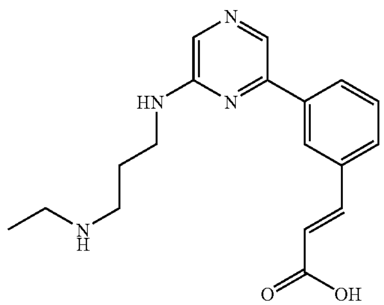 | (E)-3-{3-[6-(3-Ethylamino-propylamino)-pyrazin-2-yl]-phenyl}-acrylic acid | 120 |
| 12 | 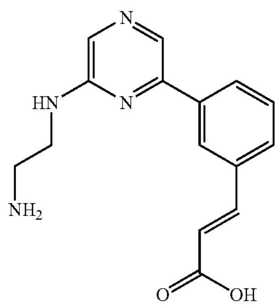 | (E)-3-{3-[6-(2-Amino-ethylamino)-pyrazin-2-yl]-phenyl}-acrylic acid | 140 |
| 13 | 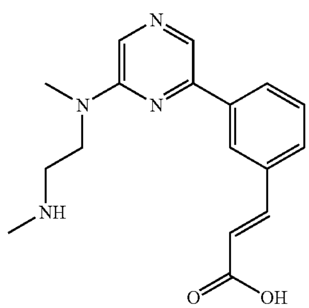 | (E)-3-(3-{6-[Methyl-(2-methylamino-ethyl)-amino]-pyrazin-2-yl}-phenyl)-acrylic acid | 240 |
| 14 | 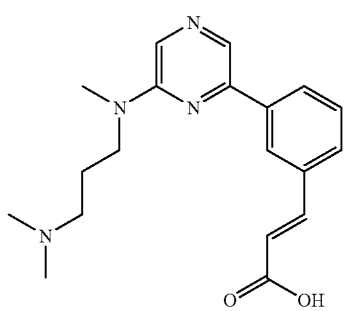 | (E)-3-(3-{6-[(3-Dimethylamino-propyl)-methyl-amino]-pyrazin-2-yl}-phenyl)-acrylic acid | 370 |
| 15 | 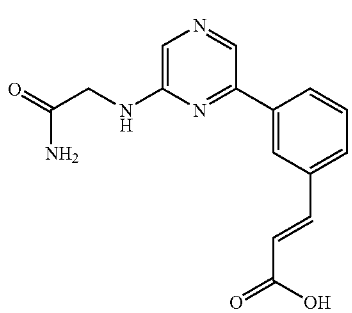 | (E)-3-{3-[6-(Carbamoylmethyl-amino)-pyrazin-2-yl]-phenyl}-acrylic acid | 84 |

TABLE II-continued

| Cpd # | Structure | name | IC$_{50}$ (nM) |
|---|---|---|---|
| 16 | 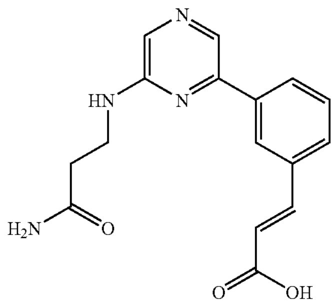 | (E)-3-{3-[6-(2-Carbamoyl-ethylamino)-pyrazin-2-yl]-phenyl}-acrylic acid; MS, electrospray | 250 |
| 17 | 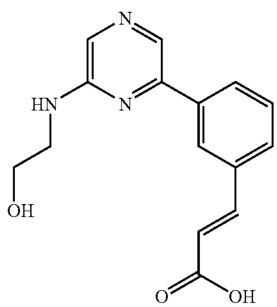 | (E)-3-{3-[6-(2-Hydroxy-ethylamino)-pyrazin-2-yl]-phenyl}-acrylic acid | 300 |
| 18 | 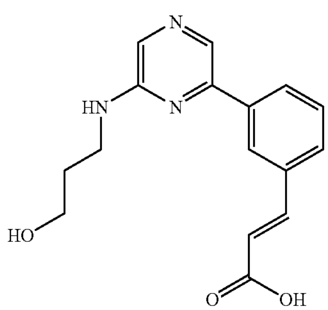 | E)-3-{3-[6-(3-Hydroxy-propylamino)-pyrazin-2-yl]-phenyl}-acrylic acid | 310 |
| 19 | 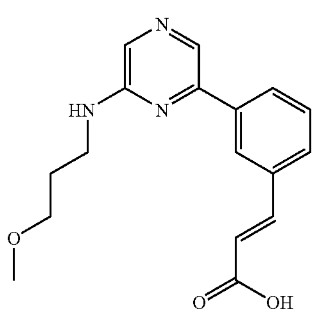 | (E)-3-{3-[6-(3-Methoxy-propylamino)-pyrazin-2-yl]-phenyl}-acrylic acid | 480 |
| 20 | 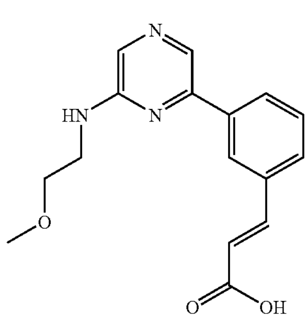 | (E)-3-{3-[6-(2-Methoxy-ethylamino)-pyrazin-2-yl]-phenyl}-acrylic acid | 1200 |

TABLE II-continued

| Cpd # | Structure | name | IC$_{50}$ (nM) |
|---|---|---|---|
| 21 | 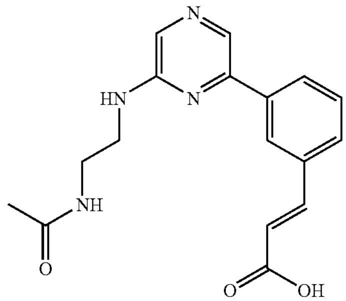 | (E)-3-{3-[6-(2-Acetylamino-ethylamino)-pyrazin-2-yl]-phenyl}-acrylic acid | 1020 |
| 22 | 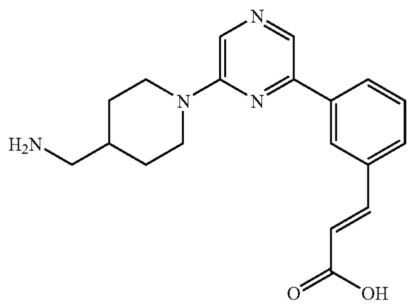 | (E)-3-{3-[6-(4-Aminomethyl-piperidin-1-yl)-pyrazin-2-yl]-phenyl}-acrylic acid | 21 |
| 23 | 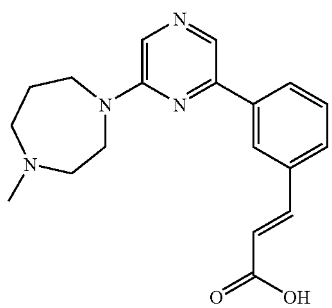 | (E)-3-{3-[6-(4-Methyl-[1,4]diazepan-1-yl)-pyrazin-2-yl]-phenyl}-acrylic acid | 41 |
| 24 | 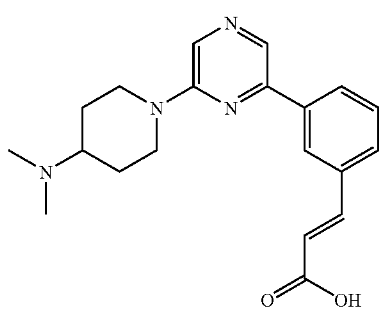 | (E)-3-{3-[6-(4-Dimethylamino-piperidin-1-yl)-pyrazin-2-yl]-phenyl}-acrylic acid | 72 |
| 25 | 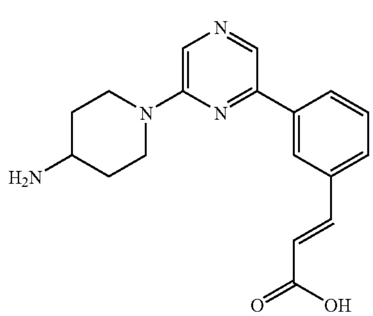 | Preparation of 14 (E)-3-{3-[6-(4-Amino-piperidin-1-yl)-pyrazin-2-yl]-phenyl}-acrylic acid | 115 |

| Cpd # | Structure | name | IC$_{50}$ (nM) |
|---|---|---|---|
| 26 | 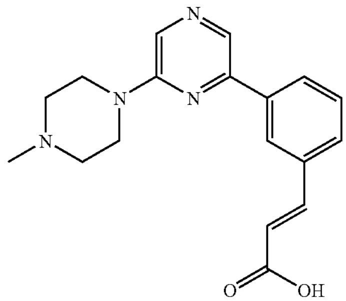 | (E)-3-[3-(4-Methyl-3,4,5,6-tetrahydro-2H-[1,2']bipyrazinyl-6'-yl)-phenyl]-acrylic acid | 150 |
| 27 | 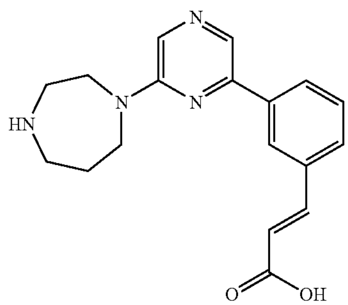 | (E)-3-[3-(6-[1,4]Diazepan-1-yl-pyrazin-2-yl)-phenyl]-acrylic acid | 185 |
| 28 | 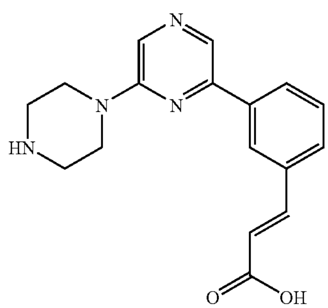 | (E)-3-[3-(3,4,5,6-Tetrahydro-2H-[1,2']bipyrazinyl-6'-yl)-phenyl]-acrylic acid | 200 |
| 29 | 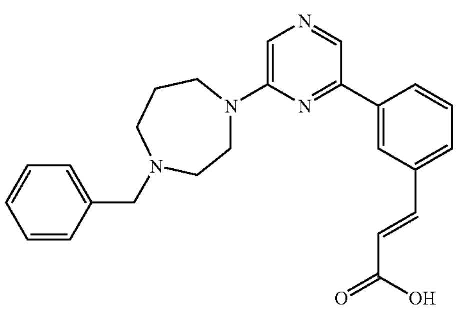 | (E)-3-{3-[6-(4-Benzyl-[1,4]diazepan-1-yl)-pyrazin-2-yl]-phenyl}-acrylic acid | 230 |
| 30 | 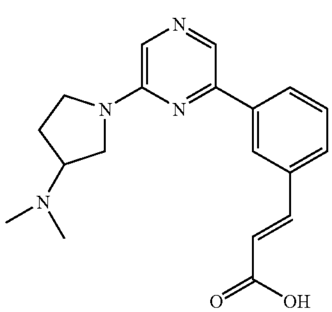 | (E)-3-{3-[6-(3-Dimethylamino-pyrrolidin-1-yl)-pyrazin-2-yl]-phenyl}-acrylic acid | 270 |

TABLE II-continued

| Cpd # | Structure | name | IC₅₀ (nM) |
|---|---|---|---|
| 31 | 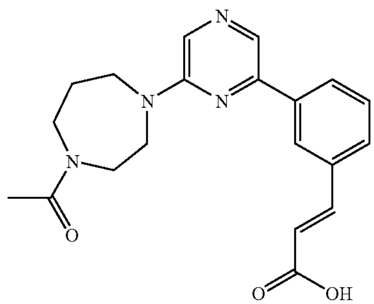 | (E)-3-{3-[6-(4-Acetyl-[1,4]diazepan-1-yl)-pyrazin-2-yl]-phenyl}-acrylic acid | 880 |
| 32 | 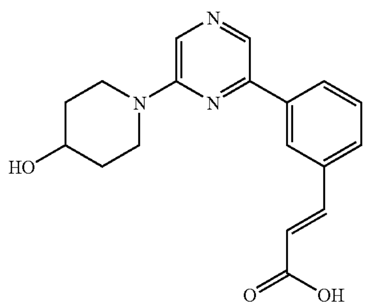 | (E)-3-{3-[6-(4-Hydroxy-piperidin-1-yl)-pyrazin-2-yl]-phenyl}-acrylic acid | 1050 |
| 33 | 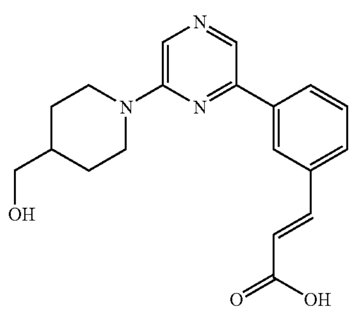 | (E)-3-{3-[6-(4-Hydroxymethyl-piperidin-1-yl)-pyrazin-2-yl]-phenyl}-acrylic acid | 2100 |
| 34 | 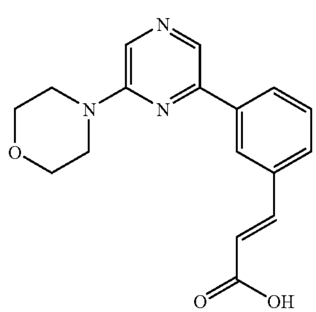 | (E)-3-[3-(6-Morpholin-4-yl-pyrazin-2-yl)-phenyl]-acrylic acid | 1700 |
| 35 | 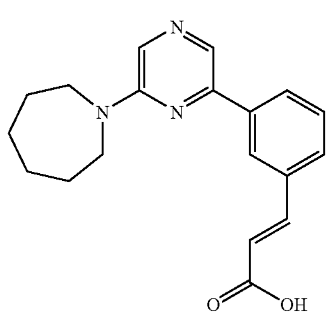 | (E)-3-[3-(6-Azepan-1-yl-pyrazin-2-yl)-phenyl]-acrylic acid | 3300 |

TABLE II-continued
| Cpd # | Structure | name | IC$_{50}$ (nM) |
|---|---|---|---|
| 36 | 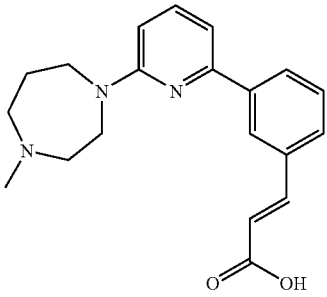 | (E)-3-{3-[6-(4-Methyl-[1,4]diazepan-1-yl)-pyridin-2-yl]-phenyl}-acrylic acid | 46 |
| 37 | 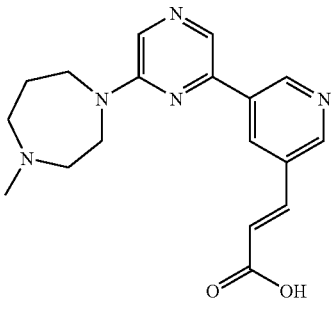 | (E)-3-{5-[6-(4-Methyl-[1,4]diazepan-1-yl)-pyrazin-2-yl]-pyridin-3-yl}-acrylic acid | 385 |
| 38 | 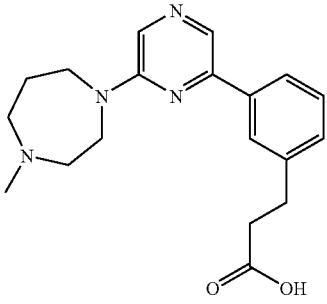 | 3-{3-[6-(4-Methyl-[1,4]diazepam-1-yl)-pyrazin-2-yl]-phenyl}-propionic acid | 1400 |
| 39 | 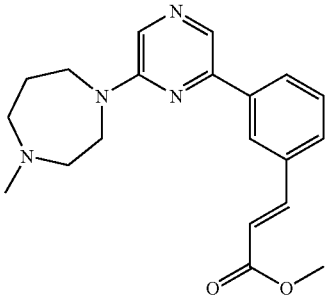 | (E)-3-{3-[6-(4-Methyl-[1,4]diazepan-1-yl)-pyrazin-2-yl]-phenyl}-acrylic acid methyl ester | 1400 |
| 40 | 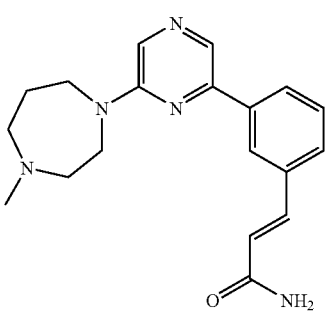 | (E)-3-{3-[6-(4-Methyl-[1,4]diazepan-1-yl)-pyrazin-2-yl]-phenyl}-acrylamide | 1200 |

TABLE II-continued

| Cpd # | Structure | name | IC$_{50}$ (nM) |
|---|---|---|---|
| 41 | 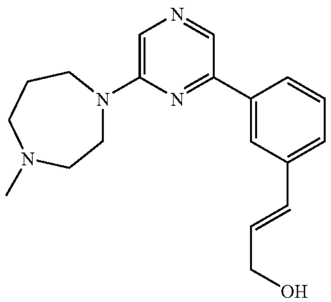 | (E)-3-{3-[6-(4-Methyl-[1,4]diazepan-1-yl)-pyrazin-2-yl]-phenyl}-prop-2-en-1-ol | 69POC @ 5 μg/mL |
| 42 | 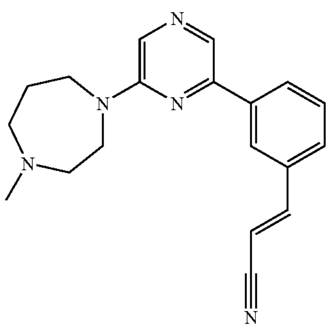 | (E)-3-{3-[6-(4-Methyl-[1,4]diazepan-1-yl)-pyrazin-2-yl]-phenyl}-acrylonitrile | 13000 |
| 43 | 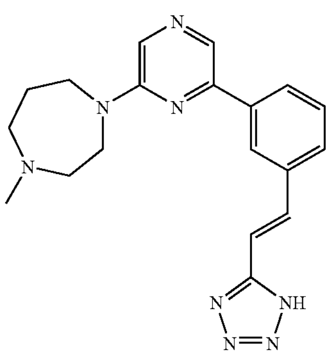 | 1-Methyl-4-(6-{3-[(E)-2-(1H-tetrazol-5-yl)-vinyl]-phenyl}-pyrazin-2-yl)-[1,4]diazepane | 89 |
| 44 | 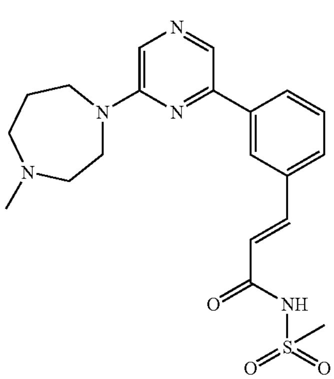 | N-((E)-3-{3-[6-(4-Methyl-perhydro-1,4-diazepin-1-yl)-pyrazin-2-yl]-phenyl}-acryloyl)-methanesulfonamide | 2400 |

TABLE II-continued

| Cpd # | Structure | name | IC$_{50}$ (nM) |
|---|---|---|---|
| 45 | | (E)-N-(2-Hydroxy-ethyl)-3-{3-[6-(4-methyl-perhydro-1,4-diazepin-1-yl)-pyrazin-2-yl]-phenyl}-acrylamide | 63 POC @ 3 µg/mL | or the pharmaceutically acceptable salts and/or isomers thereof.

In all the compounds disclosed hereinabove in this application, in the event the nomenclature is in conflict with the structure, it shall be understood that the compound is defined by the structure.

Of particular importance according to the invention are compounds of formula (I), for use as pharmaceutical compositions for the treatment of inflammatory diseases, such as Crohn's and Rheumatoid Arthritis and Cancer.

The invention also relates to the use of a compound of formula (I), for preparing a pharmaceutical composition for the treatment and/or prevention of inflammatory diseases, such as Crohn's and Rheumatoid Arthritis and Cancer.

The invention also relates to pharmaceutical preparations, containing as active substance one or more compounds of formula (I), or the pharmaceutically acceptable derivatives thereof, optionally combined with conventional excipients and/or carriers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

A. Chemical Nomenclature, Terms, and Conventions

In the groups, radicals, or moieties defined below, the number of carbon atoms is often specified preceding the group, for example, $C_1$-$C_{10}$ alkyl means an alkyl group or radical having 1 to 10 carbon atoms. The term "lower" applied to any carbon-containing group means a group containing from 1 to 8 carbon atoms, as appropriate to the group (i.e., a cyclic group must have at least 3 atoms to constitute a ring). In general, for groups comprising two or more subgroups, the last named group is the radical attachment point, for example, "alkylaryl" means a monovalent radical of the formula Alk-Ar-, while "arylalkyl" means a monovalent radical of the formula Ar-Alk- (where Alk is an alkyl group and Ar is an aryl group). Furthermore, the use of a term designating a monovalent radical where a divalent radical is appropriate shall be construed to designate the respective divalent radical and vice versa. Unless otherwise specified, conventional definitions of terms control and conventional stable atom valences are presumed and achieved in all formulas and groups.

The terms "alkyl" or "alkyl group" mean a branched or straight-chain saturated aliphatic hydrocarbon monovalent radical. This term is exemplified by groups such as methyl, ethyl, n-propyl, 1-methylethyl (isopropyl), n-butyl, n-pentyl, 1,1-dimethylethyl (tert-butyl), and the like. It may be abbreviated "Alk".

The term "heterocycloalkyl" means a stable non aromatic 5- to 14-membered, cyclic radical having from one to four heteroatoms in the ring(s) independently selected from nitrogen, oxygen, and sulfur, wherein any sulfur heteroatoms may optionally be oxidized and any nitrogen heteroatom may optionally be oxidized or be quaternized. Unless otherwise specified, the heterocycloalkylring may be attached at any suitable heteroatom or carbon atom which results in a stable structure and, if substituted, may be substituted at any suitable heteroatom or carbon atom which results in a stable structure.

The terms "alkylene" or "alkylene group" mean a branched or straight-chain saturated aliphatic hydrocarbon divalent radical having the specified number of carbon atoms. This term is exemplified by groups such as methylene, ethylene, propylene, n-butylene, and the like, and may alternatively and equivalently be denoted herein as -(alkyl)-.

The terms "alkoxy" or "alkoxy group" mean a monovalent radical of the formula AlkO-, where Alk is an alkyl group. This term is exemplified by groups such as methoxy, ethoxy, propoxy, isopropoxy, butoxy, sec-butoxy, tert-butoxy, pentoxy, and the like.

The terms "alkoxycarbonyl" or "alkoxycarbonyl group" mean a monovalent radical of the formula AlkO-C(O)—, where Alk is alkyl. Exemplary alkoxycarbonyl groups include methoxycarbonyl, ethoxycarbonyl, tert-butyloxycarbonyl, and the like.

The terms "alkylaminocarbonyloxy" or "alkylaminocarbonyloxy group" mean a monovalent radical of the formula AlkNHC(O)O—, where Alk is alkyl.

The terms "amino" or "amino group" mean an —NH$_2$ group.

The terms "alkylamino" or "alkylamino group" mean a monovalent radical of the formula (Alk)NH—, where Alk is alkyl. Exemplary alkylamino groups include methylamino, ethylamino, propylamino, butylamino, tert-butylamino, and the like.

The terms "dialkylamino" or "dialkylamino group" mean a monovalent radical of the formula (Alk)(Alk)N—, where each Alk is independently alkyl. Exemplary dialkylamino groups include dimethylamino, methylethylamino, diethylamino, dipropylamino, ethylpropylamino, and the like.

The terms "carboxamido" or "carboxamido group" mean a monovalent radical of the formula —CONH$_2$ The terms "halogen" or "halogen group" mean a fluoro, chloro, bromo, or iodo group.

The term "halo" means one or more hydrogen atoms of the group are replaced by halogen groups.

The terms "haloalkyl" or "haloalkyl group" mean a branched or straight-chain saturated aliphatic hydrocarbon monovalent radical, wherein one or more hydrogen atoms thereof are each independently replaced with halogen atoms. This term is exemplified by groups such as chloromethyl, 1,2-dibromoethyl, 1,1,1-trifluoropropyl, 2-iodobutyl, 1-chloro-2-bromo-3-fluoropentyl, and the like.

The terms "sulfanyl", "sulfanyl group", "thioether", or "thioether group" mean a divalent radical of the formula —S—.

The terms "alkylthio" or "alkylthio group" mean a monovalent radical of the formula AlkS-, where Alk is alkyl. Exemplary groups include methylthio, ethylthio, n-propylthio, isopropylthio, n-butylthio, and the like.

The terms "cycloalkyl" or "cycloalkyl group" mean a stable aliphatic saturated 3- to 15-membered monocyclic or polycyclic monovalent radical consisting solely of carbon and hydrogen atoms which may comprise one or more fused or bridged ring(s), preferably a 5- to 7-membered monocyclic or 7- to 10-membered bicyclic ring. Unless otherwise specified, the cycloalkyl ring may be attached at any carbon atom which results in a stable structure and, if substituted, may be substituted at any suitable carbon atom which results in a stable structure. Exemplary cycloalkyl groups include cyclopropyl, cyclobutyl, cyclopentyl, cyclohexyl, cycloheptyl, cyclooctyl, cyclononyl, cyclodecyl, norbornanyl, adamantyl, tetrahydronaphthyl (tetralin), 1-decalinyl, bicyclo[2.2.2]octanyl, 1-methylcyclopropyl, 2-methylcyclopentyl, 2-methylcyclooctyl, and the like.

The terms "aryl" or "aryl group" mean an aromatic carbocyclic monovalent or divalent radical of from 6 to 14 carbon atoms having a single ring (e.g., phenyl or phenylene) or multiple condensed rings (e.g., naphthyl or anthranyl). Unless otherwise specified, the aryl ring may be attached at any suitable carbon atom which results in a stable structure and, if substituted, may be substituted at any suitable carbon atom which results in a stable structure. Exemplary aryl groups include phenyl, naphthyl, anthryl, phenanthryl, indanyl, indenyl, biphenyl, and the like. It may be abbreviated "Ar".

The terms "heteroaryl" or "heteroaryl group" mean a stable aromatic 5- to 14-membered, monocyclic or polycyclic monovalent or divalent radical which may comprise one or more fused or bridged ring(s), preferably a 5- to 7-membered monocyclic or 7- to 10-membered bicyclic radical, having from one to four heteroatoms in the ring(s) independently selected from nitrogen, oxygen, and sulfur, wherein any sulfur heteroatoms may optionally be oxidized and any nitrogen heteroatom may optionally be oxidized or be quaternized. Unless otherwise specified, the heteroaryl ring may be attached at any suitable heteroatom or carbon atom which results in a stable structure and, if substituted, may be substituted at any suitable heteroatom or carbon atom which results in a stable structure. Exemplary and preferred heteroaryls include furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, triazinyl, indolizinyl, azaindolizinyl, indolyl, azaindolyl, diazaindolyl, dihydroindolyl, dihydroazaindoyl, isoindolyl, azaisoindolyl, benzofuranyl, furanopyridinyl, furanopyrimidinyl, furanopyrazinyl, furanopyridazinyl, dihydrobenzofuranyl, dihydrofuranopyridinyl, dihydrofuranopyrimidinyl, benzodioxolanyl, benzothienyl, thienopyridinyl, thienopyrimidinyl, thienopyrazinyl, thienopyridazinyl, dihydrobenzothienyl, dihydrothienopyridinyl, dihydrothienopyrimidinyl, indazolyl, azaindazolyl, diazaindazolyl, benzimidazolyl, imidazopyridinyl, benzthiazolyl, thiazolopyridinyl, thiazolopyrimidinyl, benzoxazolyl, oxazolopyridinyl, oxazolopyrimidinyl, benzisoxazolyl, purinyl, chromanyl, azachromanyl, quinolizinyl, quinolinyl, dihydroquinolinyl, tetrahydroquinolinyl, isoquinolinyl, dihydroisoquinolinyl, tetrahydroisoquinolinyl, cinnolinyl, azacinnolinyl, phthalazinyl, azaphthalazinyl, quinazolinyl, azaquinazolinyl, quinoxalinyl, azaquinoxalinyl, naphthyridinyl, dihydronaphthyridinyl, tetrahydronaphthyridinyl, pteridinyl, carbazolyl, acridinyl, phenazinyl, phenothiazinyl, and phenoxazinyl, and the like.

The term "compounds of the invention" and equivalent expressions are meant to embrace compounds of Formula (I) as herein described, including the tautomers, the prodrugs, the salts, particularly the pharmaceutically acceptable salts, and the solvates and hydrates thereof, where the context so permits. In general and preferably, the compounds of the invention and the formulas designating the compounds of the invention are understood to only include the stable compounds thereof and exclude unstable compounds, even if an unstable compound might be considered to be literally embraced by the compound formula. Similarly, reference to intermediates, whether or not they themselves are claimed, is meant to embrace their salts and solvates, where the context so permits. For the sake of clarity, particular instances when the context so permits are sometimes indicated in the text, but these instances are purely illustrative and it is not intended to exclude other instances when the context so permits.

The terms "optional" or "optionally" mean that the subsequently described event or circumstances may or may not occur, and that the description includes instances where the event or circumstance occurs and instances in which it does not. For example, "optionally substituted aryl" means that the aryl radical may or may not be substituted and that the description includes both substituted aryl radicals and aryl radicals having no substitution.

The terms "stable compound" or "stable structure" mean a compound that is sufficiently robust to survive isolation to a useful degree of purity from a reaction mixture, and formulation into an efficacious therapeutic or diagnostic agent. For example, a compound which would have a "dangling valency" or is a carbanion is not a compound contemplated by the invention.

The term "substituted" means that any one or more hydrogens on an atom of a group or moiety, whether specifically designated or not, is replaced with a selection from the indicated group of substituents, provided that the atom's normal valency is not exceeded and that the substitution results in a stable compound. If a bond to a substituent is shown to cross the bond connecting two atoms in a ring, then such substituent may be bonded to any atom on the ring. When a substituent is listed without indicating the atom via which such substituent is bonded to the rest of the compound, then such substituent may be bonded via any atom in such substituent. For example, when the substituent is piperazinyl, piperidinyl, or tetrazolyl, unless specified otherwise, such piperazinyl, piperidinyl, or tetrazolyl group may be bonded to the rest of the compound of the invention via any atom in such piperazinyl, piperidinyl, or tetrazolyl group. Generally, when any substituent or group occurs more than one time in any constituent or compound, its definition on each occurrence is independent of its definition at every other occurrence. Thus, for example, if a group is shown to be substituted with 0 to 2 $R^5$, then such group is optionally substituted with up to two $R^5$ groups and $R^5$ at each occurrence is selected independently from the defined list of possible $R^5$. Such combinations of substituents and/or variables, however, are permissible only if such combinations result in stable compounds.

In a specific embodiment, the term "about" or "approximately" means within 20%, preferably within 10%, and more preferably within 5% of a given value or range.

The yield of each of the reactions described herein is expressed as a percentage of the theoretical yield.

C. Isomer Terms and Conventions

The term "isomers" means compounds having the same number and kind of atoms, and hence the same molecular weight, but differing with respect to the arrangement or configuration of the atoms in space. The term includes stereoisomers and geometric isomers.

The terms "stereoisomer" or "optical isomer" mean a stable isomer that has at least one chiral atom or restricted rotation giving rise to perpendicular dissymmetric planes (e.g., certain biphenyls, allenes, and spiro compounds) and can rotate plane-polarized light. Because asymmetric centers and other chemical structure exist in the compounds of the invention which may give rise to stereoisomerism, the invention contemplates stereoisomers and mixtures thereof. The compounds of the invention and their salts include asymmetric carbon atoms and may therefore exist as single stereoisomers, racemates, and as mixtures of enantiomers and diastereomers. Typically, such compounds will be prepared as a racemic mixture. If desired, however, such compounds can be prepared or isolated as pure stereoisomers, i.e., as individual enantiomers or diastereomers, or as stereoisomer-enriched mixtures. As discussed in more detail below, individual stereoisomers of compounds are prepared by synthesis from optically active starting materials containing the desired chiral centers or by preparation of mixtures of enantiomeric products followed by separation or resolution, such as conversion to a mixture of diastereomers followed by separation or recrystallization, chromatographic techniques, use of chiral resolving agents, or direct separation of the enantiomers on chiral chromatographic columns. Starting compounds of particular stereochemistry are either commercially available or are made by the methods described below and resolved by techniques well-known in the art.

The term "enantiomers" means a pair of stereoisomers that are non-superimposable mirror images of each other.

The terms "diastereoisomers" or "diastereomers" mean optical isomers which are not mirror images of each other.

The terms "racemic mixture" or "racemate" mean a mixture containing equal parts of individual enantiomers.

The term "non-racemic mixture" means a mixture containing unequal parts of individual enantiomers.

The term "geometrical isomer" means a stable isomer which results from restricted freedom of rotation about double bonds (e.g., cis-2-butene and trans-2-butene) or in a cyclic structure (e.g., cis-1,3-dichlorocyclobutane and trans-1,3-dichlorocyclobutane). Because carbon-carbon double (olefinic) bonds, C=N double bonds, cyclic structures, and the like may be present in the compounds of the invention, the invention contemplates each of the various stable geometric isomers and mixtures thereof resulting from the arrangement of substituents around these double bonds and in these cyclic structures. The substituents and the isomers are designated using the cis/trans convention or using the E or Z system, wherein the term "E" means higher order substituents on opposite sides of the double bond, and the term "Z" means higher order substituents on the same side of the double bond. A thorough discussion of E and Z isomerism is provided in J. March, *Advanced Organic Chemistry: Reactions, Mechanisms, and Structure,* 4th ed., John Wiley & Sons, 1992, which is hereby incorporated by reference in its entirety. Several of the following examples represent single E isomers, single Z isomers, and mixtures of E/Z isomers. Determination of the E and Z isomers can be done by analytical methods such as x-ray crystallography, $^1$H NMR, and $^{13}$C NMR.

Some of the compounds of the invention can exist in more than one tautomeric form. As mentioned above, the compounds of the invention include all such tautomers.

It is well-known in the art that the biological and pharmacological activity of a compound is sensitive to the stereochemistry of the compound. Thus, for example, enantiomers often exhibit strikingly different biological activity including differences in pharmacokinetic properties, including metabolism, protein binding, and the like, and pharmacological properties, including the type of activity displayed, the degree of activity, toxicity, and the like. Thus, one skilled in the art will appreciate that one enantiomer may be more active or may exhibit beneficial effects when enriched relative to the other enantiomer or when separated from the other enantiomer. Additionally, one skilled in the art would know how to separate, enrich, or selectively prepare the enantiomers of the compounds of the invention from this disclosure and the knowledge of the prior art.

Thus, although the racemic form of drug may be used, it is often less effective than administering an equal amount of enantiomerically pure drug; indeed, in some cases, one enantiomer may be pharmacologically inactive and would merely serve as a simple diluent. For example, although ibuprofen had been previously administered as a racemate, it has been shown that only the S-isomer of ibuprofen is effective as an anti-inflammatory agent (in the case of ibuprofen, however, although the R-isomer is inactive, it is converted in vivo to the S-isomer, thus, the rapidity of action of the racemic form of the drug is less than that of the pure S-isomer). Furthermore, the pharmacological activities of enantiomers may have distinct biological activity. For example, S-penicillamine is a therapeutic agent for chronic arthritis, while R-penicillamine is toxic. Indeed, some purified enantiomers have advantages over the racemates, as it has been reported that purified individual isomers have faster transdermal penetration rates compared to the racemic mixture. See U.S. Pat. Nos. 5,114,946 and 4,818,541.

Thus, if one enantiomer is pharmacologically more active, less toxic, or has a preferred disposition in the body than the other enantiomer, it would be therapeutically more beneficial to administer that enantiomer preferentially. In this way, the patient undergoing treatment would be exposed to a lower total dose of the drug and to a lower dose of an enantiomer that is possibly toxic or an inhibitor of the other enantiomer.

Preparation of Pure Enantiomers or Mixtures of Desired Enantiomeric Excess (Ee) or enantiomeric purity are accomplished by one or more of the many methods of (a) separation or resolution of enantiomers, or (b) enantioselective synthesis known to those of skill in the art, or a combination thereof. These resolution methods generally rely on chiral recognition and include, for example, chromatography using chiral stationary phases, enantioselective host-guest complexation, resolution or synthesis using chiral auxiliaries, enantioselective synthesis, enzymatic and nonenzymatic kinetic resolution, or spontaneous enantioselective crystallization. Such methods are disclosed generally in *Chiral Separation Techniques: A Practical Approach* (2nd Ed.), G. Subramanian (ed.), Wiley-VCH, 2000; T. E. Beesley and R. P. W. Scott, *Chiral Chromatography*, John Wiley & Sons, 1999; and Satinder Ahuja, *Chiral Separations by Chromatography*, Am. Chem. Soc., 2000. Furthermore, there are equally well-known methods for the quantitation of enantiomeric excess or purity, for example, GC, HPLC, CE, or NMR, and assignment of absolute configuration and conformation, for example, CD ORD, X-ray crystallography, or NMR.

In general, all tautomeric forms and isomeric forms and mixtures, whether individual geometric isomers or stereoisomers or racemic or non-racemic mixtures, of a chemical structure or compound is intended, unless the specific stereochemistry or isomeric form is specifically indicated in the compound name or structure.

D. Pharmaceutical Administration and Diagnostic and Treatment Terms and Conventions The term "patient" includes both human and non-human mammals.

The term "effective amount" means an amount of a compound according to the invention which, in the context of which it is administered or used, is sufficient to achieve the desired effect or result. Depending on the context, the term effective amount may include or be synonymous with a pharmaceutically effective amount or a diagnostically effective amount.

The terms "pharmaceutically effective amount" or "therapeutically effective amount" means an amount of a compound according to the invention which, when administered to a patient in need thereof, is sufficient to effect treatment for disease-states, conditions, or disorders for which the compounds have utility. Such an amount would be sufficient to elicit the biological or medical response of a tissue, system, or patient that is sought by a researcher or clinician. The amount of a compound of according to the invention which constitutes a therapeutically effective amount will vary depending on such factors as the compound and its biological activity, the composition used for administration, the time of administration, the route of administration, the rate of excretion of the compound, the duration of treatment, the type of disease-state or disorder being treated and its severity, drugs used in combination with or coincidentally with the compounds of the invention, and the age, body weight, general health, sex, and diet of the patient. Such a therapeutically effective amount can be determined routinely by one of ordinary skill in the art having regard to their own knowledge, the prior art, and this disclosure.

The term "diagnostically effective amount" means an amount of a compound according to the invention which, when used in a diagnostic method, apparatus, or assay, is sufficient to achieve the desired diagnostic effect or the desired biological activity necessary for the diagnostic method, apparatus, or assay. Such an amount would be sufficient to elicit the biological or medical response in a diagnostic method, apparatus, or assay, which may include a biological or medical response in a patient or in a in vitro or in vivo tissue or system, that is sought by a researcher or clinician. The amount of a compound according to the invention which constitutes a diagnostically effective amount will vary depending on such factors as the compound and its biological activity, the diagnostic method, apparatus, or assay used, the composition used for administration, the time of administration, the route of administration, the rate of excretion of the compound, the duration of administration, drugs and other compounds used in combination with or coincidentally with the compounds of the invention, and, if a patient is the subject of the diagnostic administration, the age, body weight, general health, sex, and diet of the patient. Such a diagnostically effective amount can be determined routinely by one of ordinary skill in the art having regard to their own knowledge, the prior art, and this disclosure.

The terms "treating" or "treatment" mean the treatment of a disease-state in a patient, and include:

(i) preventing the disease-state from occurring in a patient, in particular, when such patient is genetically or otherwise predisposed to the disease-state but has not yet been diagnosed as having it;

(ii) inhibiting or ameliorating the disease-state in a patient, i.e., arresting or slowing its development; or (iii) relieving the disease-state in a patient, i.e., causing regression or cure of the disease.

General Synthetic Methods

The compounds of the invention may be prepared by the general methods and examples presented below, and methods known to those of ordinary skill in the art. Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. In the schemes below, unless otherwise specified, X, Y, $R_1$, $R_2$ and $R_3$ in the formulas shown below shall have the meanings defined for these groups in the definition of the formula I of the invention, described hereinabove. Intermediates used in the syntheses below are either commercially available or easily prepared by methods known to those skilled in the art. Reaction progress may be monitored by conventional methods such as thin layer chromatography (TLC) or high pressure liquid chromatography-mass spec (HPLC-MS). Intermediates and products may be purified by methods known in the art, including column chromatography, HPLC, preparative TLC or recrystallization.

Scheme 1

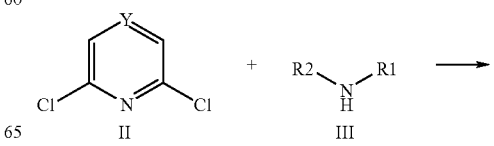

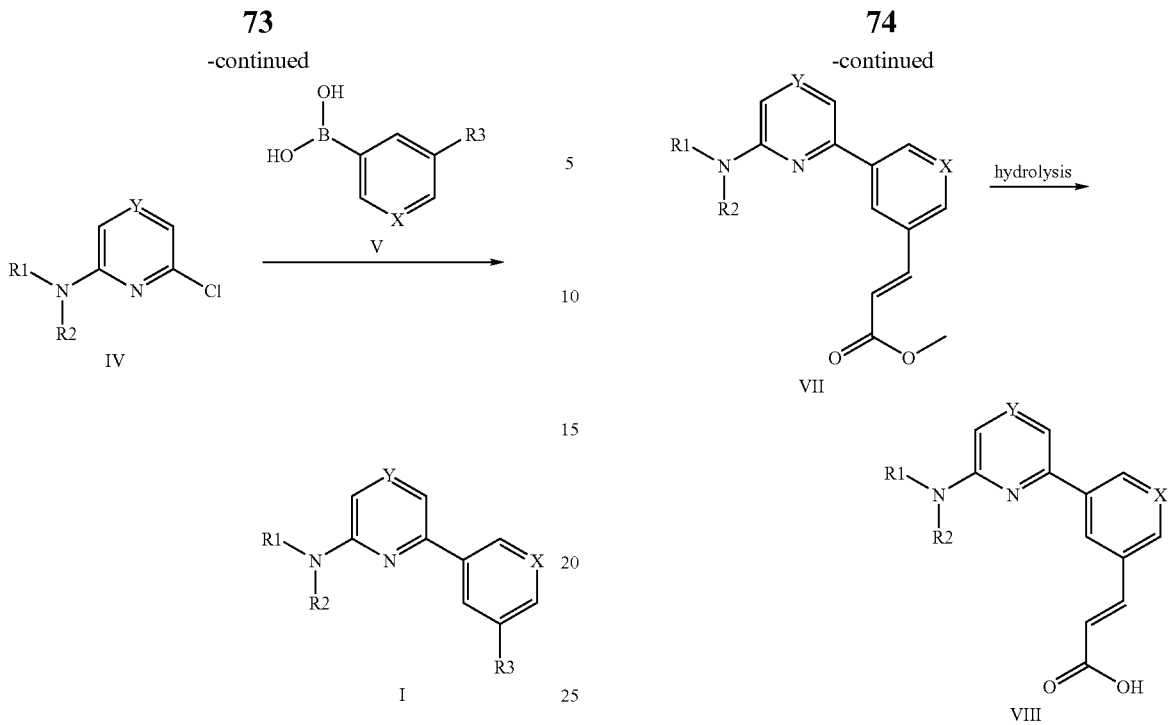

As illustrated in scheme 1 (X=C, Y=N, C), 2,6-dichloropyrazine (II) is combined with an amine in a suitable solvent. The amine may be used in excess or an additional basic reagent may be utilized. The product (IV) is then treated with a reagent such as V and additional reagents as required for the Suzuki coupling reaction to provide the desired product (I). Modification of R₁ or R₂, such as protection/deprotection by methods known in the art and methods illustrated in the Synthetic Examples section can provide additional desired compounds of formula I.

An alternate approach that may be used to prepare compounds of formula I (X=C, Y=N, C) is illustrated in Scheme 2.

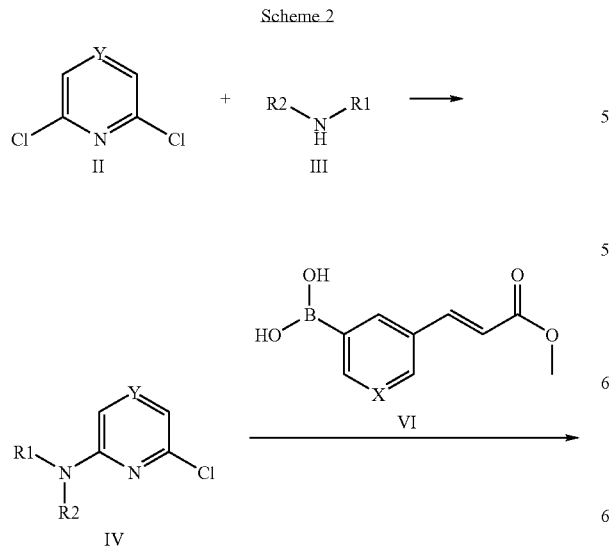

In this case, an ester such as VI is utilized in the Suzuki coupling with IV providing an intermediate (VII) which is subsequently hydrolyzed to VIII. Again, modification of R₁ or R₂, as suggested above for Scheme 1 can provide additional desired compounds of formula I.

Related analogs whereby the carbon-carbon double bond is saturated can be obtained as shown in Scheme 3.

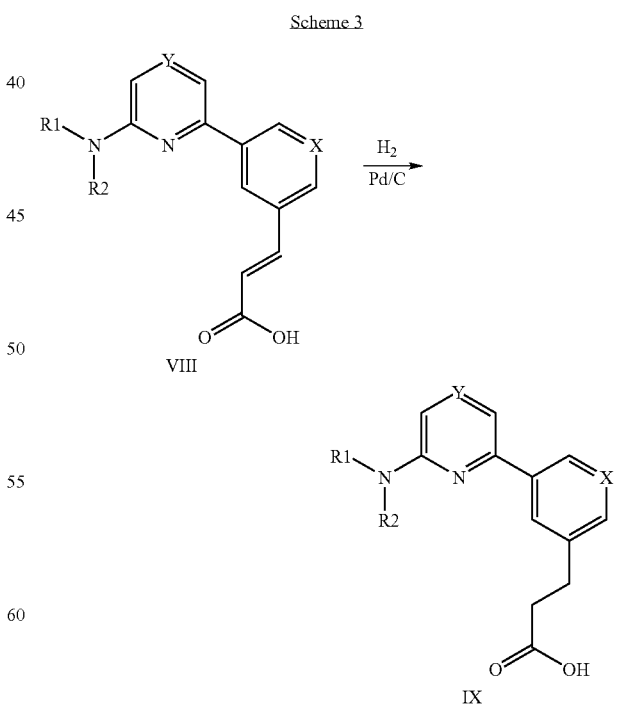

As shown in Scheme 3, the saturated analogs (IX) can be prepared by standard hydrogenation methods known to those skilled in the art. Alternatively, these could be synthesized directly from IV (Schemes 1,2) by Suzuki reaction with the appropriate reagent.

An alternate method for the synthesis of I whereby X=N, C and Y=N, C can be facilitated as shown in Scheme 4.

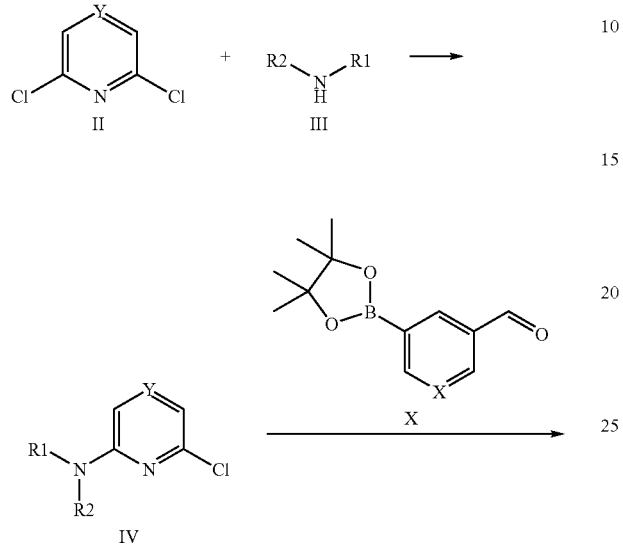

For Scheme 4, the intermediate IV is treated with an aldehyde reagent such as X using standard Suzuki coupling conditions. The resulting intermediate (XI) is then reacted with a phosphonate anion generated by treatment of the phosphonate with a suitable base such as NaH to provide XII whereby $R_4$ can be further functionalized. Again, modification of $R_1$ or $R_2$, as suggested above for Scheme 1 can provide additional desired compounds of formula I.

Additional modification of acrylic acid derivatives such as VIII can be done as shown in schemes 5, 6, and 7.

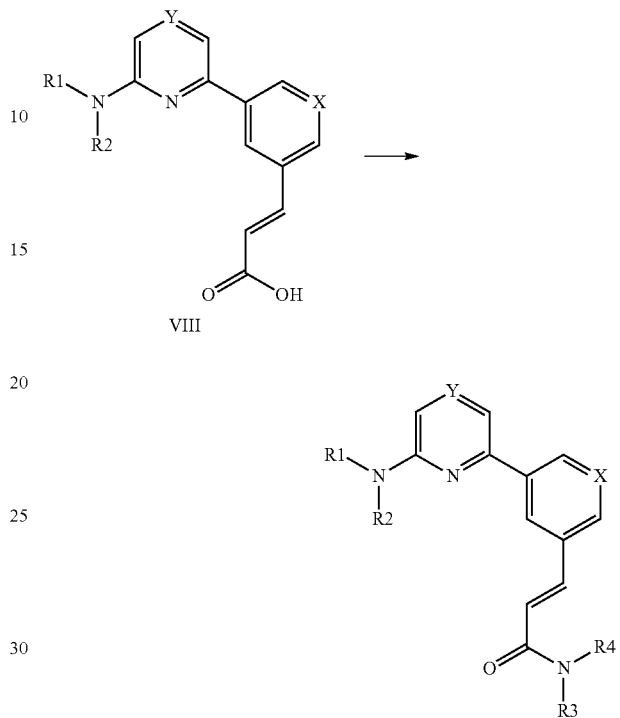

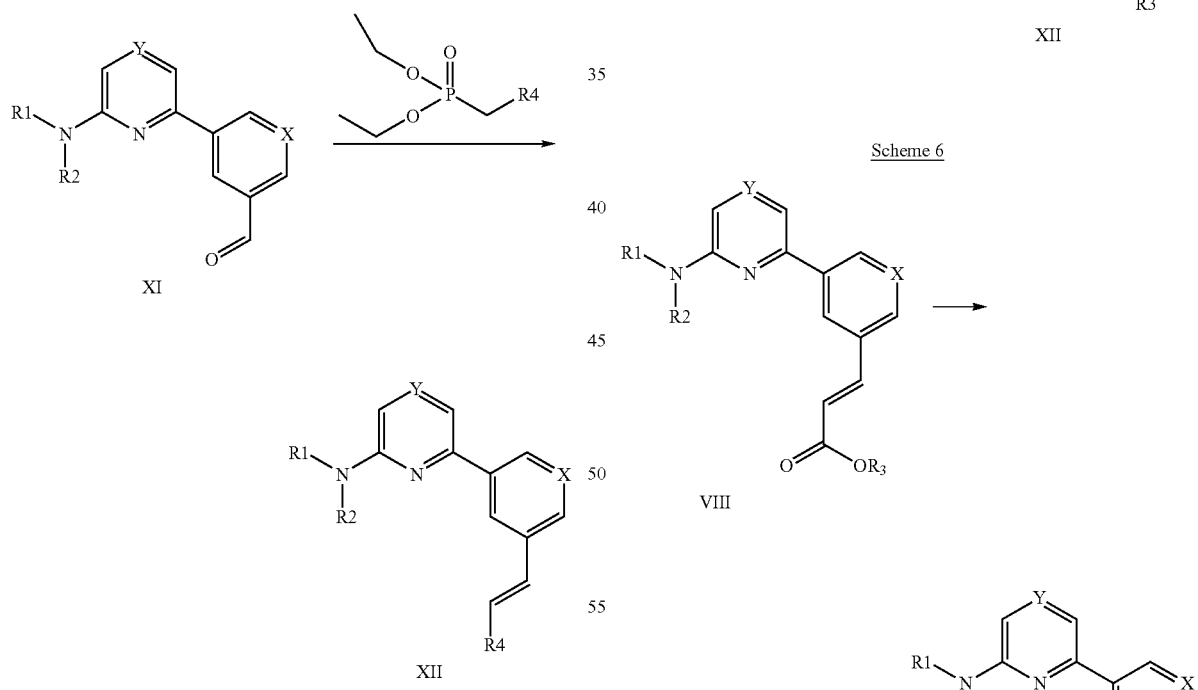

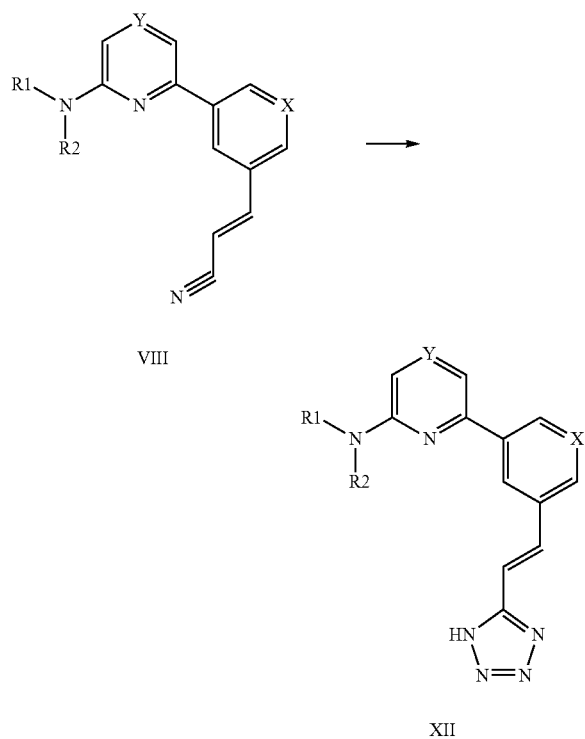

VIII

XII

For example, in Scheme 5 the acid analog of VIII can be converted to an amide or sulfonamide by use of a suitable coupling reagent and an amine or sulfonamide. In Scheme 6, an ester analog of VIII can be reduced to an alcohol by use of a suitable reducing agent. In Scheme 7 the nitrile analog of VIII can be converted to a tetrazole using an azide and a suitable acid.

SYNTHETIC EXAMPLES

Example 1

Preparation of compound 1; (E)-3-{3-[6-(4-Amino-cyclohexylamino)-pyrazin-2-yl]-phenyl}-acrylic acid

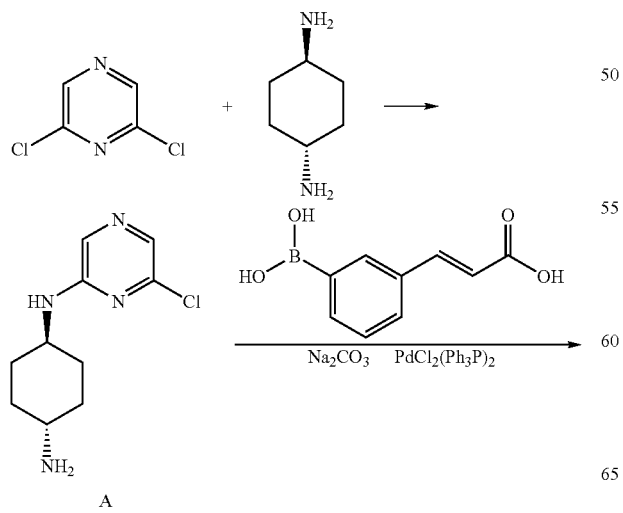

A

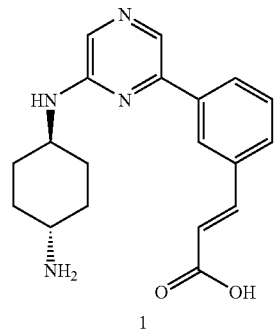

1

2,6-Dichloropyrazine (100 mg, 0.67 mmol) was dissolved in 1 mL dichloromethane. Trans-1,4-cyclohexanediamine (137 mg, 1.2 mmol) was added and the resulting mixture was agitated for 72 hours. The reaction mixture was directly loaded onto a flash column and eluted with an ammonium hydroxide/methanol/dichloromethane gradient. The intermediate A (17 mg, 11%) was isolated by evaporation of the solvent and used directly. 3-(E-2-carboxyvinyl)benzeneboronic acid (25 mg, 0.13 mmol) and bistriphenylphosphine-palladium(II)chloride (10 mg, 0.01 mmol) were combined in a microwave reaction tube. Intermediate A prepared above (17 mg, 0.07 mmol) was added as a solution in 3 mL DMF, and 1 mL of 2M $Na_2CO_3$ was then added. The tube was sealed and the reaction mixture was heated in a microwave reactor for 10 minutes at 100° C. The reaction mixture was then filtered through a plug of celite and purified directly by preparative HPLC. The title compound was collected as a white solid (3 mg, 12%) following evaporation of the solvent; MS analysis electrospray, 339 (M+H).

Using methods similar to those described in the above example, the following analogs were also synthesized:

[3] (E)-3-{3-[6-(4-Hydroxy-cyclohexylamino)-pyrazin-2-yl]-phenyl}-acrylic acid; MS, electrospray, 340 (M+H)

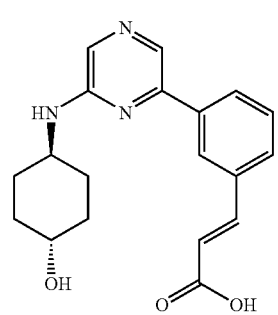

| 79 | 80 |
|---|---|
| [5] (E)-3-{3-[6-(4-Amino-butylamino)-pyrazin-2-yl]-phenyl}-acrylic acid; MS, electrospray, 313 (M+H) | [8] (E)-3-{3-[6-(3-Dimethylamino-propylamino)-pyrazin-2-yl]-phenyl}-acrylic acid; MS, electrospray, 327 (M+H) |

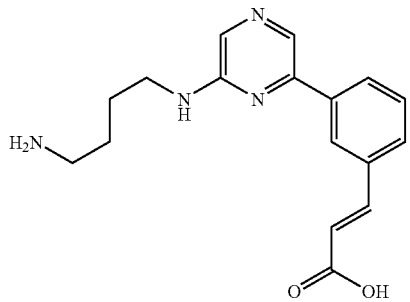 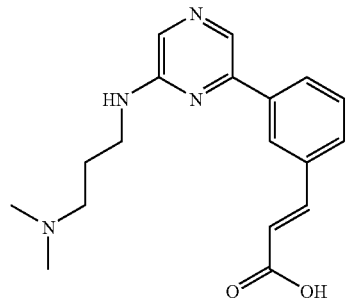

[6] (E)-3-{3-[6-(3-Amino-propylamino)-pyrazin-2-yl]-phenyl}-acrylic acid; MS, electrospray, 299 (M+H)

[9] (E)-3-{3-[6-(2-Dimethylamino-ethylamino)-pyrazin-2-yl]-phenyl}-acrylic acid; MS, electrospray, 313 (M+H)

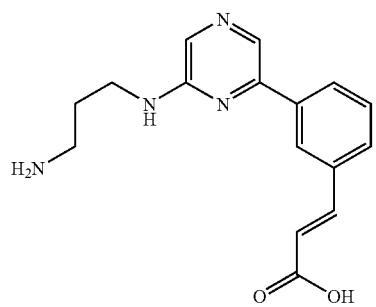 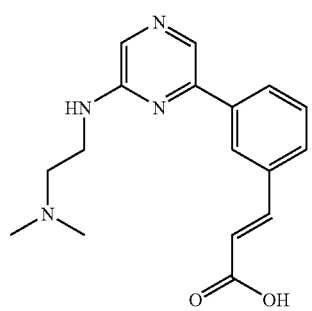

[7] (E)-3-{3-[6-(3-Amino-2,2-dimethyl-propylamino)-pyrazin-2-yl]-phenyl}-acrylic acid; MS, electrospray, 327 (M+H)

[10] (E)-3-(3-{6-[Methyl-(3-methylamino-propyl)-amino]-pyrazin-2-yl}-phenyl)-acrylic acid; MS, electrospray, 327 (M+H)

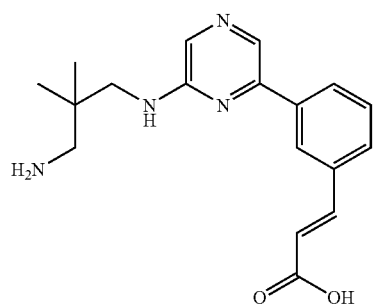 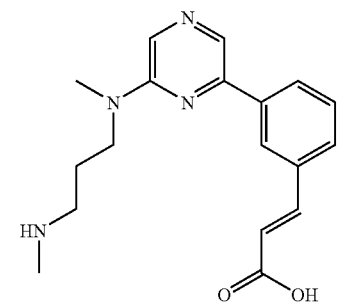

[12] (E)-3-{3-[6-(2-Amino-ethylamino)-pyrazin-2-yl]-phenyl}-acrylic acid; MS, electrospray, 285 (M+H)

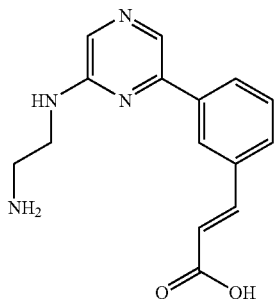

[13] (E)-3-(3-{6-[Methyl-(2-methylamino-ethyl)-amino]-pyrazin-2-yl}-phenyl)-acrylic acid; MS, electrospray, 313 (M+H)

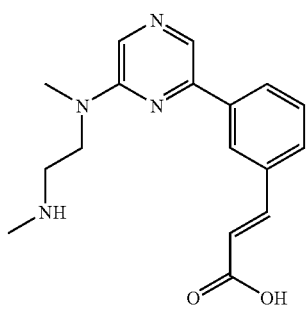

[14] (E)-3-{3-[6-(3-Dimethylamino-propylamino)-pyrazin-2-yl]-phenyl}-acrylic acid; MS, electrospray, 341 (M+H)

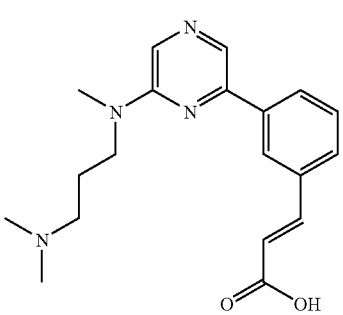

[15] (E)-3-{3-[6-(Carbamoylmethyl-amino)-pyrazin-2-yl]-phenyl}-acrylic acid; MS, electrospray, 299 (M+H)

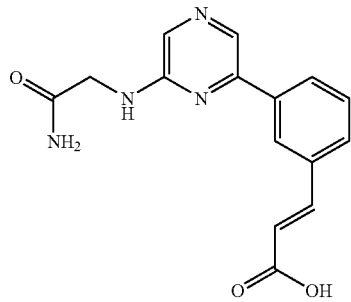

[16] (E)-3-{3-[6-(2-Carbamoyl-ethylamino)-pyrazin-2-yl]-phenyl}-acrylic acid; MS, electrospray, 313 (M+H)

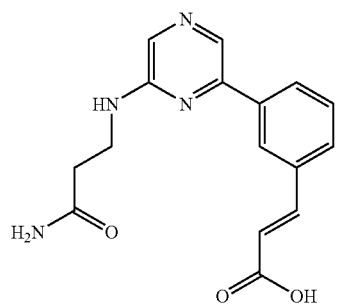

[17] (E)-3-{3-[6-(2-Hydroxy-ethylamino)-pyrazin-2-yl]-phenyl}-acrylic acid; MS, electrospray, 286 (M+H)

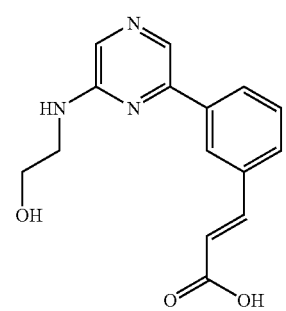

[18] (E)-3-{3-[6-(3-Hydroxy-propylamino)-pyrazin-2-yl]-phenyl}-acrylic acid; MS, electrospray, 300 (M+H)

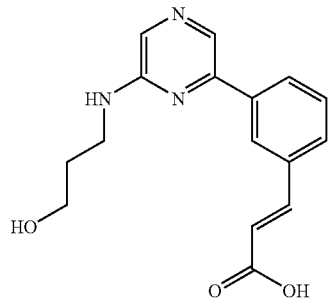

[19] (E)-3-{3-[6-(3-Methoxy-propylamino)-pyrazin-2-yl]-phenyl}-acrylic acid; MS, electrospray, 314 (M+H)

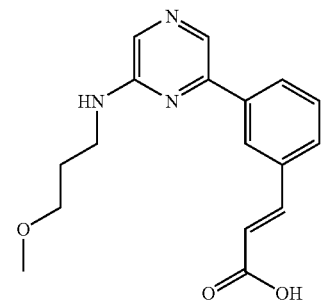

[20] (E)-3-{3-[6-(2-Methoxy-ethylamino)-pyrazin-2-yl]-phenyl}-acrylic acid; MS, electrospray, 300 (M+H)

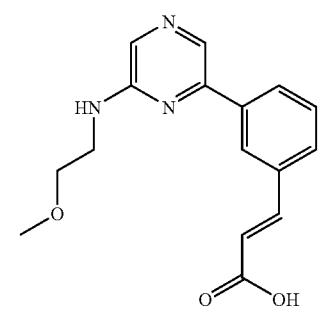

[21] (E)-3-{3-[6-(2-Acetylamino-ethylamino)-pyrazin-2-yl]-phenyl}-acrylic acid; MS, electrospray, 327 (M+H)

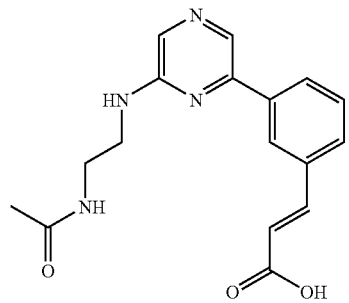

[22] (E)-3-{3-[6-(4-Aminomethyl-piperidin-1-yl)-pyrazin-2-yl]-phenyl}-acrylic acid; MS, electrospray, 339 (M+H)

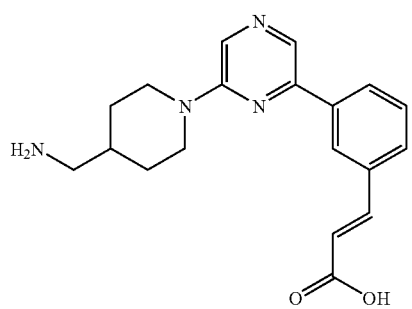

[23] (E)-3-{3-[6-(4-Methyl-[1,4]diazepan-1-yl)-pyrazin-2-yl]-phenyl}-acrylic acid; MS, electrospray, 339 (M+H)

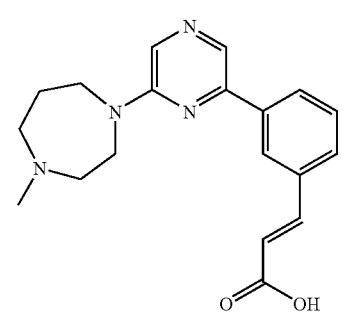

[24] (E)-3-{3-[6-(4-Dimethylamino-piperidin-1-yl)-pyrazin-2-yl]-phenyl}-acrylic acid; MS, electrospray, 353 (M+H)

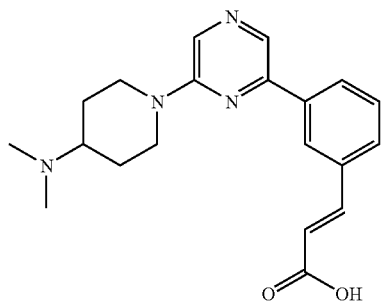

[26] (E)-3-[3-(4-Methyl-3,4,5,6-tetrahydro-2H-[1,2'] bipyrazinyl-6'-yl)-phenyl]-acrylic acid; MS, electrospray, 325 (M+H)

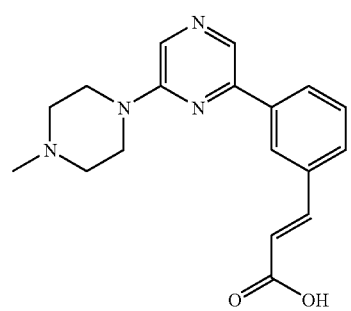

[27] (E)-3-[3-(6-[1,4]Diazepan-1-yl-pyrazin-2-yl)-phenyl]-acrylic acid; MS, electrospray, 325 (M+H)

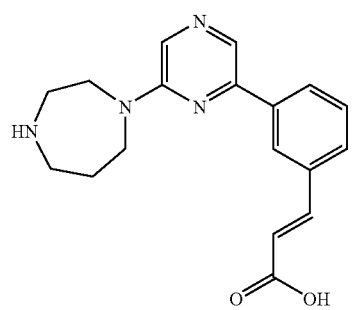

[28] (E)-3-[3-(3,4,5,6-Tetrahydro-2H-[1,2]bipyrazinyl-6'-yl)-phenyl]-acrylic acid; MS, electrospray, 311 (M+H)

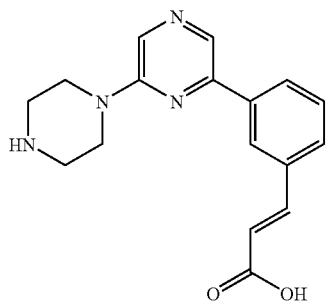

[29] (E)-3-{3-[6-(4-Benzyl-[1,4] diazepan-1-yl)-pyrazin-2-yl]-phenyl}-acrylic acid; MS, electrospray, 415 (M+H)

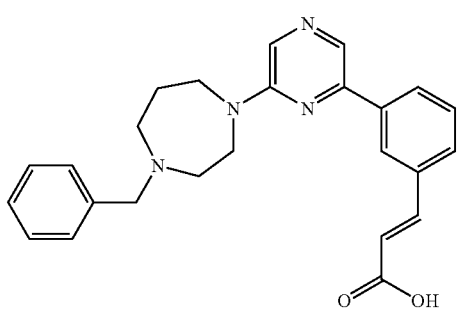

[30] (E)-3-{3-[6-(3-Dimethylamino-pyrrolidin-1-yl)-pyrazin-2-yl]-phenyl}-acrylic acid; MS, electrospray, 339 (M+H)

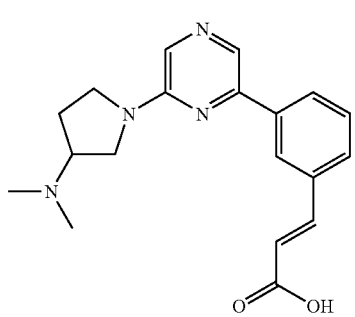

87

[31] (E)-3-{3-[6-(4-Acetyl-[1,4]diazepan-1-yl)-pyrazin-2-yl]-phenyl}-acrylic acid; MS, electrospray, 367 (M+H)

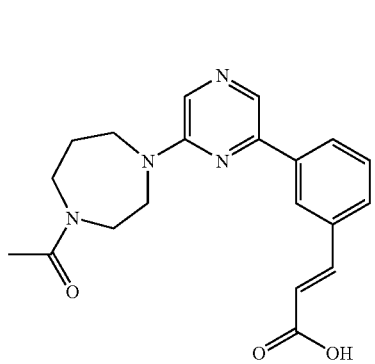

[32] (E)-3-{3-[6-(4-Hydroxy-piperidin-1-yl)-pyrazin-2-yl]-phenyl}-acrylic acid; MS, electrospray, 326 (M+H)

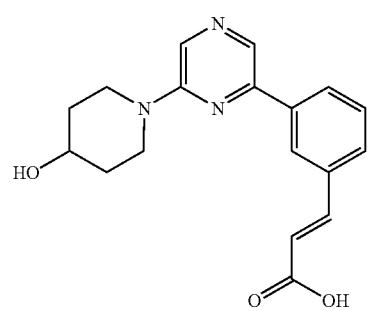

[33] (E)-3-{3-[6-(4-Hydroxymethyl-piperidin-1-yl)-pyrazin-2-yl]-phenyl}-acrylic acid; MS, electrospray, 340 (M+H)

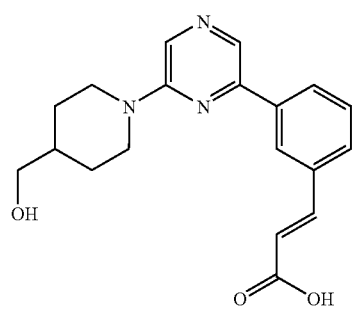

88

[34] (E)-3-[3-(6-Morpholin-4-yl-pyrazin-2-yl)-phenyl]-acrylic acid; MS, electrospray, 312 (M+H)

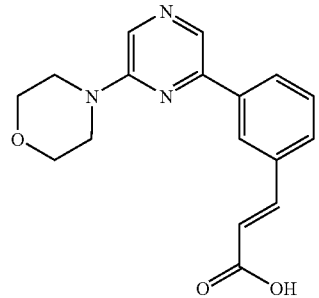

[35] (E)-3-[3-(6-Azepan-1-yl-pyrazin-2-yl)-phenyl]-acrylic acid; MS, electrospray, 324 (M+H)

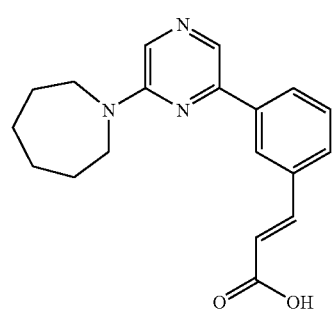

Example 2

Preparation of compound 2 (E)-3-{3-[6-(4-Amino-cyclohexylamino)-pyrazin-2-yl]-phenyl}-acrylic acid

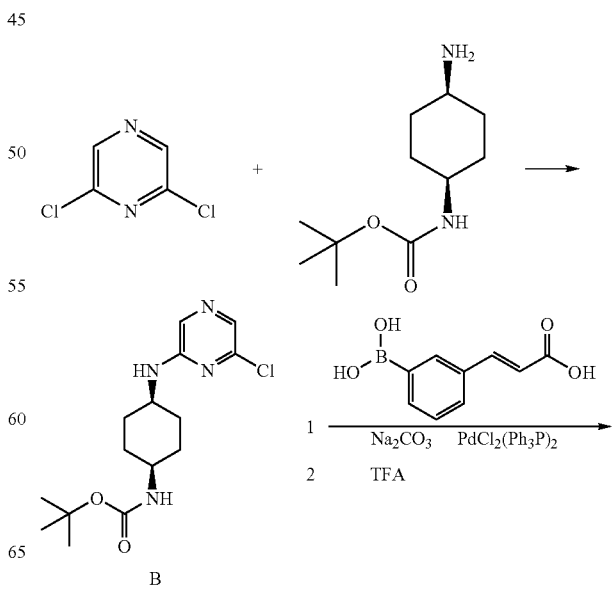

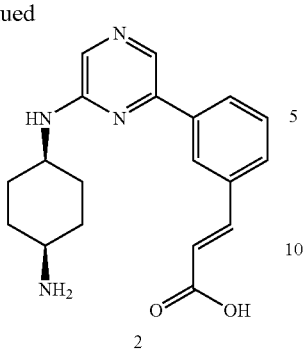

2,6-Dichloropyrazine (100 mg, 0.67 mmol) was dissolved in 2 mL DMF. Cis-(4-Amino-cyclohexyl)-carbamic acid tert-butyl ester (257 mg, 1.2 mmol) was added and the resulting mixture was heated at 45° C. with agitation for 24 hours. The reaction mixture was concentrated and purified by preparative TLC using a methanol/dichloromethane eluant. Intermediate B (90 mg, 41%) was isolated by evaporation of the solvent and was used directly. 3-(E-2-carboxyvinyl)benzeneboronic acid (55 mg, 0.28 mmol) and bistriphenylphosphinepalladium(II)chloride (15 mg, 0.015 mmol) were combined in a microwave reaction tube. Intermediate B prepared above (90 mg, 0.27 mmol) was added as a solution in 3 mL DMF, and 1 mL of 2M $Na_2CO_3$ was then added. The tube was sealed and the reaction mixture was heated in a microwave reactor for 10 minutes at 100° C. The reaction mixture was then filtered through a plug of celite and purified directly using preparative TLC with a methanol/ammonium hydroxide/dichloromethane eluant. The intermediate was isolated by evaporation of the solvent and taken up in 5 mL of a 20% TFA/dichloromethane solution. After stirring at room temperature overnight, the mixture was concentrated and purified by preparative HPLC. The title compound was collected as a yellow solid (85 mg, 91%) following evaporation of the solvent; MS analysis electrospray, 339 (M+H).

Using methods similar to those described in the above example, the following analog was also synthesized:

[4] (E)-3-(3-{6-[(Piperidin-4-ylmethyl)-amino]-pyrazin-2-yl}-phenyl)-acrylic acid; MS, electrospray, 339 (M+H)

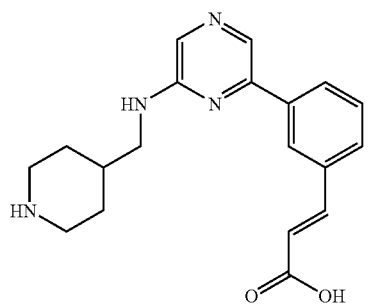

Example 3

Preparation of compound 36; (E)-3-[3-[6-(4-Methyl-[1,4]diazepan-1-yl)-pyridin-2-yl]-phenyl]-acrylic acid

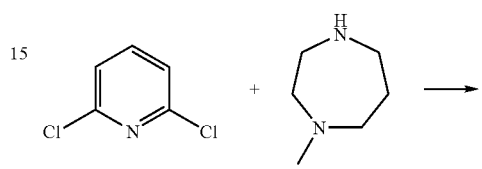

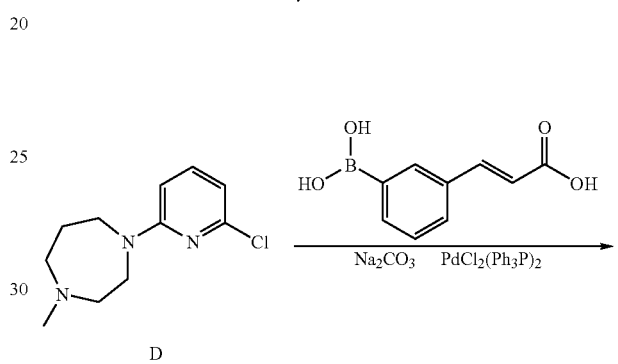

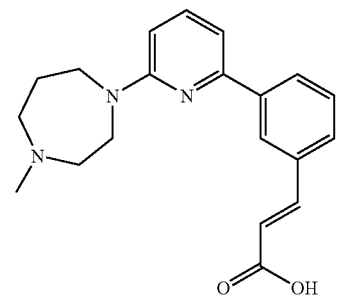

36

2,6-Dichloropyridine (200 mg, 1.35 mmol) was dissolved in 5 mL DMF. N-methylhomopiperazine (500 μL, 4.02 mmol) was added and the resulting mixture was heated at 105° C. for 16 hours. The reaction mixture was concentrated, loaded onto a flash column and eluted with a methanol/dichloromethane gradient. Intermediate D was isolated by evaporation of the solvent and used directly (160 mg, 53%). 3-(E-2-carboxyvinyl)benzeneboronic acid (50 mg, 0.26 mmol) and bistriphenylphosphinepalladium(II)chloride (10 mg, 0.01 mmol) were combined in a microwave reaction tube. Intermediate D prepared above (55 mg, 0.24 mmol) was added as a solution 3 mL DMF, and 1 mL of 2M $Na_2CO_3$ was then added. The tube was sealed and the reaction mixture was heated in a microwave reactor for 10 minutes at 100° C. The reaction mixture was then filtered through a plug of celite and purified directly by preparative HPLC. The product was further purified by preparative TLC to provide the title compound as a white solid (10 mg, 12%); MS analysis electrospray, 338 (M+H).

Example 4

Preparation of compound 25; (E)-3-{3-[6-(4-Aminopiperidin-1-yl)-pyrazin-2-yl]-phenyl}-acrylic acid

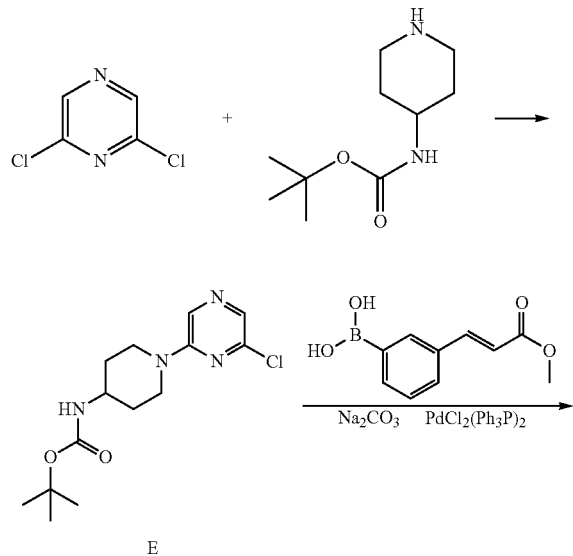

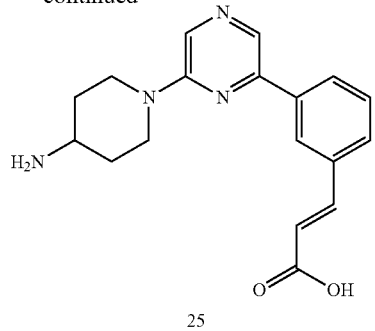

2,6-Dichloropyrazine (100 mg, 0.67 mmol) was dissolved in 1 mL dichloromethane. Piperidin-4-yl-carbamic acid tert-butyl ester (240 mg, 1.2 mmol) was added and the resulting mixture was agitated at room temperature for 72 hours. The reaction mixture was loaded directly onto a flash column and eluted with an ethyl acetate/hexane gradient. Intermediate E (108 mg, 52% yield) was isolated by evaporation of the solvents. [3-(E-3-methoxy-3-oxo-1-propen-1-yl)phenyl]boronic acid (80 mg, 0.41 mmol) and bistriphenylphosphine-palladium(II)chloride (20 mg, 0.02 mmol) were combined in a microwave reaction tube. Intermediate E prepared above (104 mg, 0.33 mmol) was added as a solution in 3 mL DMF, and 1 mL of 2M $Na_2CO_3$ was then added. The tube was sealed and the reaction mixture was heated in a microwave reactor for 10 minutes at 100° C. The reaction mixture was then filtered through a plug of celite, and the solvents were concentrated to provide 45 mg (32% yield) of intermediate F which was used directly. Intermediate F (40 mg, 0.09 mmol) was dissolved in methanol and treated with 1 mL of 4N HCl in dioxane. After stirring the mixture for 16 hours at room temperature, the solvents were evaporated to provide the esterified product G which was subsequently taken up in 2 mL acetonitrile, and treated with 1 mL of 1N NaOH. The resulting mixture was stirred at room temperature for 4 hours then concentrated. The residue was purified by preparative HPLC, then further purified by preparative TLC. The title compound (13 mg, 43%-2 steps) was isolated following evaporation of the solvent; MS analysis electrospray, 325 (M+H).

Example 5

Preparation of compound 11; (E)-3-{3-[6-(3-Ethylamino-propylamino)-pyrazin-2-yl]-phenyl}-acrylic acid

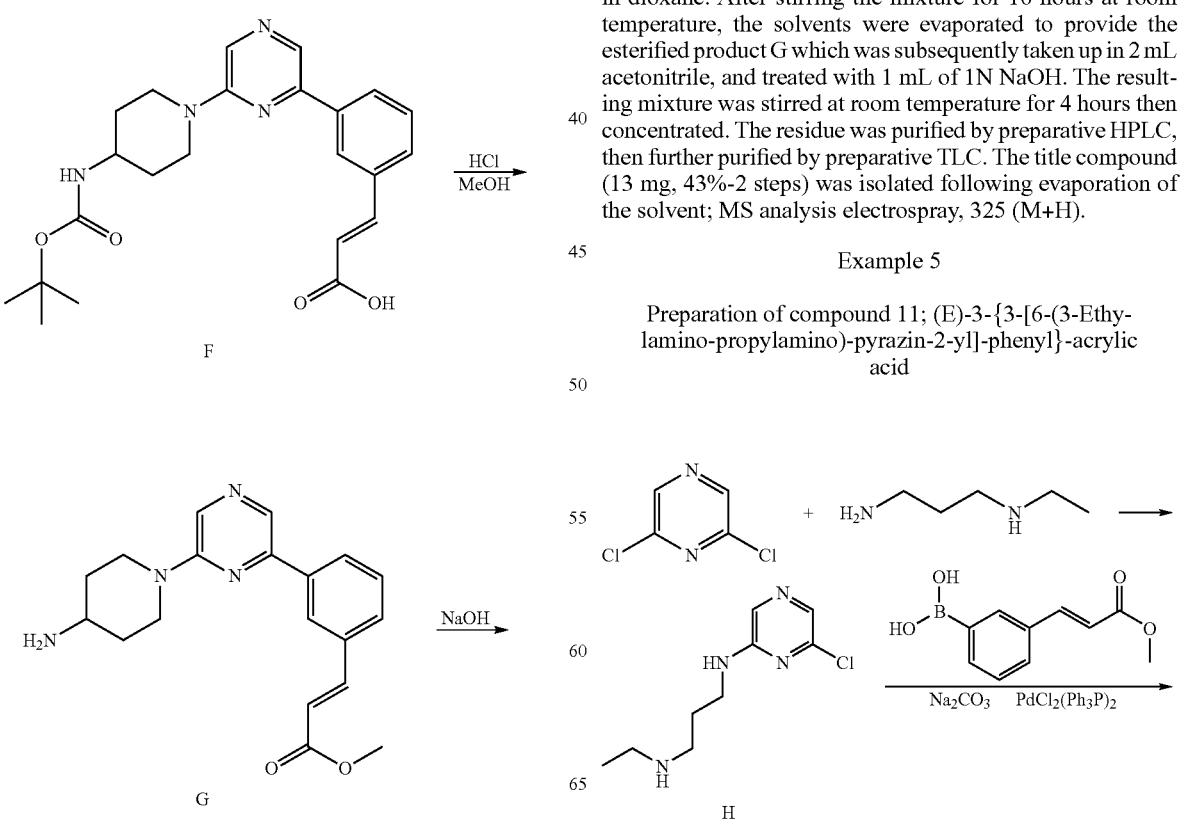

-continued

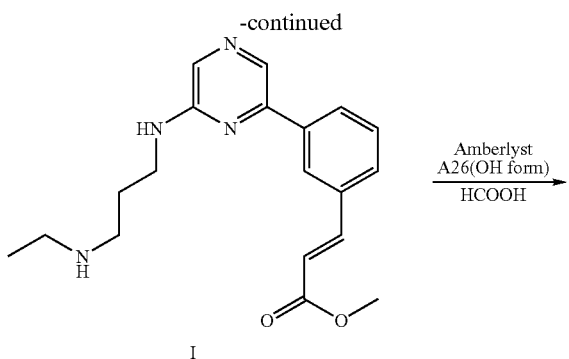

I 2,6-Dichloropyrazine (298 mg, 2.0 mmol) was dissolved in 25 mL dichloromethane. 1,5,7-triazabicyclo[4.4.0]dec-5-ene polystyrene (PS-TBD) (2.0 g, 5.0 mmol) was added followed by N-ethyltrimethylenediamine (194 mg, 1.90 mmol). The resulting mixture was agitated at room temperature overnight. The resin was filtered and the mother liquors were concentrated to a solid H (429 mg, 100%, mixture of isomers), which was used directly. [3-(E-3-methoxy-3-oxo-1-propen-1-yl)phenyl]boronic acid (618 mg, 3.0 mmol) and bistriphenylphosphinepalladium(II)chloride (35 mg, 0.05 mmol) were dispersed in 5 mL DMF in a reaction tube. Subsequently 1.5 mL of 2M $Na_2CO_3$ was added followed by intermediate H prepared above (429 mg, 2.0 mmol) as a solution in 5 mL DMF. The tube was sealed and the reaction mixture was heated at 85° C. for 72 hours. The reaction mixture was then filtered through a plug of celite, and the mother liquors were treated with a silica-bound sulfonic acid (Si-tosic acid), (9.5 g, 8.36 mmol). The resulting mixture was agitated for 24 hours, then the silica was isolated by filtration and washed with methanol. Intermediate I (150 mg, 88%, mixture of isomers) was eluted from the silica with 7N ammonia in methanol, and isolated by concentration of the eluant. The mixture was used directly. Intermediate I prepared above (140 mg, 0.41 mmol) was dissolved in 15 mL methanol. Amberlyst A26 (OH form) (1.5 g, 2.16 mmol) was added and the resulting mixture was agitated at room temperature for 72 hours. The resin was isolated by filtration and washed with methanol. The product was eluted from the resin using 20% formic acid in methanol, and isolated by concentration of the eluant (105 mg, 73%, mixture of isomers). The mixture was purified by preparative HPLC to provide the title compound (18.4 mg, 13%); MS analysis electrospray, 327 (M+H).

Example 6

Preparation of compound 37; (E)-3-{5-[6-(4-Methyl-[1,4]diazepan-1-yl)-pyrazin-2-yl]-pyridin-3-yl}-acrylic acid

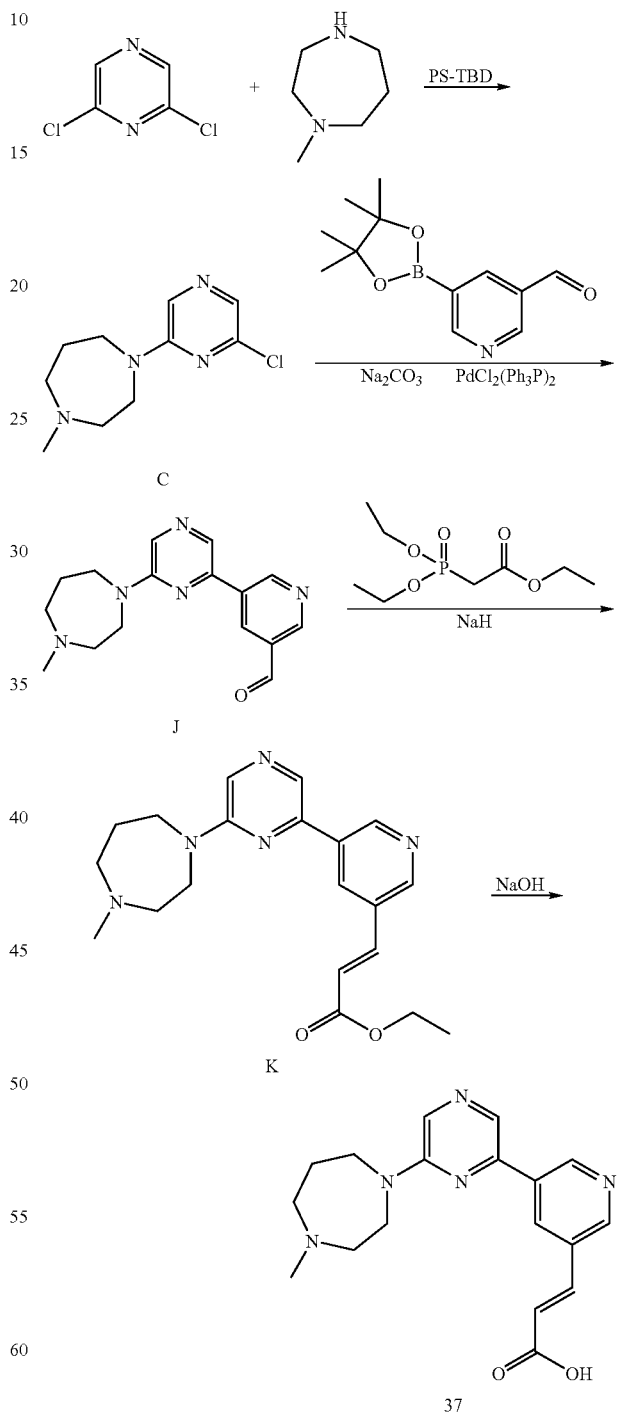

2,6-Dichloropyrazine (600 mg, 4.02 mmol) was dissolved in 35 mL dichloromethane. 1,5,7-triazabicyclo[4.4.0]dec-5-ene polystyrene (PS-TBD) (3.0 g, 7.5 mmol) was added followed by N-methylhomopiperazine (472 µL, 3.79 mmol). The resulting mixture was agitated at room temperature for 4 hours. The resin was filtered and the mother liquors were concentrated to an oil which was triturated in dichloromethane to provide intermediate C (495 mg, 54%) as a white solid which was used directly. 5-(4,4,5,5-tetramethyl-1,3,2-dioxaborolan-2-yl)pyridine-3-carbaldehyde (103 mg, 0.44 mmol) and bistriphenylphosphinepalladium(II)chloride (20 mg, 0.02 mmol) were combined in a microwave reaction tube. Intermediate C prepared above (100 mg, 0.44 mmol) was added as a solution in 3 mL DMF, and 1 mL of 2M Na$_2$CO$_3$ was then added. The tube was sealed and the reaction mixture was heated in a microwave reactor for 10 minutes at 100° C. The reaction mixture was then filtered through a plug of celite, the solvents were concentrated, and the residue was purified by preparative HPLC. Intermediate J (39 mg, 30%) was isolated as a yellow solid. Triethyl-2-phosphonopropionate (26.8 µL, 0.13 mmol) was added to a slurry of NaH (4 mg, 0.15 mmol) in 2 mL THF. After 20 minutes, the mixture was added to intermediate J prepared above (39 mg, 0.13 mmol). The resulting mixture was stirred at room temperature for 2 hours, after which time it was concentrated, and the residue was purified by preparative TLC providing intermediate K (22 mg, 46%) as a yellow solid, which was dissolved in 2 mL acetonitrile and treated with 500 µL of 1N NaOH. The resulting mixture was stirred at room temperature for 16 hours, after which time it was concentrated and the residue was purified by preparative HPLC. The title compound (18 mg, 88%) was isolated as a pale yellow solid. MS analysis electrospray, 340 (M+H).

Example 7

Preparation of compound 38; 3-[3-[6-(4-Methyl-[1,4]diazepan-1-yl)-pyrazin-2-yl]-phenyl]-propionic acid

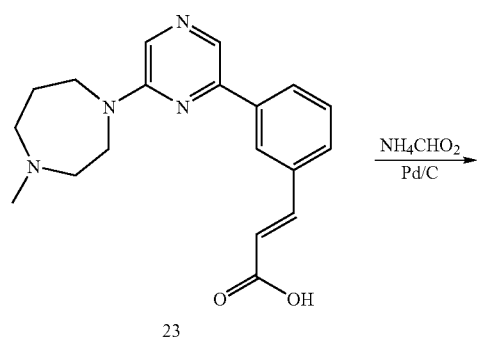

Compound 23 (30 mg, 0.09 mmol) was combined with Pd/C (2 mg) and ammonium formate (31.5 mg, 0.5 mmol) in 1 mL ethanol in a reaction tube. The tube was sealed and heated at 70° C. for 72 h. The reaction mixture was cooled, filtered, and concentrated. The crude product was purified using preparative HPLC to provide the title compound (17 mg, 57%); MS analysis electrospray, 341 (M+H).

Example 8

Preparation of compound 39; (E)-3-{3-[6-(4-Methyl-[1,4]diazepan-1-yl)pyrazin-2-yl]-phenyl}-acrylic acid methyl ester

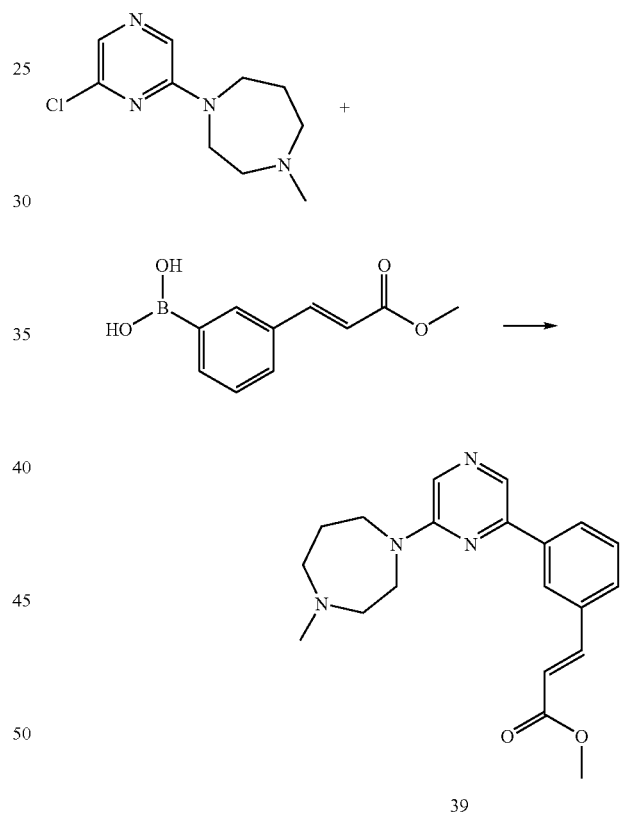

[3-(E-3-methoxy-3-oxo-1-propen-1-yl)phenyl]boronic acid (125 mg, 0.61 mmol) and bistriphenylphosphinepalladium(II)chloride (30 mg, 0.057 mmol) were combined in a microwave reaction tube. Subsequently 1-(6-chloro-pyrazin-2-yl)-4-methyl-[1,4]diazepane (130 mg, 0.57 mmol) was added as a solution in DMF (8 mL) followed by an aqueous solution of Na$_2$CO$_3$ (2M, 3 mL, 6 mmol). The tube was sealed and the reaction mixture was heated in the microwave at 120° C. for 20 min. The reaction mixture was then filtered through a plug of celite, and purified by flash chromatography to provide the title compound (124 mg 61%); MS analysis electrospray, 353 (M+H).

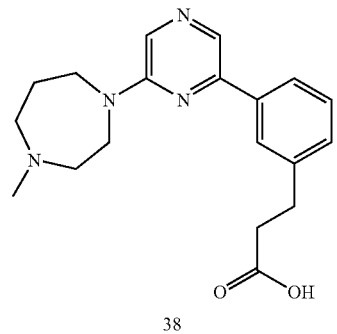

Example 9

Preparation of compound 40; (E)-3-[3-[6-(4-Methyl-[1,4]diazepan-1-yl)-pyrazin-2-yl]-phenyl]-acrylamide

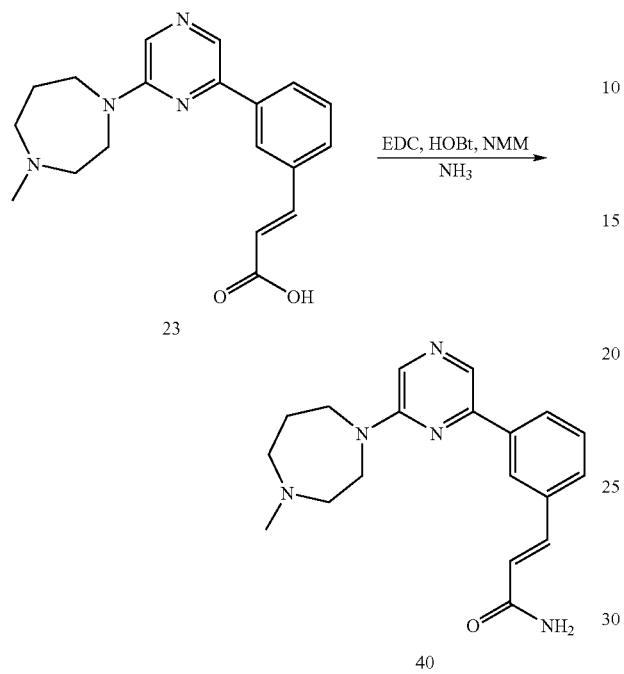

Compound 23 (36 mg, 0.106 mmol) was dissolved in 1 mL DMF in a reaction tube. N-(3-dimethylaminopropyl)-N'-ethylcarbodiimide hydrochloride (38.3 mg, 0.2 mmol), benzotriazol-1-ol (27 mg, 0.2 mmol) and N-methylmorpholine (0.02 mL, 0.18 mmol) were added and the tube was sealed and agitated for 15 min. The amine (1.0 mL, 0.5M in dioxane, 0.5 mmol) was added and the resulting mixture was agitated at 35° C. for 72 h. The reaction mixture was concentrated and the product was purified by preparative HPLC to provide the title compound (17 mg, 47%); MS analysis electrospray, 338 (M+H).

Example 10

Preparation of compound 41; (E)-3-[3-[6-(4-Methyl-[1,4]diazepan-1-yl)-pyrazin-2-yl]-phenyl]-prop-2-en-1-ol

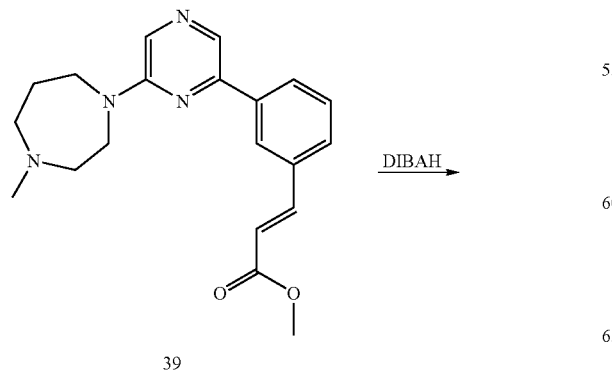

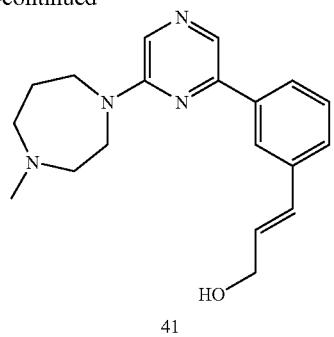

Compound 39 (35.2 mg, 0.1 mmol) was dissolved in THF (1 mL) and cooled to 0° C. under an atmosphere of $N_2$. DIBAH (1M in THF, 0.12 mL, 0.12 mmol) was added. The reaction mixture was then stirred at room temperature for 2 h, after which time an additional 0.12 mL of DIBAH was added. After 1 h, the reaction mixture was added to a saturated solution of $NaHCO_3$ (5 mL) and ethyl acetate (5 mL) was added. The organic layer was separated and the aqueous was extracted with ethyl acetate (2×5 mL). The combined organic extracts were washed with brine, dried and concentrated. The residue was purified by flash chromatography to provide the title compound (11 mg, 34%). MS analysis electrospray, 325 (M+H).

Example 11

Preparation of compound 42; (E)-3-[3-[6-(4-Methyl-[1,4]diazepan-1-yl)-pyrazin-2-yl]-phenyl]-acrylonitrile

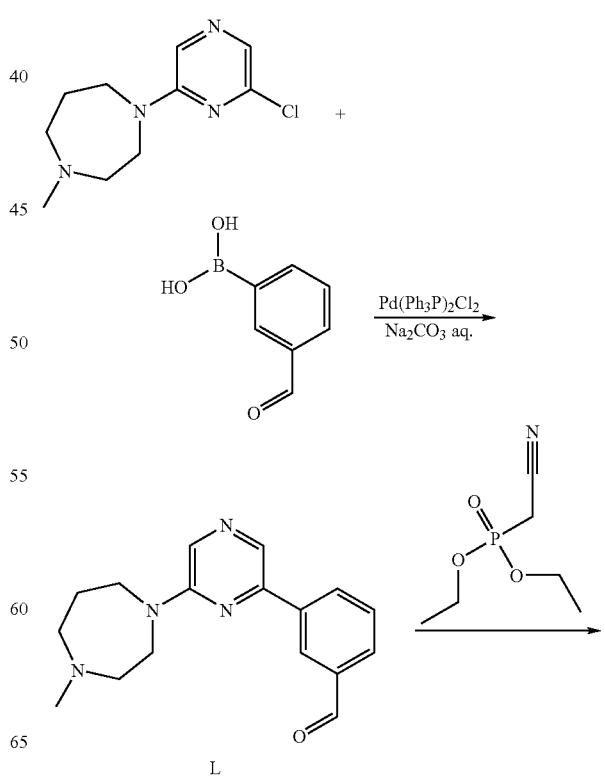

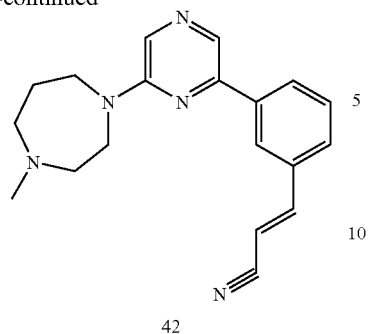

42

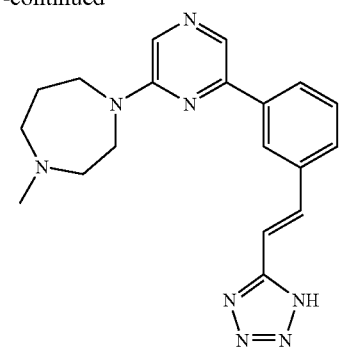

43

1-(6-Chloro-pyrazin-2-yl)-4-methyl-[1,4] diazepane (360 mg, 1.59 mmol), (intermediate C prepared in example 3), 3-formylphenylboronic acid (235 mg, 1.58 mmol) and bis-triphenylphosphinepalladium(II)chloride (21 mg, 0.03 mmol) were dispersed in 10 mL DMF in a reaction tube. Subsequently 1.5 mL of 2M $Na_2CO_3$ was added. The tube was sealed and the reaction mixture was heated at 90° C. for 3 hours. The reaction mixture was then filtered through a plug of celite, diluted with ethyl acetate and water (25 mL), and the organic phase was separated. The aqueous phase was extracted with 2×10 mL ethyl acetate. The organic extracts were combined, washed with brine, dried and concentrated. The residue was purified by flash chromatography. Intermediate L (337 mg, 72%; MS analysis electrospray, 297, M+H) was isolated by concentration of the solvents and used directly. Sodium hexamethyldisilazane (0.22 mL, 1M in THF, 0.22 mmol) was added to a solution of cyanomethyl-phosphonic acid diethyl ester (0.034 mL, 0.21 mmol) in 1 mL THF under an atmosphere of $N_2$. The mixture was stirred for 2 h after which time a solution of 3-[6-(4-methyl-[1,4] diazepan-1-yl)-pyrazin-2-yl]-benzaldehyde in 2 mL THF was added. After 15 min. the solvents were evaporated and the residue was diluted with 5 mL water and extracted with ethyl acetate (2×5 mL). The organic extracts were combined, washed with brine, dried and concentrated. The residue was purified by flash chromatography to provide the title compound (40 mg, 62%); MS analysis electrospray, 320 (M+H).

Example 12

Preparation of 43; 1-Methyl-4-(6-{3-[(E)-2-(1H-tetrazol-5-yl)-vinyl]-phenyl}-pyrazin-2-yl)-[1,4] diazepane

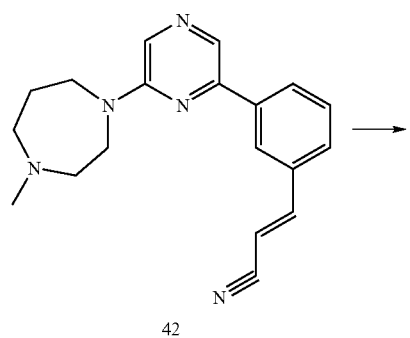

42

Compound 42 (25 mg, 0.08 mmol) was dissolved in DMF (0.5 mL) and added to a solution of $NaN_3$ (13.2 mg, 0.2 mmol) and ZnBr (44 mg, 0.2 mmol) in water (1.5 mL). The reaction mixture was then stirred for 72 h at 110° C., treated with 1N HCl (0.2 mL) and concentrated. The crude product was purified by preparative HPLC providing the title compound (7 mg, 24% yield); MS analysis electrospray, 363 (M+H).

Example 13

Preparation of 44; N-((E)-3-{3-[6-(4-Methyl-perhydro-1,4-diazepin-1-yl)-pyrazin-2-yl]-phenyl}-acryloyl)-methanesulfonamide

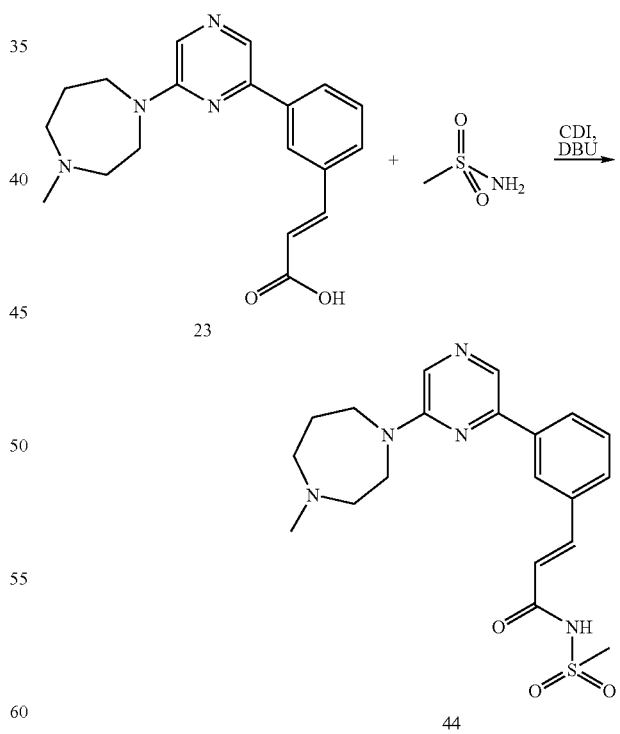

Compound 23 (33.8 mg, 0.1 mmol) was dissolved in THF (1.0 mL) and CDI (32.4 mg, 0.2 mmol) was added. The resulting mixture was stirred at ambient temperature for 30 min., heated at 55° C. for 1 h, then cooled to ambient temperature after which time methylsulfonamide (19 mg, 0.2 mmol) was added followed by DBU (0.03 mL, 0.2 mmol). The resulting mixture was stirred for 16 h, concentrated, and the crude product was purified by preparative HPLC. The title compound was isolated as a white solid (17 mg, 41.6% yield). MS analysis electrospray, 416 (M+H).

Example 14

Preparation of 45; (E)-N-(2-Hydroxy-ethyl)-3-{3-[6-(4-methyl-perhydro-1,4-diazepin-1-yl)-pyrazin-2-yl]-phenyl}-acrylamide

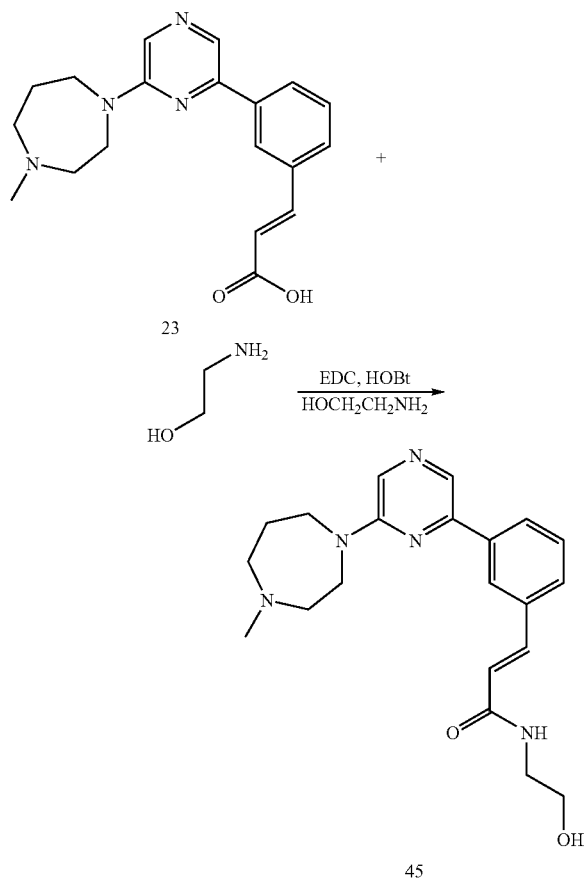

Compound 23 (36 mg, 0.1 mmol) was dissolved in DMF (1 mL) and N-(3-dimethylaminopropyl)-N'-ethylcarbodiimide hydrochloride (23 mg, 0.12 mmol), was added followed by benzotriazol-1-ol (16 mg, 0.12 mmol). The resulting mixture was stirred for 30 min. Ethanolamine (13.5 mg, 0.22 mmol) was added and the resulting mixture was stirred for 16 h. Subsequently an equivalent portion of EDC, HOBt and ethanolamine was again added and the resulting mixture was stirred an additional 24 h. The reaction mixture was concentrated and purified by preparative HPLC. The title compound (27 mg, 66.5% yield) was isolated as an amorphous solid. MS analysis electrospray, 382 (M+H).

Formulations

In another aspect of the invention, the compounds according to the invention are formulated into pharmaceutical compositions comprising an effective amount, preferably a pharmaceutically effective amount, of a compound according to the invention or a tautomer, prodrug, solvate, or salt thereof, and a pharmaceutically acceptable excipient or carrier.

The invention further provides a method of treating a disease-state or condition mediated by PIM-2 function in a patient in need of such treatment, the method comprising administering to the patient an effective amount of a pharmaceutically acceptable compound according to the invention or a tautomer, prodrug, solvate, or salt thereof.

The invention provides a method of treating a disease characterized by inflammatory processes, in a patient in need of such treatment, the method comprising administering to the patient an effective amount of a pharmaceutically acceptable compound according to the invention or a tautomer, prodrug, solvate, or salt thereof. In a preferred embodiment of the invention, the disease characterized by inflammatory processes is selected from: (i) lung diseases; (ii) rheumatic diseases or autoimmune diseases or joint diseases; (iii) allergic diseases; (iv) vasculitis diseases; (v) dermatological diseases; (vi) renal diseases; (vii) hepatic diseases; (viii) gastrointestinal diseases; (ix) proctological diseases; (x) eye diseases; (xi) diseases of the ear, nose, and throat (ENT) area; (xii) neurological diseases; (xiii) blood diseases; (xiv) tumor diseases; (xv) endocrine diseases; (xvi) organ and tissue transplantations and graft-versus-host diseases; (xvii) severe states of shock; (xviii) substitution therapy; and (xix) pain of inflammatory genesis. In another preferred embodiment of the invention, the disease characterized by inflammatory processes is selected from: type I diabetes, osteoarthritis, Guillain-Barre syndrome, restenosis following percutaneous transluminal coronary angioplasty, Alzheimer disease, acute and chronic pain, atherosclerosis, reperfusion injury, bone resorption diseases, congestive heart failure, myocardial infarction, thermal injury, multiple organ injury secondary to trauma, acute purulent meningitis, necrotizing enterocolitis, and syndromes associated with hemodialysis, leukopheresis, and granulocyte transfusion.

The invention also provides a kit for the in vitro diagnostic determination of the PIM-2 function in a sample, comprising: (a) a diagnostically effective amount of a compound according to the invention or a tautomer, prodrug, solvate, or salt thereof; and (b) instructions for use of the diagnostic kit.

Salt, Prodrug, Derivative, and Solvate Terms and Conventions

The terms "prodrug" or "prodrug derivative" mean a covalently-bonded derivative or carrier of the parent compound or active drug substance which undergoes at least some biotransformation prior to exhibiting its pharmacological effect(s). In general, such prodrugs have metabolically cleavable groups and are rapidly transformed in vivo to yield the parent compound, for example, by hydrolysis in blood, and generally include esters and amide analogs of the parent compounds. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can be readily prepared from the parent compounds using methods known in the art, such as those described in *A Textbook of Drug Design and Development*, Krogsgaard-Larsen and H. Bundgaard (eds.), Gordon & Breach, 1991, particularly Chapter 5: "Design and Applications of Prodrugs"; *Design of Prodrugs*, H. Bundgaard (ed.), Elsevier, 1985; *Prodrugs: Topical and Ocular Drug Delivery*, K. B. Sloan (ed.), Marcel Dekker, 1998; *Methods in Enzymology*, K. Widder et al. (eds.), Vol. 42, Academic Press, 1985, particularly pp. 309-396; *Burger's Medicinal Chemistry and Drug Discovery*, 5th Ed., M. Wolff (ed.), John Wiley & Sons, 1995, particularly Vol. 1 and pp. 172-178 and pp. 949-982; *Pro-Drugs as Novel Delivery Systems*, T. Higuchi and V. Stella (eds.), Am. Chem. Soc., 1975; *Bioreversible Carriers in Drug Design*, E. B. Roche (ed.), Elsevier, 1987, each of which is incorporated herein by reference in their entireties.

The term "pharmaceutically acceptable prodrug" as used herein means a prodrug of a compound of the invention which is, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible.

The term "salt" means an ionic form of the parent compound or the product of the reaction between the parent compound with a suitable acid or base to make the acid salt or base salt of the parent compound. Salts of the compounds of the present invention can be synthesized from the parent compounds which contain a basic or acidic moiety by conventional chemical methods. Generally, the salts are prepared by reacting the free base or acid parent compound with stoichiometric amounts or with an excess of the desired salt-forming inorganic or organic acid or base in a suitable solvent or various combinations of solvents.

The term "pharmaceutically acceptable salt" means a salt of a compound of the invention which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. As the compounds of the present invention are useful in both free base and salt form, in practice, the use of the salt form amounts to use of the base form. Lists of suitable salts are found in, e.g., S. M. Birge et al., J. Pharm. Sci., 1977, 66, pp. 1-19, which is hereby incorporated by reference in its entirety The term "pharmaceutically-acceptable acid addition salt" means those salts which retain the biological effectiveness and properties of the free bases and which are not biologically or otherwise undesirable, formed with inorganic acids such as hydrochloric acid, hydrobromic acid, hydroiodic acid, sulfuric acid, sulfamic acid, nitric acid, phosphoric acid, and the like, and organic acids such as acetic acid, trichloroacetic acid, trifluoroacetic acid, adipic acid, alginic acid, ascorbic acid, aspartic acid, benzenesulfonic acid, benzoic acid, 2-acetoxybenzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, heptanoic acid, hexanoic acid, formic acid, fumaric acid, 2-hydroxyethanesulfonic acid (isethionic acid), lactic acid, maleic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, picric acid, pivalic acid, propionic acid, pyruvic acid, pyruvic acid, salicylic acid, stearic acid, succinic acid, sulfanilic acid, tartaric acid, p-toluenesulfonic acid, undecanoic acid, and the like.

The term "pharmaceutically-acceptable base addition salt" means those salts which retain the biological effectiveness and properties of the free acids and which are not biologically or otherwise undesirable, formed with inorganic bases such as ammonia or hydroxide, carbonate, or bicarbonate of ammonium or a metal cation such as sodium, potassium, lithium, calcium, magnesium, iron, zinc, copper, manganese, aluminum, and the like. Particularly preferred are the ammonium, potassium, sodium, calcium, and magnesium salts. Salts derived from pharmaceutically-acceptable organic nontoxic bases include salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins, and the like. Particularly preferred organic nontoxic bases are isopropylamine, diethylamine, ethanolamine, trimethylamine, dicyclohexylamine, choline, and caffeine.

The term "solvate" means a physical association of a compound with one or more solvent molecules or a complex of variable stoichiometry formed by a solute (for example, a compound of Formula (I)) and a solvent, for example, water, ethanol, or acetic acid. This physical association may involve varying degrees of ionic and covalent bonding, including hydrogen bonding. In certain instances, the solvate will be capable of isolation, for example, when one or more solvent molecules are incorporated in the crystal lattice of the crystalline solid. In general, the solvents selected do not interfere with the biological activity of the solute. Solvates encompasses both solution-phase and isolatable solvates. Representative solvates include hydrates, ethanolates, methanolates, and the like.

The term "hydrate" means a solvate wherein the solvent molecule(s) is/are $H_2O$.

The compounds of the present invention as discussed below include the free base or acid thereof, their salts, solvates, and prodrugs and may include oxidized sulfur atoms or quaternized nitrogen atoms in their structure, although not explicitly stated or shown, particularly the pharmaceutically acceptable forms thereof. Such forms, particularly the pharmaceutically acceptable forms, are intended to be embraced by the appended claims.

Pharmaceutical Administration and Diagnostic and Treatment Terms and Conventions The term "patient" includes both human and non-human mammals.

The term "effective amount" means an amount of a compound according to the invention which, in the context of which it is administered or used, is sufficient to achieve the desired effect or result. Depending on the context, the term effective amount may include or be synonymous with a pharmaceutically effective amount or a diagnostically effective amount.

The terms "pharmaceutically effective amount" or "therapeutically effective amount" means an amount of a compound according to the invention which, when administered to a patient in need thereof, is sufficient to effect treatment for disease-states, conditions, or disorders for which the compounds have utility. Such an amount would be sufficient to elicit the biological or medical response of a tissue, system, or patient that is sought by a researcher or clinician. The amount of a compound of according to the invention which constitutes a therapeutically effective amount will vary depending on such factors as the compound and its biological activity, the composition used for administration, the time of administration, the route of administration, the rate of excretion of the compound, the duration of treatment, the type of disease-state or disorder being treated and its severity, drugs used in combination with or coincidentally with the compounds of the invention, and the age, body weight, general health, sex, and diet of the patient. Such a therapeutically effective amount can be determined routinely by one of ordinary skill in the art having regard to their own knowledge, the prior art, and this disclosure.

The term "diagnostically effective amount" means an amount of a compound according to the invention which, when used in a diagnostic method, apparatus, or assay, is sufficient to achieve the desired diagnostic effect or the desired biological activity necessary for the diagnostic method, apparatus, or assay. Such an amount would be sufficient to elicit the biological or medical response in a diagnostic method, apparatus, or assay, which may include a biological or medical response in a patient or in a in vitro or in vivo tissue or system, that is sought by a researcher or clinician. The amount of a compound according to the invention which constitutes a diagnostically effective amount will vary depending on such factors as the compound and its biological activity, the diagnostic method, apparatus, or assay used, the composition used for administration, the time of administration, the route of administration, the rate of excretion of the compound, the duration of administration, drugs and other compounds used in combination with or coincidentally with the compounds of the invention, and, if a patient is the subject of the diagnostic administration, the age, body weight, general health, sex, and diet of the patient. Such a diagnostically effective amount can be determined routinely by one of ordinary skill in the art having regard to their own knowledge, the prior art, and this disclosure.

The terms "treating" or "treatment" mean the treatment of a disease-state in a patient, and include:
(i) preventing the disease-state from occurring in a patient, in particular, when such patient is genetically or otherwise predisposed to the disease-state but has not yet been diagnosed as having it;
(ii) inhibiting or ameliorating the disease-state in a patient, i.e., arresting or slowing its development; or
(iii) relieving the disease-state in a patient, i.e., causing regression or cure of the disease-state.

Methods of Therapeutic Use

As pointed out above, the compounds of the invention are useful in modulating the PIM-2 enzyme function. In doing so, these compounds have therapeutic use in treating disease-states and conditions mediated by the PIM-2 enzyme function or that would benefit from modulation of the PIM-2 function.

As the compounds of the invention modulate the PIM-2 function, they have useful anti-inflammatory and immune-suppressive activity and they can be used in patients as drugs, particularly in the form of pharmaceutical compositions as set forth below, for the treatment of disease-states and conditions. Such disease states and condition include but are not limited to osteoarthritis, reperfusion injury, asthma, chronic obstructive pulmonary disease (COPD), multiple sclerosis, Guillain-Barre syndrome, Crohn's disease, ulcerative colitis, psoriasis, graft versus host disease, systemic lupus erythematosus, rheumatoid arthritis, Alzheimer's disease, toxic shock syndrome, insulin-dependent diabetes mellitis, acute and chronic pain, thermal injury, adult respiratory distress syndrome (ARDS), multiple organ injury secondary to trauma, acute glomerulonephritis, dermatoses with acute inflammatory components, acute purulent meningitis or other central nervous system disorders, Grave's disease, myasthenia gravis, scleroderma and atopic dermatitis. Diseases that can also be treated using the compounds of the invention include cardiovascular disorders such as atherosclerosis, myocardial infarction and stroke. The compounds of the present invention can also be used to treat cancers such as lymphoid-, myeloid- and epithelial-derived malignancies including leukemia, lymphomas and breast, gastric, colorectal, lung, and pancreatic cancers, and cancers such as prostate, chronic lymphocytic leukemia and non-Hodgkin's lymphoma and multiple myeloma. The compounds of the invention can also be used to treat other disorders associated with IKK activation of NF-kB unrelated to those listed above or discussed in the Background of the Invention. For example, the compounds of the invention may also be useful in the treatment of cancer by enhancing the effectiveness of chemotherapeutic agents. Therefore, the invention also provides methods of treating inflammatory and autoimmune diseases, and other diseases including cancer, comprising administering to a patient in need of such treatment a pharmaceutically effect amount of a compound according to the invention.

Methods of Diagnostic Use

The compounds of the invention may also be used in diagnostic applications and for commercial and other purposes as standards in competitive binding assays. In such uses, the compounds of the invention may be used in the form of the compounds themselves or they may be modified by attaching a radioisotope, luminescence, fluorescent label or the like in order to obtain a radioisotope, luminescence, or fluorescent probe, as would be known by one of skill in the art and as outlined in *Handbook of Fluorescent Probes and Research Chemicals*, 6th Edition, R. P. Haugland (ed.), Eugene: Molecular Probes, 1996; *Fluorescence and Luminescence Probes for Biological Activity*, W. T. Mason (ed.), San Diego: Academic Press, 1993; *Receptor-Ligand Interaction, A Practical Approach*, E. C. Hulme (ed.), Oxford: IRL Press, 1992, each of which is hereby incorporated by reference in their entireties.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased inhibitory activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by *Remington: The Science and Practice of Pharmacy*, 20th Edition, A. Gennaro (ed.), Lippincott Williams & Wilkins, 2000; *Handbook of Pharmaceutical Additives*, Michael & Irene Ash (eds.), Gower, 1995; *Handbook of Pharmaceutical Excipients*, A. H. Kibbe (ed.), American Pharmaceutical Ass'n, 2000; H. C. Ansel and N. G. Popovish, *Pharmaceutical Dosage Forms and Drug Delivery Systems*, 5th ed., Lea and Febiger, 1990; each of which is incorporated herein by reference in their entireties to better describe the state of the art.

As one of skill in the art would expect, the forms of the compounds of the invention utilized in a particular pharmaceutical formulation will be selected (e.g., salts) that possess suitable physical characteristics (e.g., water solubility) that is required for the formulation to be efficacious.

Pharmaceutical compositions suitable for buccal (sub-lingual) administration include lozenges comprising a compound of the present invention in a flavored base, usually sucrose, and acacia or tragacanth, and pastilles comprising the compound in an inert base such as gelatin and glycerin or sucrose and acacia.

Pharmaceutical compositions suitable for parenteral administration comprise sterile aqueous preparations of a compound of the present invention. These preparations are preferably administered intravenously, although administration can also be effected by means of subcutaneous, intramuscular, or intradermal injection. Injectable pharmaceutical formulations are commonly based upon injectable sterile saline, phosphate-buffered saline, oleaginous suspensions, or other injectable carriers known in the art and are generally rendered sterile and isotonic with the blood. The injectable pharmaceutical formulations may therefore be provided as a sterile injectable solution or suspension in a nontoxic parenterally acceptable diluent or solvent, including 1,3-butanediol, water, Ringer's solution, isotonic sodium chloride solution, fixed oils such as synthetic mono- or diglycerides, fatty acids such as oleic acid, and the like. Such injectable pharmaceutical formulations are formulated according to the known art using suitable dispersing or setting agents and suspending agents. Injectable compositions will generally contain from 0.1 to 5% w/w of a compound of the invention.

Solid dosage forms for oral administration of the compounds include capsules, tablets, pills, powders, and granules. For such oral administration, a pharmaceutically acceptable composition containing a compound(s) of the invention is formed by the incorporation of any of the normally employed excipients, such as, for example, pharmaceutical grades of mannitol, lactose, starch, pregelatinized starch, magnesium stearate, sodium saccharine, talcum, cellulose ether derivatives, glucose, gelatin, sucrose, citrate, propyl gallate, and the like. Such solid pharmaceutical formulations may include formulations, as are well-known in the art, to provide prolonged or sustained delivery of the drug to the gastrointestinal tract by any number of mechanisms, which include, but are not limited to, pH sensitive release from the dosage form based on the changing pH of the small intestine, slow erosion of a tablet or capsule, retention in the stomach based on the physical properties of the formulation, bioadhesion of the dosage form to the mucosal lining of the intestinal tract, or enzymatic release of the active drug from the dosage form.

Liquid dosage forms for oral administration of the compounds include emulsions, microemulsions, solutions, suspensions, syrups, and elixirs, optionally containing pharmaceutical adjuvants in a carrier, such as, for example, water, saline, aqueous dextrose, glycerol, ethanol and the like. These compositions can also contain additional adjuvants such as wetting, emulsifying, suspending, sweetening, flavoring, and perfuming agents.

Topical dosage forms of the compounds include ointments, pastes, creams, lotions, gels, powders, solutions, sprays, inhalants, eye ointments, eye or ear drops, impregnated dressings and aerosols, and may contain appropriate conventional additives such as preservatives, solvents to assist drug penetration and emollients in ointments and creams. Topical application may be once or more than once per day depending upon the usual medical considerations. Furthermore, preferred compounds for the present invention can be administered in intranasal form via topical use of suitable intranasal vehicles. The formulations may also contain compatible conventional carriers, such as cream or ointment bases and ethanol or oleyl alcohol for lotions. Such carriers may be present as from about 1% up to about 98% of the formulation, more usually they will form up to about 80% of the formulation.

Transdermal administration is also possible. Pharmaceutical compositions suitable for transdermal administration can be presented as discrete patches adapted to remain in intimate contact with the epidermis of the recipient for a prolonged period of time. To be administered in the form of a transdermal delivery system, the dosage administration will, of course, be continuous rather than intermittent throughout the dosage regimen. Such patches suitably contain a compound of the invention in an optionally buffered, aqueous solution, dissolved and/or dispersed in an adhesive, or dispersed in a polymer. A suitable concentration of the active compound is about 1% to 35%, preferably about 3% to 15%.

For administration by inhalation, the compounds of the invention are conveniently delivered in the form of an aerosol spray from a pump spray device not requiring a propellant gas or from a pressurized pack or a nebulizer with the use of a suitable propellant, e.g., dichlorodifluoromethane, trichlorofluoromethane, dichlorotetrafluoroethane, tetrafluoroethane, heptafluoropropane, carbon dioxide, or other suitable gas. In any case, the aerosol spray dosage unit may be determined by providing a valve to deliver a metered amount so that the resulting metered dose inhaler (MDI) is used to administer the compounds of the invention in a reproducible and controlled way. Such inhaler, nebulizer, or atomizer devices are known in the prior art, for example, in PCT International Publication Nos. WO 97/12687 (particularly FIG. 6 thereof, which is the basis for the commercial RESPIMAT® nebulizer); WO 94/07607; WO 97/12683; and WO 97/20590, to which reference is hereby made and each of which is incorporated herein by reference in their entireties.

Rectal administration can be effected utilizing unit dose suppositories in which the compound is admixed with low-melting water-soluble or insoluble solids such as fats, cocoa butter, glycerinated gelatin, hydrogenated vegetable oils, mixtures of polyethylene glycols of various molecular weights, or fatty acid esters of polyethylene glycols, or the like. The active compound is usually a minor component, often from about 0.05 to 10% by weight, with the remainder being the base component.

In all of the above pharmaceutical compositions, the compounds of the invention are formulated with an acceptable carrier or excipient. The carriers or excipients used must, of course, be acceptable in the sense of being compatible with the other ingredients of the composition and must not be deleterious to the patient. The carrier or excipient can be a solid or a liquid, or both, and is preferably formulated with the compound of the invention as a unit-dose composition, for example, a tablet, which can contain from 0.05% to 95% by weight of the active compound. Such carriers or excipients include inert fillers or diluents, binders, lubricants, disintegrating agents, solution retardants, resorption accelerators, absorption agents, and coloring agents. Suitable binders include starch, gelatin, natural sugars such as glucose or β-lactose, corn sweeteners, natural and synthetic gums such as acacia, tragacanth or sodium alginate, carboxymethylcellulose, polyethylene glycol, waxes, and the like. Lubricants include sodium oleate, sodium stearate, magnesium stearate, sodium benzoate, sodium acetate, sodium chloride, and the like. Disintegrators include starch, methyl cellulose, agar, bentonite, xanthan gum, and the like.

Generally, a therapeutically effective daily dose is from about 0.001 mg to about 15 mg/kg of body weight per day of a compound of the invention; preferably, from about 0.1 mg to about 10 mg/kg of body weight per day; and most preferably, from about 0.1 mg to about 1.5 mg/kg of body weight per day. For example, for administration to a 70 kg person, the dosage range would be from about 0.07 mg to about 1050 mg per day of a compound of the invention, preferably from about 7.0 mg to about 700 mg per day, and most preferably from about 7.0 mg to about 105 mg per day. Some degree of routine dose optimization may be required to determine an optimal dosing level and pattern.

Pharmaceutically acceptable carriers and excipients encompass all the foregoing additives and the like.

Examples of Pharmaceutical Formulations

A. TABLETS

| Component | Amount per tablet (mg) |
|---|---|
| active substance | 100 |
| lactose | 140 |
| corn starch | 240 |
| polyvinylpyrrolidone | 15 |
| magnesium stearate | 5 |
| TOTAL | 500 |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

B. TABLETS

| Component | Amount per tablet (mg) |
|---|---|
| active substance | 80 |
| lactose | 55 |
| corn starch | 190 |
| polyvinylpyrrolidone | 15 |
| magnesium stearate | 2 |
| microcrystalline cellulose | 35 |
| sodium-carboxymethyl starch | 23 |
| TOTAL | 400 |

The finely ground active substance, some of the corn starch, lactose, microcrystalline cellulose, and polyvinylpyrrolidone are mixed together, the mixture is screened and worked with the remaining corn starch and water to form a granulate which is dried and screened. The sodium-carboxymethyl starch and the magnesium stearate are added and mixed in and the mixture is compressed to form tablets of a suitable size.

C. COATED TABLETS

| Component | Amount per tablet (mg) |
|---|---|
| active substance | 5 |
| lactose | 30 |
| corn starch | 41.5 |
| polyvinylpyrrolidone | 3 |
| magnesium stearate | 0.5 |
| TOTAL | 90 |

The active substance, corn starch, lactose, and polyvinylpyrrolidone are thoroughly mixed and moistened with water. The moist mass is pushed through a screen with a 1 mm mesh size, dried at about 45° C. and the granules are then passed through the same screen. After the magnesium stearate has been mixed in, convex tablet cores with a diameter of 6 mm are compressed in a tablet-making machine. The tablet cores thus produced are coated in known manner with a covering consisting essentially of sugar and talc. The finished coated tablets are polished with wax.

D. CAPSULES

| Component | Amount per capsule (mg) |
|---|---|
| active substance | 50 |
| corn starch | 268.5 |
| magnesium stearate | 1.5 |
| TOTAL | 320 |

The substance and corn starch are mixed and moistened with water. The moist mass is screened and dried. The dry granules are screened and mixed with magnesium stearate. The finished mixture is packed into size 1 hard gelatine capsules.

E. AMPOULE SOLUTION

| Component | Amount per ampoule |
| --- | --- |
| active substance | 50 mg |
| sodium chloride | 50 mg |
| water for inj. | 5 mL |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilized and sealed by fusion. The ampoules contain 5 mg, 25 mg, and 50 mg of active substance.

F. SUPPOSITORIES

| Component | Amount per suppository (mg) |
| --- | --- |
| active substance | 50 |
| solid fat | 1650 |
| TOTAL | 1700 |

The hard fat is melted. At 40° C., the ground active substance is homogeneously dispersed therein. The mixture is cooled to 38° C. and poured into slightly chilled suppository molds.

G. METERING AEROSOL

| Component | Amount |
| --- | --- |
| active substance | 0.005 |
| sorbitan trioleate | 0.1 |
| monofluorotrichloromethane and difluorodichloromethane (2:3) | to 100 |

The suspension is transferred into a conventional aerosol container with a metering valve. Preferably, 50 μL of suspension are delivered per spray. The active substance may also be metered in higher doses if desired (e.g., 0.02% by weight).

H. POWDER FOR INHALATION

| Component | Amount |
| --- | --- |
| active substance | 1.0 mg |
| lactose monohydrate | to 25 mg |

I. POWDER FOR INHALATION

| Component | Amount |
| --- | --- |
| active substance | 2.0 mg |
| lactose monohydrate | to 25 mg |

J. POWDER FOR INHALATION

| Component | Amount |
| --- | --- |
| active substance | 1.0 mg |
| lactose monohydrate | to 5 mg |

K. POWDER FOR INHALATION

| Component | Amount |
| --- | --- |
| active substance | 2.0 mg |
| lactose monohydrate | to 5 mg |

In Examples H, I, J, and K, the powder for inhalation is produced in the usual way by mixing the individual ingredients together.

PIM-2 Assay Description

The activity of PIM-2 is measured using luciferase-luciferin based ATP detection reagent to quantify ATP depletion resulting from kinase-catalyzed phosphoryl transfer to a peptide substrate. The screen utilizes the Zymark Allegro UHTS system to dispense reagents, buffers and test compounds. To Greiner 384-well, white Lumitrac-200 plates, 20 μL/well of 20 nM PIM-2 (10 nM final assay concentration) in assay buffer (25 mM HEPES, pH 7.5, 10 mM $MgCl_2$, 50 mM KCl, 0.2% CHAPS, 100 μM $Na_3VO_4$, 0.2% BSA and 200 μM TCEP) is delivered, followed by 10 μL/well of test compounds (3 μg/mL final assay concentration in 1% DMSO) that were previously dissolved in DMSO and diluted in assay buffer. A 10 μL volume of a solution containing 4 μM ATP (1 μM final assay concentration) and 20 μM peptide substrate (Biotin-AKRRRLSA, 5 μM final assay concentration) diluted in assay buffer is added to each well and the contents of the wells are mixed. Background wells do not receive PIM-2 but 20 μL/well of assay buffer instead. Positive control wells receive 10 μL/well of assay buffer in lieu of compound. The kinase reaction mixture is incubated for 60 minutes at room temperature. A 40 μL/well of ATP detection reagent is then added to the reaction mixture. The assay plates are read on an Analyst (Molecular Devices) in luminescence mode following additional 15 minutes of incubation at room temperature. Luminescence signals are converted to percent of control (POC) values using the formula: POC=(BCTRL−Signal)÷(BCTRL−PCTRL), where Signal is the test well signal, BCTRL is the average of background control well signals on the plate and PCTRL is the average of positive control well signals on the plate.

The $IC_{50}$ of the compounds is determined with a modification of the above method. The assay is performed in 96-well Lumitrac-200, white, plates. Test compounds dissolved in DMSO (5 mg/mL) are serially diluted 1 to 3 in DMSO for 10-point dose response. The DMSO dilutions are further diluted in the assay buffer and 15 μL of this dilution is added to the assay plate, for a final starting assay concentration of 5 μg/mL in 1% DMSO. A 15 μL volume of 40 nM PIM-2 followed by 30 μL of a solution containing 2 μM ATP and 100 μM peptide substrate, all diluted in assay buffer, is added to each well for a final assay concentration of 10 nM PIM-2, 1 μM ATP, and 50 μM peptide substrate. The kinase reaction mixture is incubated for 15 minutes at room temperature. A 60 μL/well of ATP detection reagent is then added to the reaction mixture. The assay plates are read on an Analyst (Molecular Devices) in luminescence mode following additional 15 minutes of incubation at room temperature. IC$_{50}$ is determined by fitting the POC of the dose response data to a 4-parameter logistic equation.

The invention claimed is:

1. A compound of formula (I)

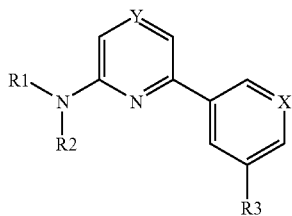

wherein:
X is C
Y is N
R1 is Hydrogen, C1-C3 alkyl,
R2 is Hydrogen, C1-C5 alkyl, C3-C8 cycloalkyl, C3-C8 heterocycloalkyl, each optionally independently substituted with 1-3 R4, wherein R4 is selected from C1-C5 alkyl, C1-C5 alkoxy, carboxamido, acyl, benzyl, C3-C8 cycloalkyl, C3-C8 heterocycloalkyl, hydroxyl and amino optionally mono or disubstituted with C1-C4 alkyl;
wherein each R4 is optionally independently substituted with 1-3 substituents selected from C1-C5 alkyl C1-C5 alkoxy, acyl, benzyl, C3-C8 cycloalkyl, C3-C8 heterocycloalkyl, hydroxyl and amino optionally mono or disubstituted with C1-C4 alkyl
or;
wherein R1 and R2 together with the nitrogen atom to which they are attached form a C3-C8 ring containing 1-3 heteroatoms and which is optionally substituted by 1-3 R5, wherein R5 is selected from C1-C5 alkyl, C1-C5 alkoxy, carboxamido, acyl, benzyl, C3-C8 cycloalkyl, C3-C8 heterocycloalkyl, hydroxyl, and amino optionally mono or disubstituted with C1-C4 alkyl; wherein each R5 is optionally independently substituted by with substituents selected from hydroxyl, C1-C5 alkoxy, or amino optionally mono or disubstituted with C1-C4 alkyl;
R3 is

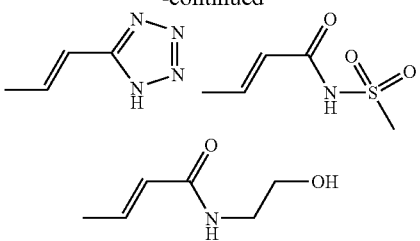

or a pharmaceutically acceptable salts thereof.

2. A compound according to formula (I) of claim 1 wherein:
X is C
Y is N
R1 is Hydrogen, C1-C3 alkyl
R2 is C1-C5 alkyl, C3-C8 cycloalkyl, C3-C8 heterocycloalkyl, each optionally independently substituted with 1-3 R4, wherein R4 is selected from C1-C5 alkyl, C1-C5 alkoxy, carboxamido, benzyl, C3-C8 cycloalkyl, C3-C8 heterocycloalkyl, hydroxyl and amino optionally mono or disubstituted with C1-C4 alkyl;
wherein each R4 is optionally independently substituted with 1-3 substituents selected from C1-C5 alkyl, C1-C5 alkoxy, acyl, benzyl, hydroxyl and amino optionally mono or disubstituted with C1-C4 alkyl
or;
wherein R1 and R2 together with the nitrogen atom to which they are attached form a
C3-C8 ring containing 1-3 heteroatoms and which is optionally substituted by 1-3 R5, wherein R5 is selected from C1-C5 alkyl, C1-C5 alkoxy, carboxamido, acyl, benzyl, hydroxyl and amino optionally mono or disubstituted with C1-C4 alkyl; wherein each R5 is optionally independently substituted with substituents selected from hydroxyl, C1-C5 alkoxy, or amino optionally mono or disubstituted with C1-C4 alkyl

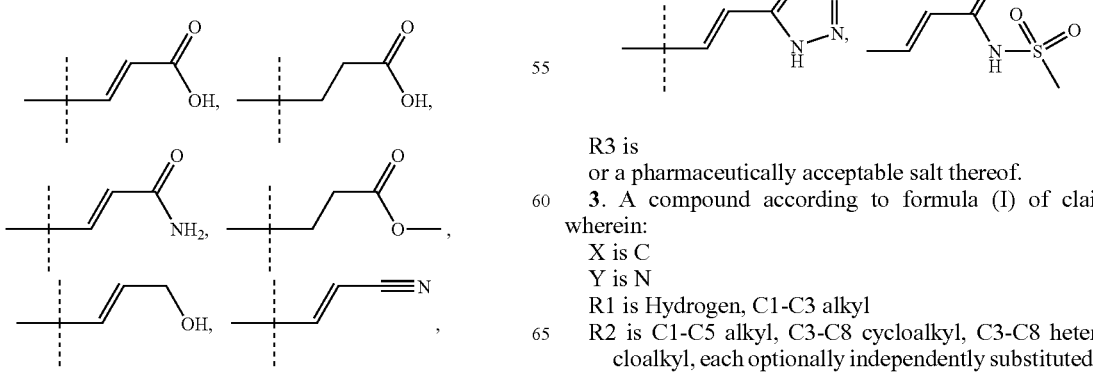

R3 is
or a pharmaceutically acceptable salt thereof.

3. A compound according to formula (I) of claim 1 wherein:
X is C
Y is N
R1 is Hydrogen, C1-C3 alkyl
R2 is C1-C5 alkyl, C3-C8 cycloalkyl, C3-C8 heterocycloalkyl, each optionally independently substituted with 1-3 R4, wherein R4 is selected from C1-C5 alkyl, C1-C5 alkoxy, carboxamido, benzyl, C3-C8 cycloalkyl, C3-C8 heterocycloalkyl, hydroxyl and amino optionally mono or disubstituted with C1-C4 alkyl;

wherein each R4 is optionally independently substituted with 1-3 substituents selected from C1-C5 alkyl, C1-C5 alkoxy, benzyl, hydroxyl and amino optionally mono or disubstituted with C1-C4 alkyl or;

wherein R1 and R2 together with the nitrogen atom to which they are attached form a C3-C8 ring containing 1-3 heteroatoms and which is optionally substituted by 1-3 R5, wherein R5 is selected from C1-C5 alkyl, C1-C5 alkoxy, carboxamido, benzyl, hydroxyl and amino optionally mono or disubstituted with C1-C4 alkyl; wherein each R5 is optionally independently substituted with substituents selected from hydroxyl, C1-C5 alkoxy, or amino optionally mono or disubstituted with C1-C4 alkyl

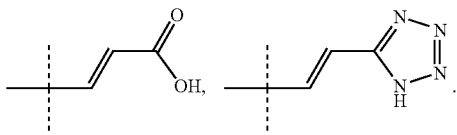

R3 is
or a pharmaceutically acceptable salts thereof.

4. A compound according to formula (I) of claim 1 wherein:
X is C
Y is N
R1 is Hydrogen, C1-C3 alkyl
R2 is C1-C5 alkyl, C3-C8 cycloalkyl, each optionally independently substituted with 1-3 R4, wherein R4 is selected from carboxamido, C3-C8 heterocycloalkyl, hydroxyl and amino optionally mono or disubstituted with C1-C4 alkyl;

or;

wherein R1 and R2 together with the nitrogen atom to which they are attached form a C3-C8 ring containing 1-3 heteroatoms and which is optionally substituted by 1-3 R5, wherein R5 is selected from C1-C3 alkyl, benzyl and amino optionally mono or disubstituted with C1-C4 alkyl; wherein each R5 is optionally independently substituted with amino optionally mono or disubstituted with C1-C4 alkyl R3 is

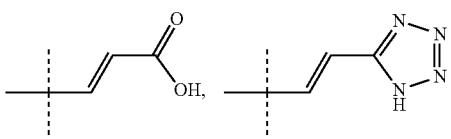

5. A method of treating cancer said method comprised of the step of administering to a patient in need thereof a therapeutic amount of a compound according to claim 1 of a pharmaceutically acceptable salt thereof, wherein the cancer is selected from the list consisting of prostate, chronic lymphocytic leukemia and non-Hodgkin's lymphoma and multiple myeloma.

6. A pharmaceutical composition comprising a therapeutically effective amount of a compound according to claim 1.

7. A process for preparing a compound according to claim 1 wherein said process is comprised of the steps of Scheme 1 combining a 2,6-dichloropyrazine or 2,6-dichloropyridine (II) with an amine in a suitable solvent to form a product (IV);
b) treating product (IV) with a reagent (V) and additional reagents required for Suzuki coupling to provide product (I)
c) modifying R$_1$ or R$_2$, such as by protection/deprotection; wherein (X=C, Y=N, C).

8. A compound chosen from:

| Cpd # | Structure | name |
|---|---|---|
| 1 | 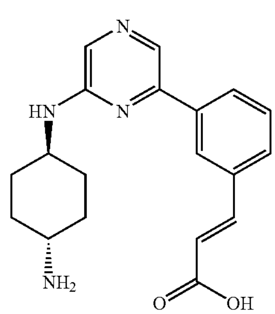 | (E)-3-{3-[6-(4-Amino-cyclohexylamino)-pyrazin-2-yl]-phenyl}-acrylic acid |

-continued
| Cpd # | Structure | name |
|---|---|---|
| 2 | 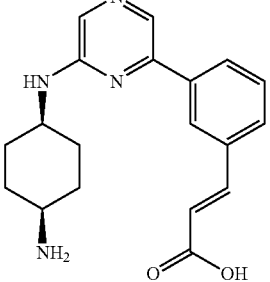 | (E)-3-{3-[6-(4-Amino-cyclohexylamino)-pyrazin-2-yl]-phenyl}-acrylic acid |
| 3 | 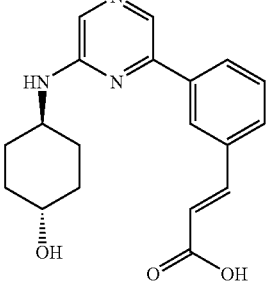 | (E)-3-{3-[6-(4-Hydroxy-cyclohexylamino)-pyrazin-2-yl]-phenyl}-acrylic acid |
| 4 | 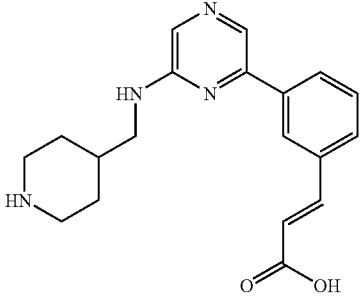 | (E)-3-(3-{6-[(Piperidin-4-ylmethyl)-amino]-pyrazin-2-yl}-phenyl)-acrylic acid |
| 5 | 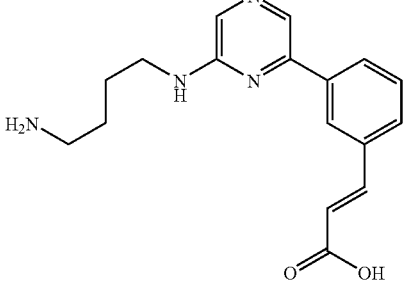 | (E)-3-{3-[6-(4-Amino-butylamino)-pyrazin-2-yl]-phenyl}-acrylic acid |
| 6 | 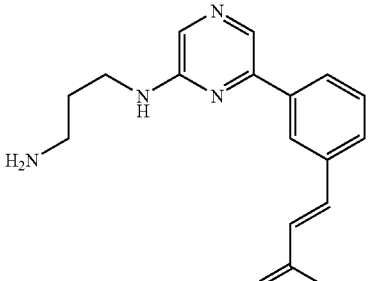 | (E)-3-{3-[6-(3-Amino-propylamino)-pyrazin-2-yl]-phenyl}-acrylic acid |

| Cpd # | Structure | name |
|---|---|---|
| 7 | 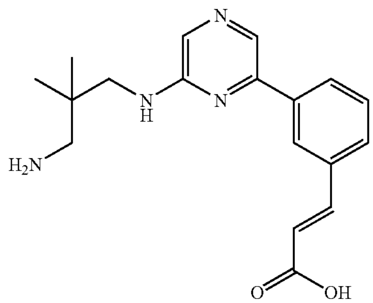 | (E)-3-{3-[6-(3-Amino-2,2-dimethyl-propylamino)-pyrazin-2-yl]-phenyl}-acrylic acid |
| 8 | 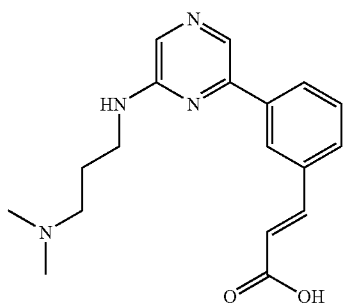 | (E)-3-{3-[6-(3-Dimethylamino-propylamino)-pyrazin-2-yl]-phenyl}-acrylic acid |
| 9 | 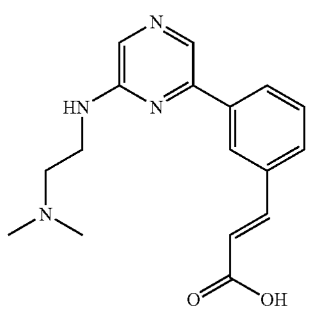 | (E)-3-{3-[6-(2-Dimethylamino-ethylamino)-pyrazin-2-yl]-phenyl}-acrylic acid |
| 10 | 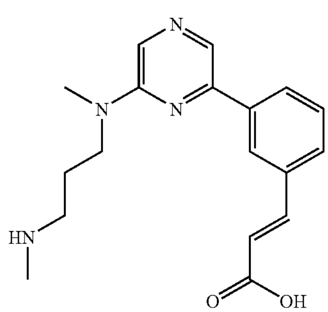 | (E)-3-(3-{6-[Methyl-(3-methylamino-propyl)-amino]-pyrazin-2-yl}-phenyl)-acrylic acid |
| 11 | 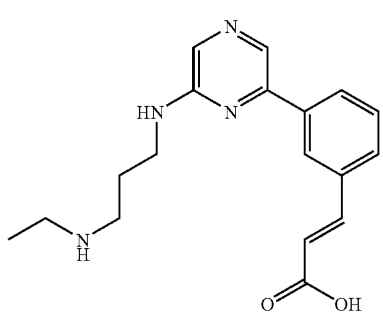 | (E)-3-{3-[6-(3-Ethylamino-propylamino)-pyrazin-2-yl]-phenyl}-acrylic acid |

| Cpd # | Structure | name |
|---|---|---|
| 12 | 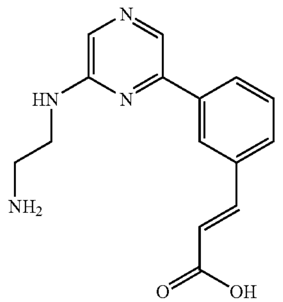 | (E)-3-{3-[6-(2-Amino-ethylamino)-pyrazin-2-yl]-phenyl}-acrylic acid |
| 13 | 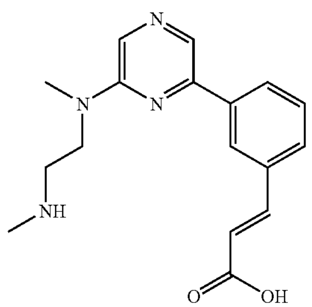 | (E)-3-(3-{6-[Methyl-(2-methylamino-ethyl)-amino]-pyrazin-2-yl}-phenyl)-acrylic acid |
| 14 | 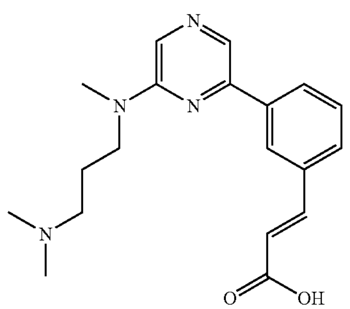 | (E)-3-(3-{6-[(3-Dimethylamino-propyl)-methyl-amino]-pyrazin-2-yl}-phenyl)-acrylic acid |
| 15 | 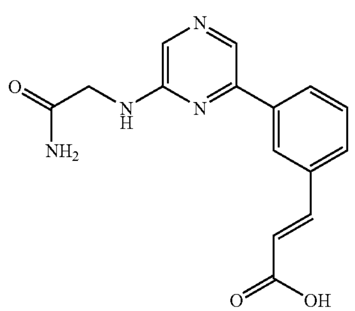 | (E)-3-{3-[6-(Carbamoylmethyl-amino)-pyrazin-2-yl]-phenyl}-acrylic acid |
| 16 | 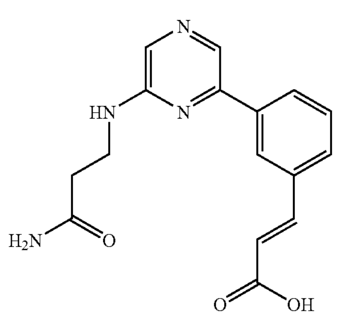 | (E)-3-{3-[6-(2-Carbamoyl-ethylamino)-pyrazin-2-yl]-phenyl}-acrylic acid; MS, electrospray |

-continued

| Cpd # | Structure | name |
|---|---|---|
| 17 | 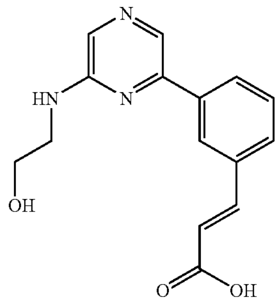 | (E)-3-{3-[6-(2-Hydroxy-ethylamino)-pyrazin-2-yl]-phenyl}-acrylic acid |
| 18 | 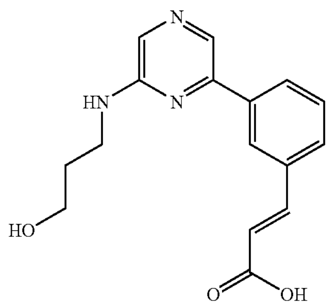 | E)-3-{3-[6-(3-Hydroxy-propylamino)-pyrazin-2-yl]-phenyl}-acrylic acid |
| 19 | 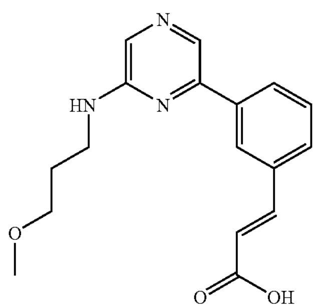 | (E)-3-{3-[6-(3-Methoxy-propylamino)-pyrazin-2-yl]-phenyl}-acrylic acid |
| 20 | 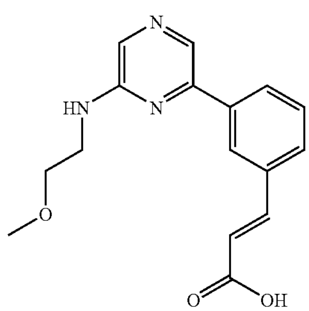 | (E)-3-{3-[6-(2-Methoxy-ethylamino)-pyrazin-2-yl]-phenyl}-acrylic acid |
| 21 | 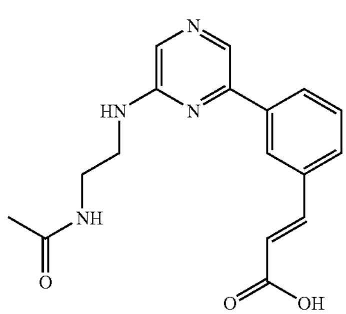 | (E)-3-{3-[6-(2-Acetylamino-ethylamino)-pyrazin-2-yl]-phenyl}-acrylic acid |

-continued

| Cpd # | Structure | name |
|---|---|---|
| 22 | 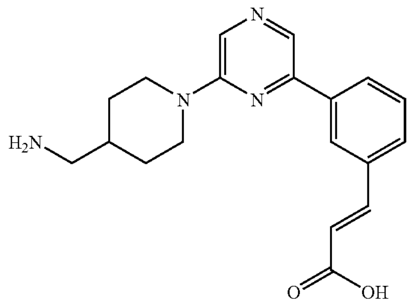 | (E)-3-{3-[6-(4-Aminomethyl-piperidin-1-yl)-pyrazin-2-yl]-phenyl}-acrylic acid |
| 23 | 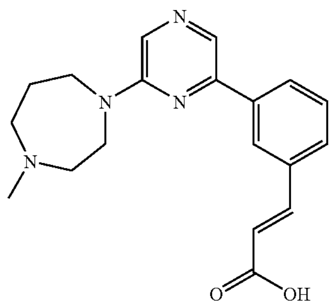 | (E)-3-{3-[6-(4-Methyl-[1,4]diazepan-1-yl)-pyrazin-2-yl]-phenyl}-acrylic acid |
| 24 | 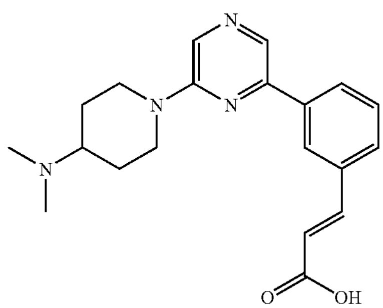 | (E)-3-{3-[6-(4-Dimethylamino-piperidin-1-yl)-pyrazin-2-yl]-phenyl}-acrylic acid |
| 25 | 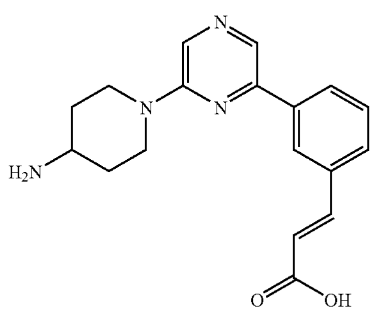 | Preparation of 14 (E)-3-{3-[6-(4-Amino-piperidin-1-yl)-pyrazin-2-yl]-phenyl}-acrylic acid |
| 26 | 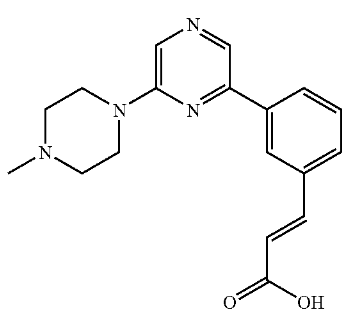 | (E)-3-[3-(4-Methyl-3,4,5,6-tetrahydro-2H-[1,2']bipyrazinyl-6'-yl)-phenyl]-acrylic acid |

| Cpd # | Structure | name |
|---|---|---|
| 27 | 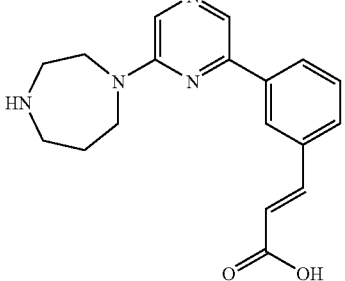 | (E)-3-[3-(6-[1,4]Diazepan-1-yl-pyrazin-2-yl)-phenyl]-acrylic acid |
| 28 | 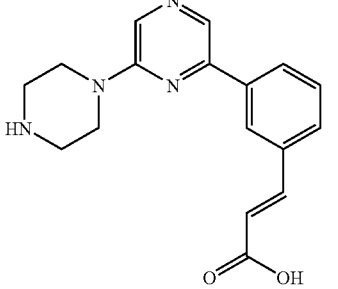 | (E)-3-[3-(3,4,5,6-Tetrahydro-2H-[1,2']bipyrazinyl-6'-yl)-phenyl]-acrylic acid |
| 29 | 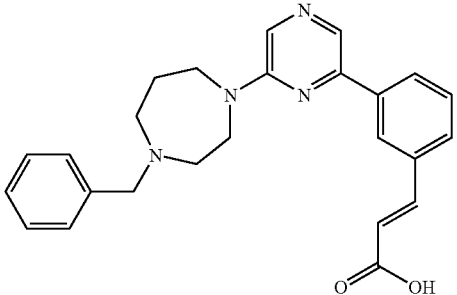 | (E)-3-{3-[6-(4-Benzyl-[1,4]diazepan-1-yl)-pyrazin-2-yl]-phenyl}-acrylic acid |
| 30 | 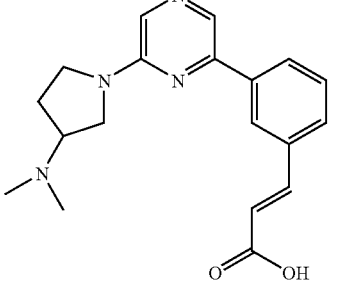 | (E)-3-{3-[6-(3-Dimethylamino-pyrrolidin-1-yl)-pyrazin-2-yl]-phenyl}-acrylic acid |
| 31 | 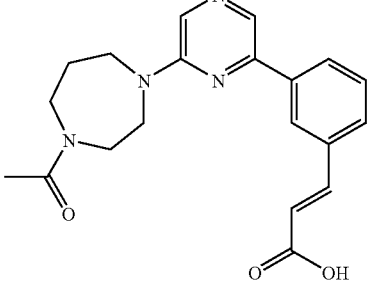 | (E)-3-{3-[6-(4-Acetyl-[1,4]diazepan-1-yl)-pyrazin-2-yl]-phenyl}-acrylic acid |

| Cpd # | Structure | name |
|---|---|---|
| 32 | 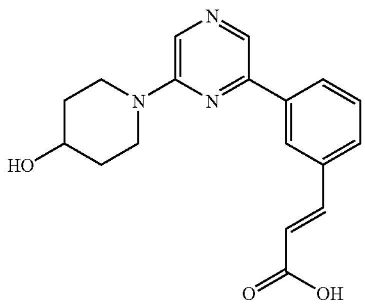 | (E)-3-{3-[6-(4-Hydroxy-piperidin-1-yl)-pyrazin-2-yl]-phenyl}-acrylic acid |
| 33 | 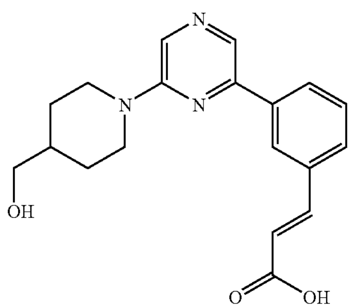 | (E)-3-{3-[6-(4-Hydroxymethyl-piperidin-1-yl)-pyrazin-2-yl]-phenyl}-acrylic acid |
| 34 | 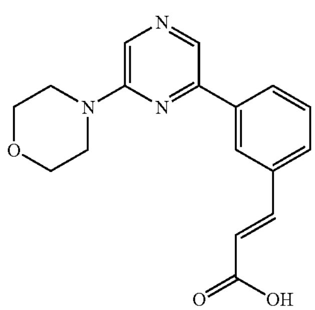 | (E)-3-[3-(6-Morpholin-4-yl-pyrazin-2-yl)-phenyl]-acrylic acid |
| 35 | 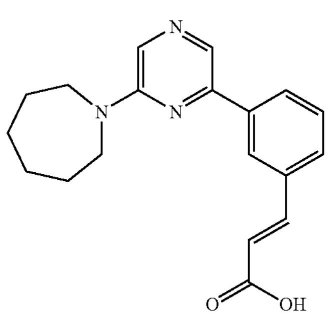 | (E)-3-[3-(6-Azepan-1-yl-pyrazin-2-yl)-phenyl]-acrylic acid |
| 36 | | |
| 37 | | |

-continued

| Cpd # | Structure | name |
|---|---|---|
| 38 | 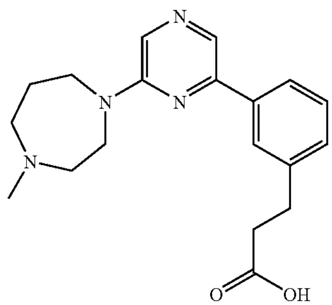 | 3-{3-[6-(4-Methyl-[1,4]diazepam-1-yl)-pyrazin-2-yl]-phenyl}-propionic acid |
| 39 | 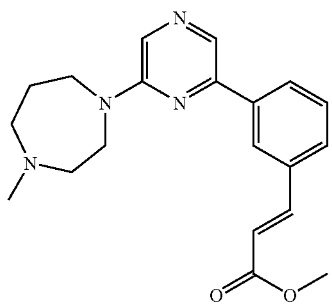 | (E)-3-{3-[6-(4-Methyl-[1,4]diazepan-1-yl)-pyrazin-2-yl]-phenyl}-acrylic acid methyl ester |
| 40 | 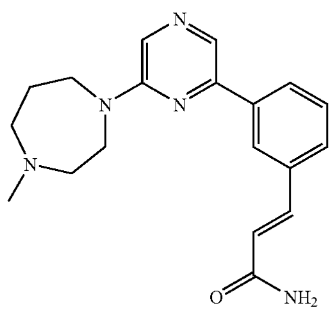 | (E)-3-{3-[6-(4-Methyl-[1,4]diazepan-1-yl)-pyrazin-2-yl]-phenyl}-acrylamide |
| 41 | 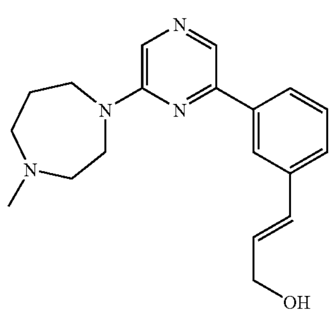 | (E)-3-{3-[6-(4-Methyl-[1,4]diazepan-1-yl)-pyrazin-2-yl]-phenyl}-prop-2-en-1-ol |
| 42 | 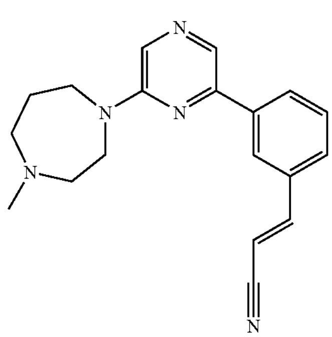 | (E)-3-{3-[6-(4-Methyl-[1,4]diazepan-1-yl)-pyrazin-2-yl]-phenyl}-acrylonitrile |

-continued

| Cpd # | Structure | name |
|---|---|---|
| 43 | 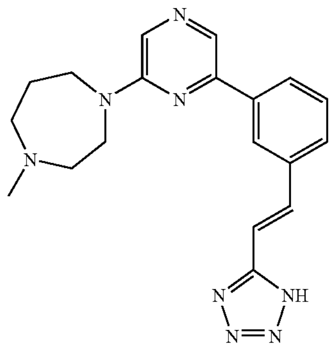 | 1-Methyl-4-(6-{3-[(E)-2-(1H-tetrazol-5-yl)-vinyl]-phenyl}-pyrazin-2-yl)-[1,4]diazepane |
| 44 | 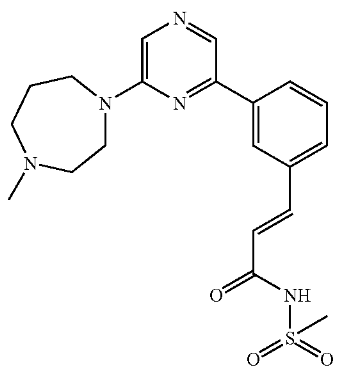 | N-((E)-3-{3-[6-(4-Methyl-perhydro-1,4-diazepin-1-yl)-pyrazin-2-yl]-phenyl}-acryloyl)-methanesulfonamide |
| 45 | 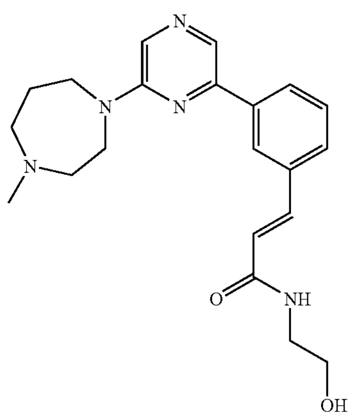 | (E)-N-(2-Hydroxy-ethyl)-3-{3-[6-(4-methyl-perhydro-1,4-diazepin-1-yl)-pyrazin-2-yl]-phenyl}-acrylamide |
| 46 | | |
| 47 | | |
| 48 | | |
| 49 | | |
| 50 | | |
| 51 | | |
| 52 | | |
| 53 | | |
| 54 | | |
| 55 | | |
| 56 | | |
| 57 | | |
| 58 | | |
| 59 | | |
| 60 | | |
| 61 | | |
| 62 | | |
| 63 | | |
| 64 | | |
| 65 | | |
| 66 | | |

| Cpd # | Structure | name |
|---|---|---|
| 67 | | |
| 68 | | |
| 69 | | |
| 70 | | |
| 71 | | |
| 72 | | |
| 73 | | |
| 74 | | |
| 75 | | |
| 76 | | |
| 77 | | |
| 78 | | |
| 79 | | |
| 80 | 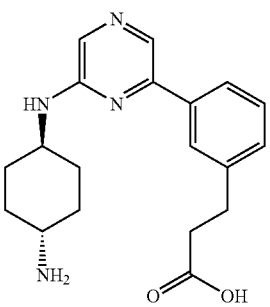 | 3-{3-[6-(4-Amino-cyclohexylamino)-pyrazin-2-yl]-phenyl}-propionic acid |
| 81 | 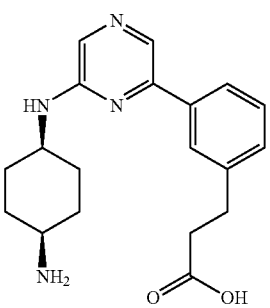 | 3-{3-[6-(4-Amino-cyclohexylamino)-pyrazin-2-yl]-phenyl}-propionic acid |
| 82 | 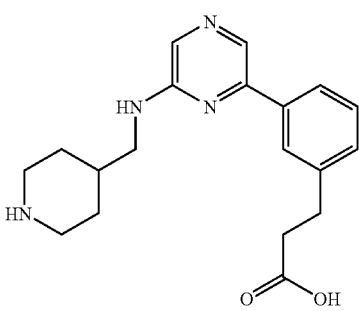 | 3-(3-{6-[(Piperidin-4-ylmethyl)-amino]-pyrazin-2-yl}-phenyl)-propionic acid |
| 83 | 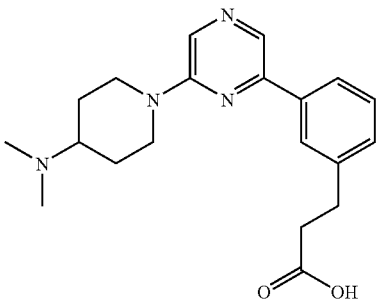 | 3-{3-[6-(4-Dimethylamino-piperidin-1-yl)-pyrazin-2-yl]-phenyl}-propionic acid |

| Cpd # | Structure | name |
|---|---|---|
| 84 | 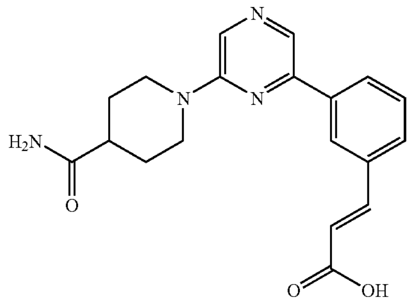 | (E)-3-{3-[6-(4-Carbamoyl-piperidin-1-yl)-pyrazin-2-yl]-phenyl}-acrylic acid |
| 85 | 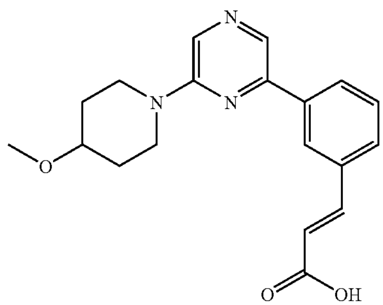 | (E)-3-{3-[6-(4-Methoxy-piperidin-1-yl)-pyrazin-2-yl]-phenyl}-acrylic acid |
| 86 | 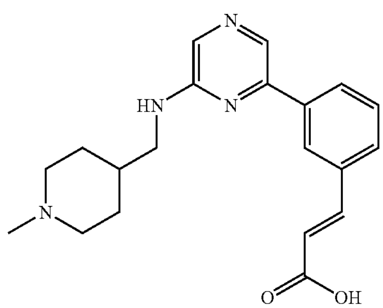 | (E)-3-(3-{6-[(1-Methyl-piperidin-4-ylmethyl)-amino]-pyrazin-2-yl}-phenyl)-acrylic acid |
| 87 | 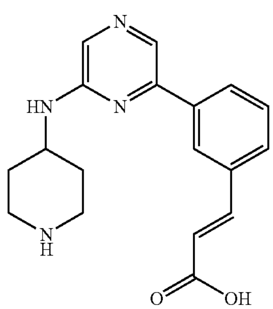 | (E)-3-{3-[6-(Piperidin-4-ylamino)-pyrazin-2-yl]-phenyl}-acrylic acid |
| 88 | 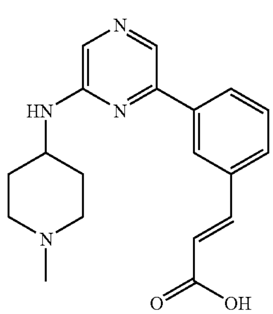 | (E)-3-{3-[6-(1-Methyl-piperidin-4-ylamino)-pyrazin-2-yl]-phenyl}-acrylic acid |

| Cpd # | Structure | name |
|---|---|---|
| 89 | 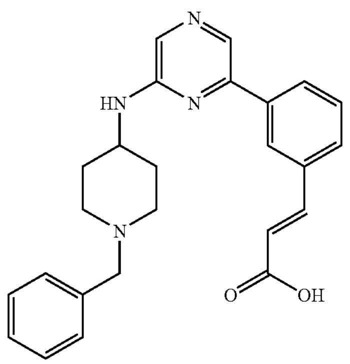 | (E)-3-{3-[6-(1-Benzyl-piperidin-4-ylamino)-pyrazin-2-yl]-phenyl}-acrylic acid |
| 90 | 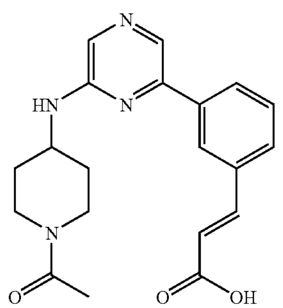 | (E)-3-{3-[6-(1-Acetyl-piperidin-4-ylamino)-pyrazin-2-yl]-phenyl}-acrylic acid |
| 91 | 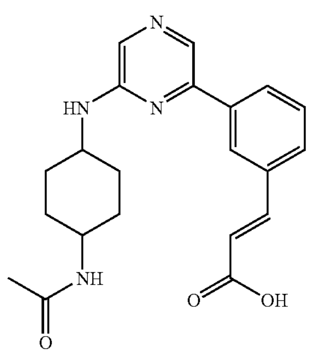 | (E)-3-{3-[6-(4-Acetylamino-cyclohexylamino)-pyrazin-2-yl]-phenyl}-acrylic acid |
| 92 | 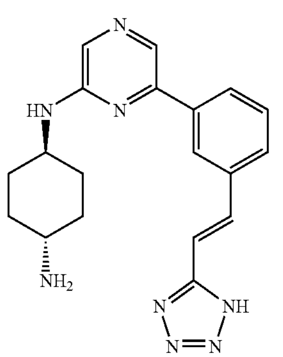 | N-(6-{3-[(E)-2-(1H-Tetrazol-5-yl)-vinyl]-phenyl}-pyrazin-2-yl)-cyclohexane-1,4-diamine |

| Cpd # | Structure | name |
|---|---|---|
| 93 | 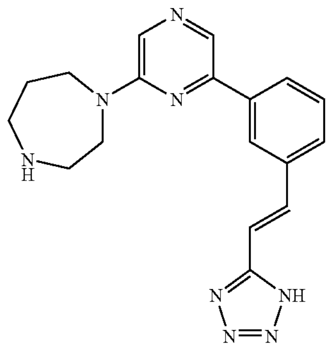 | 4-(6-{3-[(E)-2-(1H-tetrazol-5-yl)-vinyl]-phenyl}-pyrazin-2-yl)-[1,4]diazepane |
| 94 | 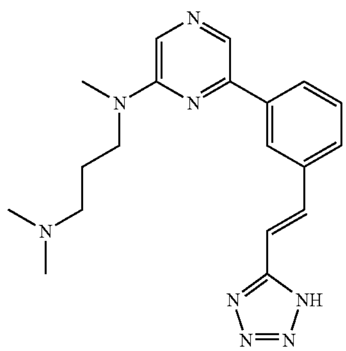 | N,N,N'-Trimethyl-N'-(6-{3-[(E)-2-(1H-tetrazol-5-yl)-vinyl]-phenyl}-pyrazin-2-yl)-propane-1,3-diamine |
| 95 | 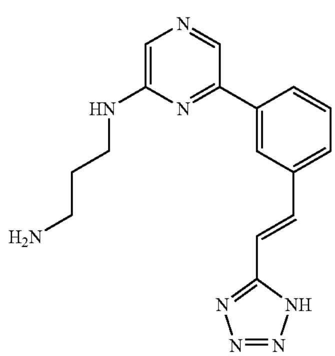 | $N^1$-(6-{3-[(E)-2-(1H-Tetrazol-5-yl)-vinyl]-phenyl}-pyrazin-2-yl)-propane-1,3-diamine |
| 96 | | |
| 97 | | |
| 98 | | | or the pharmaceutically acceptable salts thereof.

9. A compound of claim 8 chosen from

| Cpd # | Structure | name |
|---|---|---|
| 1 | 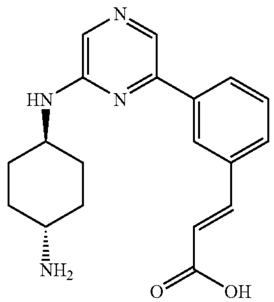 | (E)-3-{3-[6-(4-Amino-cyclohexylamino)-pyrazin-2-yl]-phenyl}-acrylic acid |
| 2 | 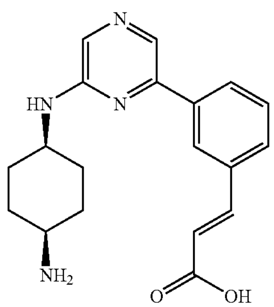 | (E)-3-{3-[6-(4-Amino-cyclohexylamino)-pyrazin-2-yl]-phenyl}-acrylic acid |
| 3 | 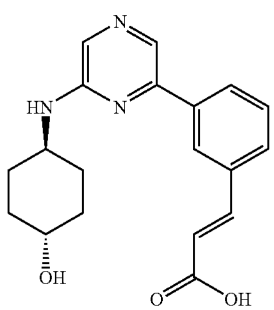 | (E)-3-{3-[6-(4-Hydroxy-cyclohexylamino)-pyrazin-2-yl]-phenyl}-acrylic acid |
| 4 | 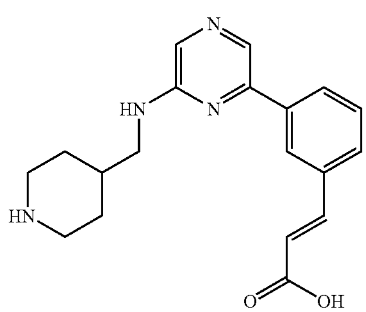 | (E)-3-(3-{6-[(Piperidin-4-ylmethyl)-amino]-pyrazin-2-yl}-phenyl)-acrylic acid |
| 5 | 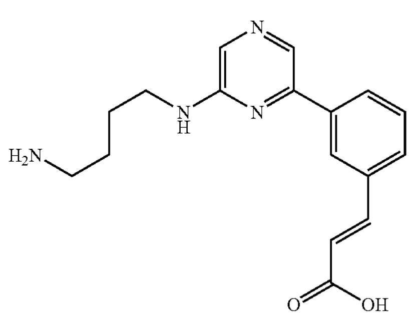 | (E)-3-{3-[6-(4-Amino-butylamino)-pyrazin-2-yl]-phenyl}-acrylic acid |

-continued
| Cpd # | Structure | name |
|---|---|---|
| 6 | 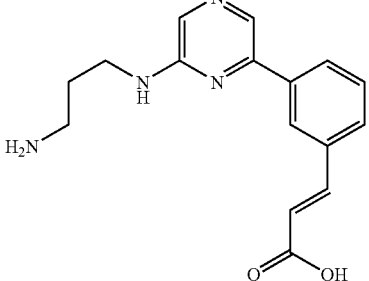 | (E)-3-{3-[6-(3-Amino-propylamino)-pyrazin-2-yl]-phenyl}-acrylic acid |
| 7 | 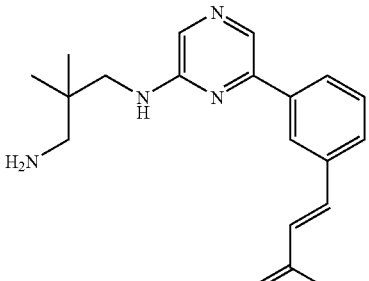 | (E)-3-{3-[6-(3-Amino-2,2-dimethyl-propylamino)-pyrazin-2-yl]-phenyl}-acrylic acid |
| 8 | 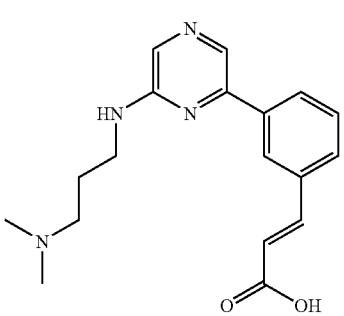 | (E)-3-{3-[6-(3-Dimethylamino-propylamino)-pyrazin-2-yl]-phenyl}-acrylic acid |
| 9 | 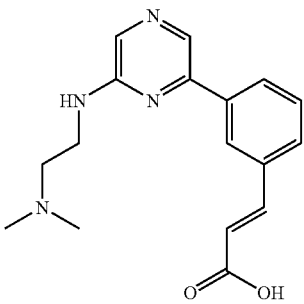 | (E)-3-{3-[6-(2-Dimethylamino-ethylamino)-pyrazin-2-yl]-phenyl}-acrylic acid |
| 10 | 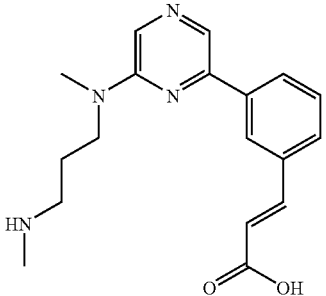 | (E)-3-(3-{6-[Methyl-(3-methylamino-propyl)-amino]-pyrazin-2-yl}-phenyl)-acrylic acid |

| Cpd # | Structure | name |
|---|---|---|
| 11 | 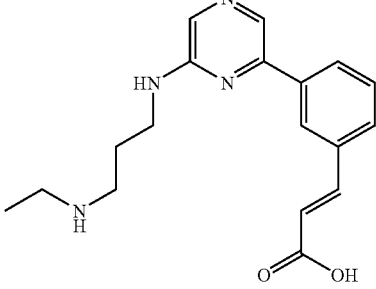 | (E)-3-{3-[6-(3-Ethylamino-propylamino)-pyrazin-2-yl]-phenyl}-acrylic acid |
| 12 | 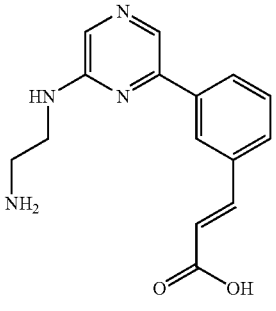 | (E)-3-{3-[6-(2-Amino-ethylamino)-pyrazin-2-yl]-phenyl}-acrylic acid |
| 13 | 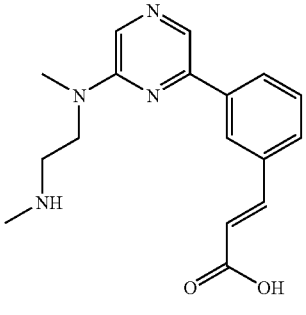 | (E)-3-(3-{6-[Methyl-(2-methylamino-ethyl)-amino]-pyrazin-2-yl}-phenyl)-acrylic acid |
| 14 | 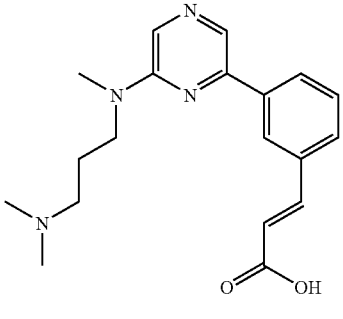 | (E)-3-(3-{6-[(3-Dimethylamino-propyl)-methyl-amino]-pyrazin-2-yl}-phenyl)-acrylic acid |
| 15 | 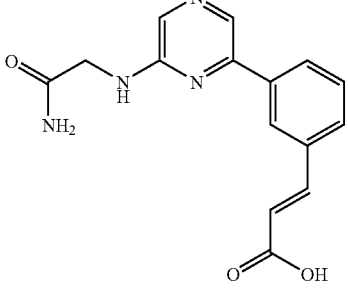 | (E)-3-{3-[6-(Carbamoylmethyl-amino)-pyrazin-2-yl]-phenyl}-acrylic acid |

| Cpd # | Structure | name |
|---|---|---|
| 16 | 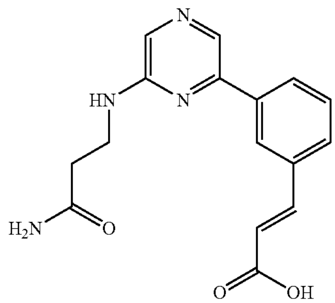 | (E)-3-{3-[6-(2-Carbamoyl-ethylamino)-pyrazin-2-yl]-phenyl}-acrylic acid; MS, electrospray |
| 17 | 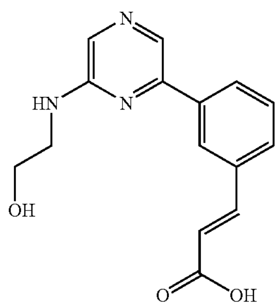 | (E)-3-{3-[6-(2-Hydroxy-ethylamino)-pyrazin-2-yl]-phenyl}-acrylic acid |
| 18 | 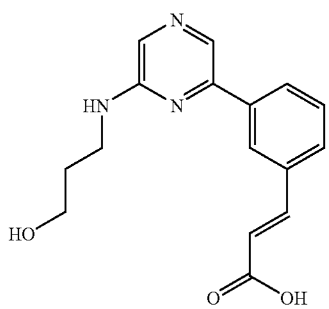 | E)-3-{3-[6-(3-Hydroxy-propylamino)-pyrazin-2-yl]-phenyl}-acrylic acid |
| 19 | 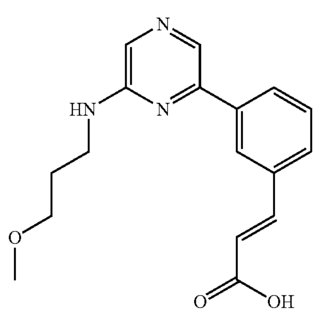 | (E)-3-{3-[6-(3-Methoxy-propylamino)-pyrazin-2-yl]-phenyl}-acrylic acid |
| 20 | 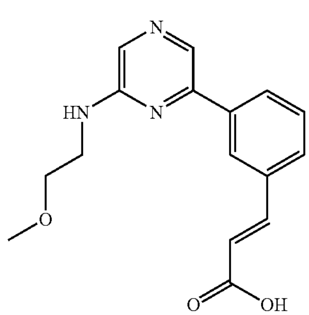 | (E)-3-{3-[6-(2-Methoxy-ethylamino)-pyrazin-2-yl]-phenyl}-acrylic acid |

-continued
| Cpd # | Structure | name |
|---|---|---|
| 21 | 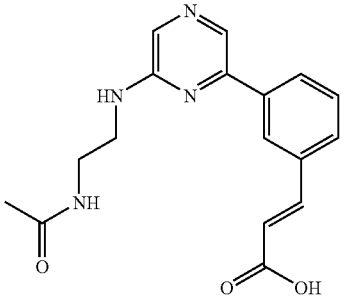 | (E)-3-{3-[6-(2-Acetylamino-ethylamino)-pyrazin-2-yl]-phenyl}-acrylic acid |
| 22 | 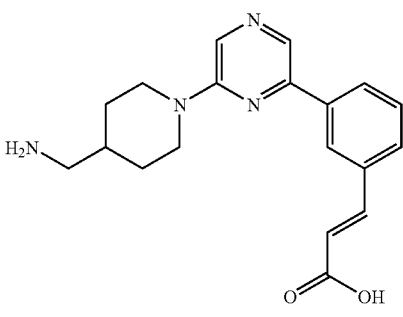 | (E)-3-{3-[6-(4-Aminomethyl-piperidin-1-yl)-pyrazin-2-yl]-phenyl}-acrylic acid |
| 23 | 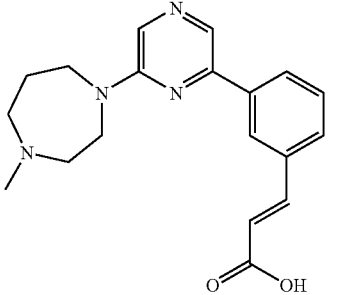 | (E)-3-{3-[6-(4-Methyl-[1,4]diazepan-1-yl)-pyrazin-2-yl]-phenyl}-acrylic acid |
| 24 | 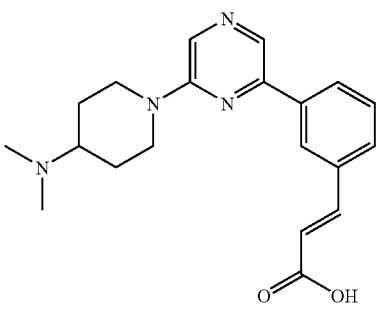 | (E)-3-{3-[6-(4-Dimethylamino-piperidin-1-yl)-pyrazin-2-yl]-phenyl}-acrylic acid |
| 25 | 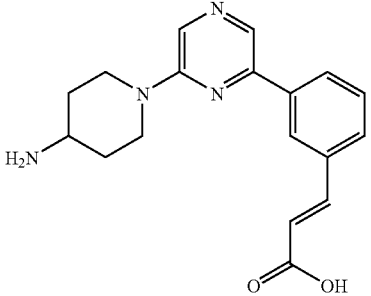 | Preparation of 14 (E)-3-{3-[6-(4-Amino-piperidin-1-yl)-pyrazin-2-yl]-phenyl}-acrylic acid |

-continued

| Cpd # | Structure | name |
|---|---|---|
| 26 | 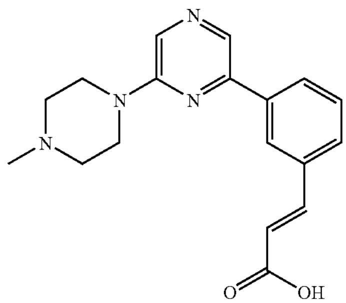 | (E)-3-[3-(4-Methyl-3,4,5,6-tetrahydro-2H-[1,2']bipyrazinyl-6'-yl)-phenyl]-acrylic acid |
| 27 | 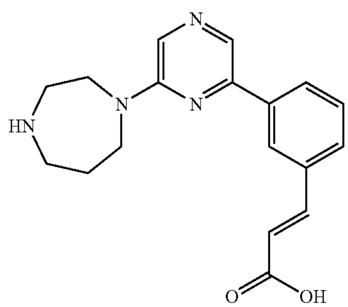 | (E)-3-[3-(6-[1,4]Diazepan-1-yl-pyrazin-2-yl)-phenyl]-acrylic acid |
| 28 | 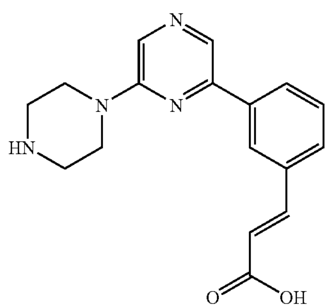 | (E)-3-[3-(3,4,5,6-Tetrahydro-2H-[1,2']bipyrazinyl-6'-yl)-phenyl]-acrylic acid |
| 29 | 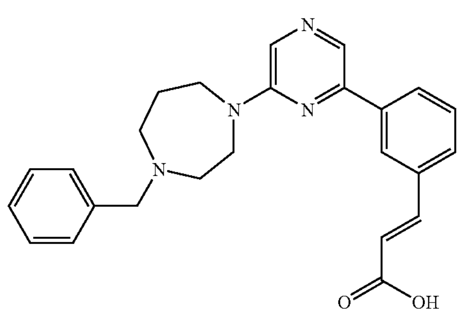 | (E)-3-{3-[6-(4-Benzyl-[1,4]diazepan-1-yl)-pyrazin-2-yl]-phenyl}-acrylic acid |
| 30 | 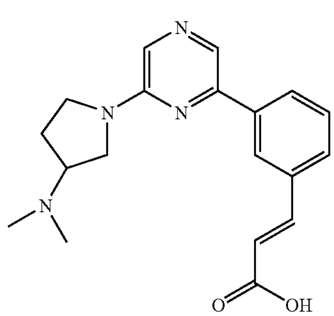 | (E)-3-{3-[6-(3-Dimethylamino-pyrrolidin-1-yl)-pyrazin-2-yl]-phenyl}-acrylic acid |

-continued
| Cpd # | Structure | name |
|---|---|---|
| 31 | 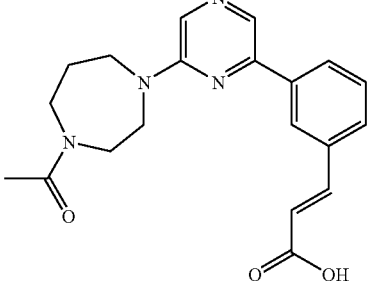 | (E)-3-{3-[6-(4-Acetyl-[1,4]diazepan-1-yl)-pyrazin-2-yl]-phenyl}-acrylic acid |
| 32 | 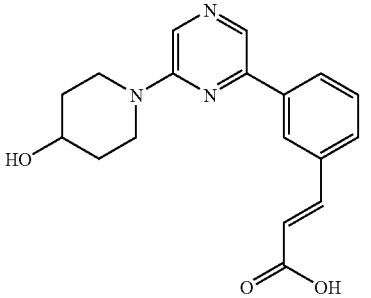 | (E)-3-{3-[6-(4-Hydroxy-piperidin-1-yl)-pyrazin-2-yl]-phenyl}-acrylic acid |
| 33 | 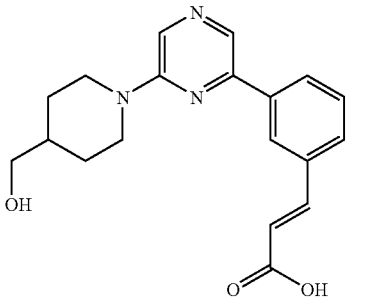 | (E)-3-{3-[6-(4-Hydroxymethyl-piperidin-1-yl)-pyrazin-2-yl]-phenyl}-acrylic acid |
| 34 | 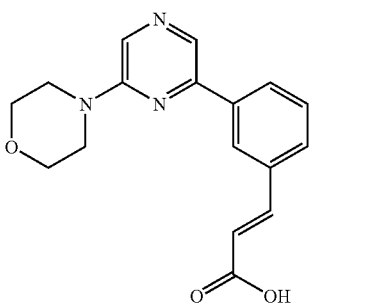 | (E)-3-[3-(6-Morpholin-4-yl-pyrazin-2-yl)-phenyl]-acrylic acid |
| 35 | 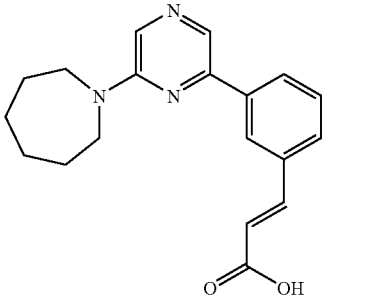 | (E)-3-[3-(6-Azepan-1-yl-pyrazin-2-yl)-phenyl]-acrylic acid |
| 36 | | |

| Cpd # | Structure | name |
|---|---|---|
| 37 | | |
| 38 | 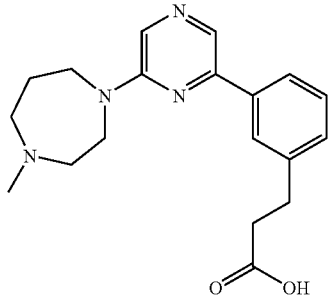 | 3-{3-[6-(4-Methyl-[1,4]diazepam-1-yl)-pyrazin-2-yl]-phenyl}-propionic acid |
| 39 | 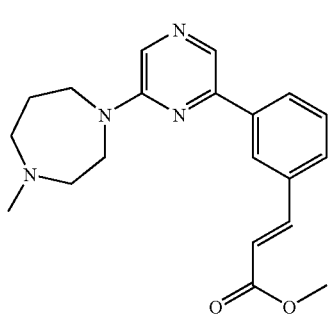 | (E)-3-{3-[6-(4-Methyl-[1,4]diazepan-1-yl)-pyrazin-2-yl]-phenyl}-acrylic acid methyl ester |
| 40 | 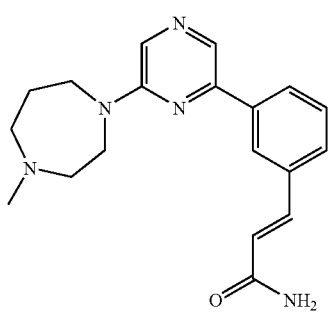 | (E)-3-{3-[6-(4-Methyl-[1,4]diazepan-1-yl)-pyrazin-2-yl]-phenyl}-acrylamide |
| 41 | 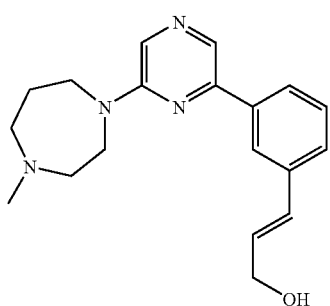 | (E)-3-{3-[6-(4-Methyl-[1,4]diazepan-1-yl)-pyrazin-2-yl]-phenyl}-prop-2-en-1-ol |

-continued

| Cpd # | Structure | name |
|---|---|---|
| 42 | 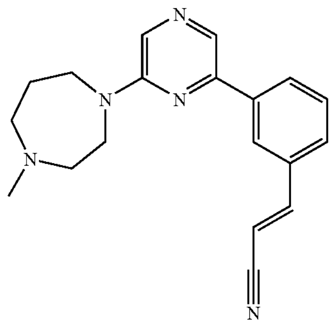 | (E)-3-{3-[6-(4-Methyl-[1,4]diazepan-1-yl)-pyrazin-2-yl]-phenyl}-acrylonitrile |
| 43 | 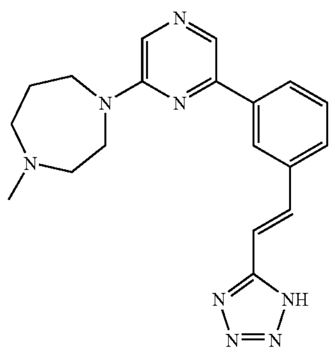 | 1-Methyl-4-(6-{3-[(E)-2-(1H-tetrazol-5-yl)-vinyl]-phenyl}-pyrazin-2-yl)-[1,4]diazepane |
| 44 | 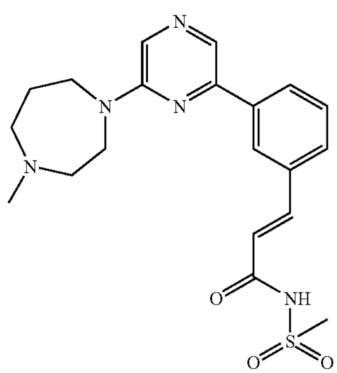 | N-((E)-3-{3-[6-(4-Methyl-perhydro-1,4-diazepin-1-yl)-pyrazin-2-yl]-phenyl}-acryloyl)-methanesulfonamide |
| 45 | | (E)-N-(2-Hydroxy-ethyl)-3-{3-[6-(4-methyl-perhydro-1,4-diazepin-1-yl)-pyrazin-2-yl]-phenyl}-acrylamide | or the pharmaceutically acceptable salts thereof.

10. A compound according to claim 9 chosen from:

| Cpd # | Structure | name |
|---|---|---|
| 1 | 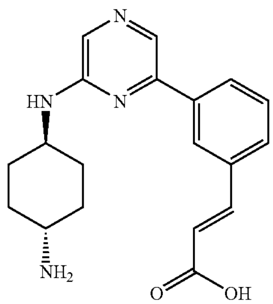 | (E)-3-{3-[6-(4-Amino-cyclohexylamino)-pyrazin-2-yl]-phenyl}-acrylic acid |
| 2 | 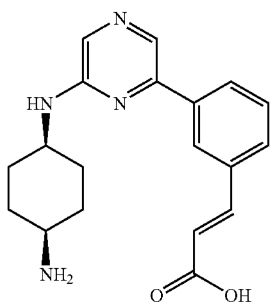 | (E)-3-{3-[6-(4-Amino-cyclohexylamino)-pyrazin-2-yl]-phenyl}-acrylic acid |
| 3 | 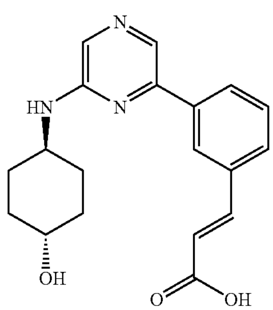 | (E)-3-{3-[6-(4-Hydroxy-cyclohexylamino)-pyrazin-2-yl]-phenyl}-acrylic acid |
| 4 | 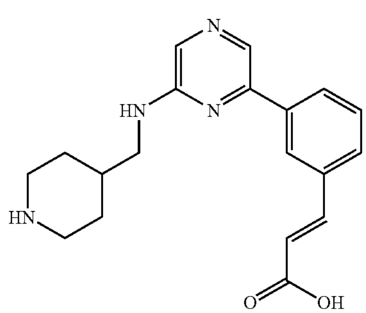 | (E)-3-(3-{6-[(Piperidin-4-ylmethyl)-amino]-pyrazin-2-yl}-phenyl)-acrylic acid |
| 5 | 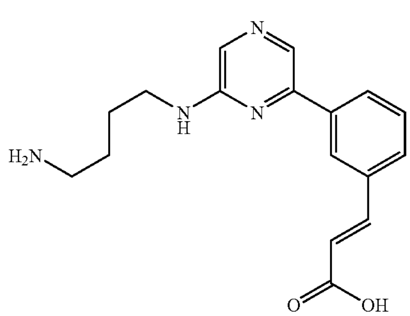 | (E)-3-{3-[6-(4-Amino-butylamino)-pyrazin-2-yl]-phenyl}-acrylic acid |

-continued

| Cpd # | Structure | name |
|---|---|---|
| 6 | 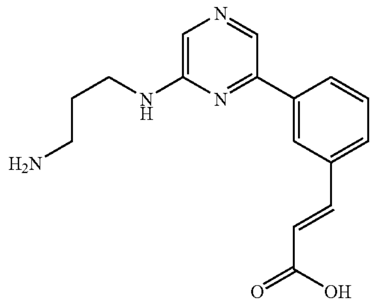 | (E)-3-{3-[6-(3-Amino-propylamino)-pyrazin-2-yl]-phenyl}-acrylic acid |
| 7 | 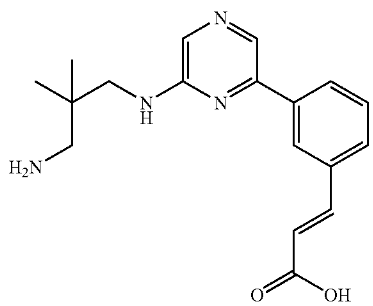 | (E)-3-{3-[6-(3-Amino-2,2-dimethyl-propylamino)-pyrazin-2-yl]-phenyl}-acrylic acid |
| 8 | 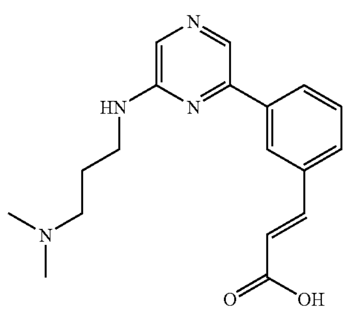 | (E)-3-{3-[6-(3-Dimethylamino-propylamino)-pyrazin-2-yl]-phenyl}-acrylic acid |
| 9 | 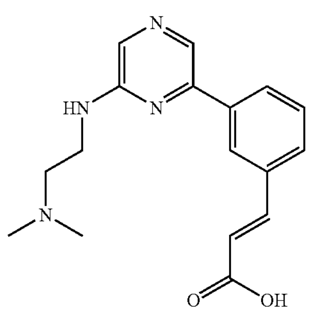 | (E)-3-{3-[6-(2-Dimethylamino-ethylamino)-pyrazin-2-yl]-phenyl}-acrylic acid |
| 10 | 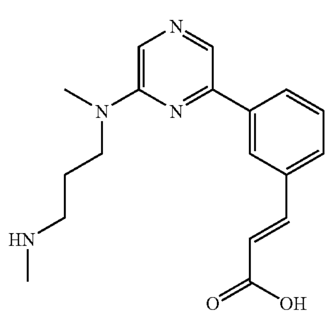 | (E)-3-(3-{6-[Methyl-(3-methylamino-propyl)-amino]-pyrazin-2-yl}-phenyl)-acrylic acid |

| Cpd # | Structure | name |
|---|---|---|
| 11 | 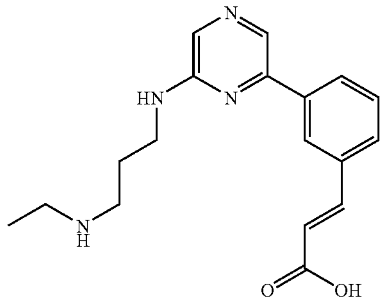 | (E)-3-{3-[6-(3-Ethylamino-propylamino)-pyrazin-2-yl]-phenyl}-acrylic acid |
| 12 | 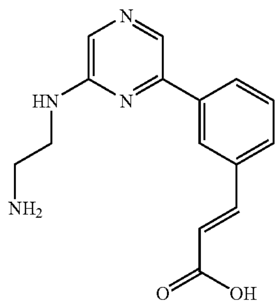 | (E)-3-{3-[6-(2-Amino-ethylamino)-pyrazin-2-yl]-phenyl}-acrylic acid |
| 13 | 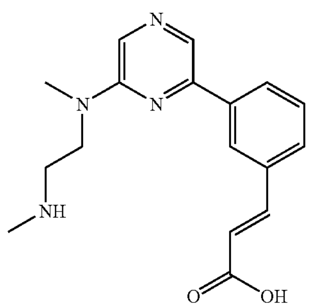 | (E)-3-(3-{6-[Methyl-(2-methylamino-ethyl)-amino]-pyrazin-2-yl}-phenyl)-acrylic acid |
| 15 | 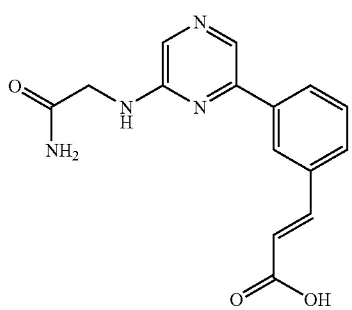 | (E)-3-{3-[6-(Carbamoylmethyl-amino)-pyrazin-2-yl]-phenyl}-acrylic acid |
| 16 | 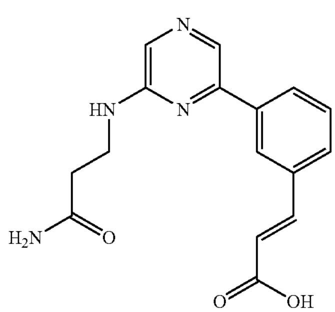 | (E)-3-{3-[6-(2-Carbamoyl-ethylamino)-pyrazin-2-yl]-phenyl}-acrylic acid; MS, electrospray |

-continued

| Cpd # | Structure | name |
|---|---|---|
| 22 | 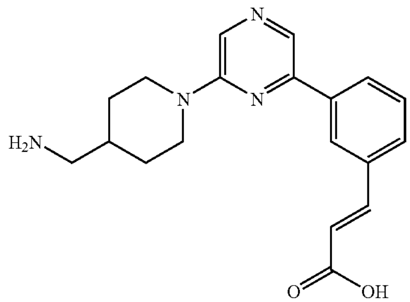 | (E)-3-{3-[6-(4-Aminomethyl-piperidin-1-yl)-pyrazin-2-yl]-phenyl}-acrylic acid |
| 23 | 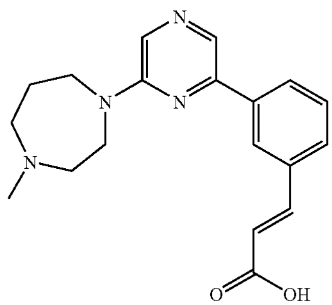 | (E)-3-{3-[6-(4-Methyl-[1,4]diazepan-1-yl)-pyrazin-2-yl]-phenyl}-acrylic acid |
| 24 | 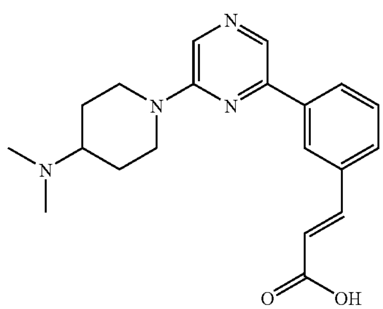 | (E)-3-{3-[6-(4-Dimethylamino-piperidin-1-yl)-pyrazin-2-yl]-phenyl}-acrylic acid |
| 25 | 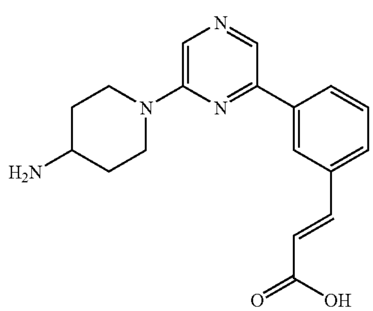 | Preparation of 14 (E)-3-{3-[6-(4-Amino-piperidin-1-yl)-pyrazin-2-yl]-phenyl}-acrylic acid |
| 26 | 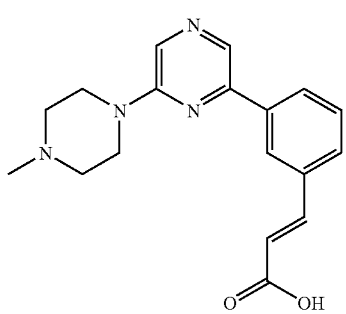 | (E)-3-[3-(4-Methyl-3,4,5,6-tetrahydro-2H-[1,2']bipyrazinyl-6'-yl)-phenyl]-acrylic acid |

| Cpd # | Structure | name |
|---|---|---|
| 27 | 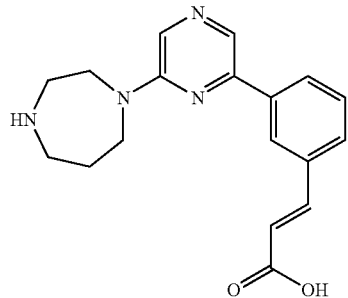 | (E)-3-[3-(6-[1,4]Diazepan-1-yl-pyrazin-2-yl)-phenyl]-acrylic acid |
| 28 | 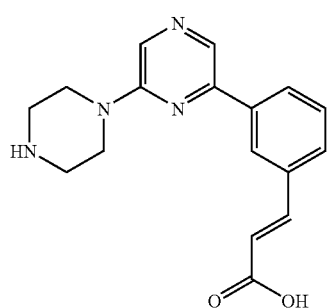 | (E)-3-[3-(3,4,5,6-Tetrahydro-2H-[1,2']bipyrazinyl-6'-yl)-phenyl]-acrylic acid |
| 29 | 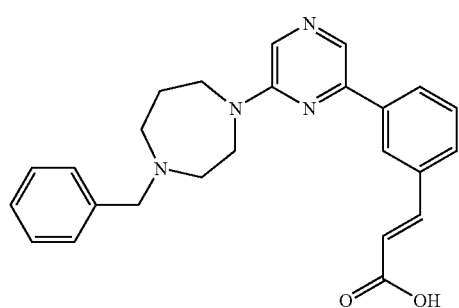 | (E)-3-{3-[6-(4-Benzyl-[1,4]diazepan-1-yl)-pyrazin-2-yl]-phenyl}-acrylic acid |
| 30 | 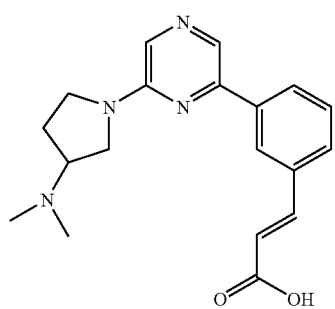 | (E)-3-{3-[6-(3-Dimethylamino-pyrrolidin-1-yl)-pyrazin-2-yl]-phenyl}-acrylic acid |

| Cpd # | Structure | name |
|---|---|---|
| 43 | | 1-Methyl-4-(6-{3-[(E)-2-(1H-tetrazol-5-yl)-vinyl]-phenyl}-pyrazin-2-yl)-[1,4]diazepane | or a pharmaceutically acceptable salt thereof.

\* \* \* \* \*